US006841559B1

(12) United States Patent
Almqvist et al.

(10) Patent No.: US 6,841,559 B1
(45) Date of Patent: Jan. 11, 2005

(54) PYRIDINONES TO TREAT AND PREVENT BACTERIAL INFECTIONS

(75) Inventors: Frederic Almqvist, Umea (SE); Hans Emtenas, Umea (SE); Scott J. Hultgren, St. Louis, MO (US); Jerome S. Pinkner, St. Louis, MO (US)

(73) Assignee: Washington University of St. Louis, St. Louis, MO (US)

( * ) Notice: Subject to any disclaimer, the term of this patent is extended or adjusted under 35 U.S.C. 154(b) by 0 days.

(21) Appl. No.: 10/130,453

(22) PCT Filed: Nov. 20, 2000

(86) PCT No.: PCT/US00/31879

§ 371 (c)(1),
(2), (4) Date: Sep. 23, 2002

(87) PCT Pub. No.: WO01/36426

PCT Pub. Date: May 25, 2001

Related U.S. Application Data
(60) Provisional application No. 60/166,621, filed on Nov. 19, 1999.

(51) Int. Cl.[7] .................... A61K 31/435; C07D 513/04; C07D 498/04; C07D 471/04
(52) U.S. Cl. .......................... 514/301; 514/80; 514/81; 514/224.2; 514/230.5; 514/299; 514/302; 514/306; 544/47; 544/90; 546/23; 546/114; 546/116; 546/138; 546/183
(58) Field of Search .......................... 546/23, 114, 116, 546/138, 183; 544/47, 90; 514/80, 81, 224.2, 230.5, 299, 302, 306, 301; 568/12

(56) References Cited

U.S. PATENT DOCUMENTS 5,310,562 A 5/1994 Margolin
5,624,677 A 4/1997 El-Rashidy et al.

FOREIGN PATENT DOCUMENTS

DD 84 850 10/1971
EP 0 133 038 A2 2/1985

OTHER PUBLICATIONS

U.S. patent application Ser. No. 09/252,792 entitled β–Lactam–Like Chaperone Inhibitors, Inventors Hultgren et al.
Almqvist et al., "Alternative Way of Synthesizing Thiazoline Derivatives," Tetrahedron Letter, 1998, vol. 29, pp. 2293–2294.
Barker et al., "Disubstituted Flourenes. Part II. The Preparation of 3:6–Diaminoflourene from Fluorene, and the Attempted Internuclear Cyclisation of Derivatives of 4:4'–Diaminodiphenylmethane," J. Org. Chem., 1954, vol. 2034, pp. 870–872.
Casinovi et al., "A New Antibiotic Produced by Strain of Aspergillus Flavipes," Tetrahedron Letters, No. 27, pp. 3175–3178.

Clive et al., "Synthesis of Recemic Brevioxime and Related Model Compounds," J. Org. Chem., 2000, vol. 65, pp. 4923–4929.
Groutas et al., "Substituted 2–Pyrones, 2–Pyridones, and Other Congeners of Elasnin as Potential Agents for the Treatment of Chronic Obstructive Lung Diseases," J. Med. Chem., 1985, vol. 28, p. 1106.
Head et al., "Validate: A New Method for the ReceptorBased Prediction of Binding Affinities of Novel Ligands," J. Am. Chem. Soc., 1996, vol. 118, pp. 3959–3969.
Karlsson et al., "Binding Peptides in Solution by the *Escherichia coli* Chaperone PapD as Revealed Using an Inhibition ELISA and NMR Spectroscopy," 1998, vol. 6, pp. 2085–2101.
Kuehn et al., "Structural Basis of Pilus Subunit Recotnition by the PapD Chaperone," Science, 1993, vol. 262, pp. 1234–1241.
Linn et al., "Solid Phase Synthesis of 1,3,5–Trisubstituted Pyridin–2–ones," Tetrahedron Letters, 1999, vol. 40, pp. 2227–2230.
Meyers et al., "Oxazolines XXIV: Chiral Oxazolines and Thiazolines from L–Serine and L–Cysteine. Their Potential Use in Asymetric Synthesis," Heterocycles, 1976, vol. 4, pp. 1687–1692.
Mukaiyama et al., "Aromatic Iodination with iodine monochloride by using a catalytic amount of ferrocenium tetrakis(3,5–bis(triflouromethyl)phenyl) borate," Tetrahedron Letters, 2000, pp. 835–838.
Olthoff et al., "Thiazolo [e,2–a] pyridones," Chemical Abstracts, 1973, vol. 78:12, p. 474.
Pawda et al., "An Isomünchnone–Based Method for the Synthesis of Highly Substituted 2(1H)–Pyridones," J. Org. Chem., 1999, vol. 64, pp. 8648–8659.
Reidlinger et al., Synthesen mit Nitrilen, LXXXVIII[1]; Cyan––Nitropropenide—Synthone zur Herstellung von Nitropyridinen, Synthesis, 1991, pp. 835–838.
Shakespeare W.C., "Palladium–Catalyzed Coupling of Lactams with Bromobenzenes," Tetrahedron Letters, 1999, vol. 40, pp. 2034–2038.

(List continued on next page.)

*Primary Examiner*—Bernard Dentz
(74) *Attorney, Agent, or Firm*—Senniger Powers

(57) ABSTRACT

Novel pyridinones and their derivatives which are effective in treating or preventing Gram-negative bacterial infections are provided. The pyridinones are stable and easily derivatized; the methods by which these derivatizations occur is described. Two regioselective and functional group tolerant methods for the synthesis of the novel pyridinones are also provided. One such synthetic method involves reacting an imine and a Meldrum's acid derivative in solution. The other synthetic method is a solid phase synthesis of the pyridinones in which an imine is prepared bound to a solid support and a Meldrum's acid derivative is reacted with the imine. Novel imine intermediates useful in the solid phase and solution methods of synthesizing the pyridionones are also described.

135 Claims, No Drawings

OTHER PUBLICATIONS

Soto et al., "Periplasmic chaperone recognition motif of subunits mediates quaternary interactions in the pilus," EMBO J., 1998, vol. 17:21, pp. 6155–6167.

Striker et al., "Structural requirements for the glycolipid receptor of human uropathogenic *Escherichia coli*," Mol. Microbiol., 1995, vol. 16, pp. 1021–1029.

Todd et al., The Synthesis of Analogs of Penicillin. I., 1953, vol. 75, pp. 1895–2000.

Wittenberger et al., "Dialkyltin Oxide Mediated Addition of Trimethylsilyl Azide to Nitriles. A Novel Preparation of 5–Substituted Tetrazoles," J. Org. Chem., 1998, vol. 58, pp. 4139–4141.

Yamamoto et al., "1,3–Oxazines and Related Compounds. XIII.[1)] Reaction of Acyl Meldrum's Acids with Schiff Bases Giving 2,3–Disubstituted 5–Acyl–3,4,5, 6–tetrahydro–2H–1,3–oxazine–4,6–diones and 2,3, 6–Trisubstituted 2,3,–Dihydro–1,3–oxazin–4–ones," Chem. Pharm. Bull., 1987, vol. 35(5), pp. 1860–1870.

Zhang et al., "Cyclogutenedione–Based Method for the Synthesis of Substituted 2–Pyridinones and Dihydro–2–pyridinones," J. Org. Chem., 1999, vol. 64, pp. 4042–4049.

Zhu et al. "The Direct Formation of Functionalized Alkyl(aryl)zinc Halldes by Oxidative Addition of Highly Reactive Zinc with Organic Halides and Their Reactions with Acid Chlorides, α,β–Unsaturated Ketones, and Allylic, Aryl, and Vinyl Halides," J. Org. Chem., 1991, vol. 56, pp. 1445–1453.

Capps, N.K. et al., Synthesis of Bicyclic Pyridone and Dihydropyridone Analogues of β–Lactam Antiobiotics, J. Chem. Soc. Perkin Trans., (1991), pp. 3077–3086.

Fang, F.G. et al., Total Synthesis of the Angiotensin–Converting Enzyme Inhibitor A58365A: On the Use of Pyroglutamate as a Chiral Educt, Tetrahedron Letters, (1989), pp. 3621–3624, vol. 30:28.

Supplementary Partial European Search Report from EP 00 98 2170 dtd Jan. 27, 2003.

PYRIDINONES TO TREAT AND PREVENT BACTERIAL INFECTIONS

CROSS-REFERENCE TO RELATED APPLICATIONS

This application claims the benefit of U.S. Provisional Application No. 60/166,621 filed Nov. 19, 1999 and this application is a 371 of PCT/US00/31879, filed Nov. 20, 2000.

GOVERNMENT SPONSORSHIP

Statement of Rights to Inventions made under Federally Sponsored Research. The invention disclosed herein was made in part with Government support under Grant Number RO1AI29549 awarded by the National Institute of Health. The Government bas certain rights in this invention.

FIELD OF INVENTION

The invention relates to novel pyridinones useful for treating infections caused by Gram-negative bacteria and to novel methods for synthesizing and using these pyridinones.

BACKGROUND ART

Pili are hair-like adhesive organelles found on a wide variety of pathogenic bacteria that are employed to adhere to and colonize host tissues by binding to receptors in the host tissues. Pili are heteropolymeric surface fibers with an adhesive tip and consist of two major sub-assemblies, the pilus rod and the tip fibrillum. The pilus rod is a thick rigid rod made up of repeating subunits arranged in a right handed helical cylinder whereas the tip fibrillum is a thin, flexible tip fiber extending from the distal end of the pilus rod and is composed primarily of repeating subunits arranged in an open helical configuration. Periplasmic chaperones are involved in a molecular mechanism necessary for guiding biogenesis of adhesive organelles in Gram-negative bacteria. These periplasmic chaperones facilitate the assembly of competent complexes from subunits. The periplasmic chaperones are so critical to the functioning of the pili that in the absence of an interaction with the chaperone, pilus subunits aggregate and are proteolytically degraded. Pathogenic Gram-negative bacteria include organisms such as *Escherichia coli, Haemophilus influenzae, Salmonella enteriditis, Salmonella typhimirium, Bordetella pertussis, Yersinia pestis, Yersinia enterocolitca, Helicobacter pylori* and *Klebsiella pneumoniae.*

The prevention or inhibition of normal pilus assembly in Gram-negative bacterium impacts the pathogenicity of the bacterium by preventing the bacterium from infecting host tissues. Drugs that interfere with the assembly of pili should effectively disable pathogens responsible for a wide variety of Gram-negative infections, such as those responsible for bladder, kidney and middle ear infections as well as food poisoning, gastric ulcers, diarrhea, meningitis, and other illnesses. Drugs that interfere with the assembly of pili are known collectively as pilicides.

One class of pilicides that has been developed are those with a β-lactam-like structure. These pilicides are described in patent application Ser. No. 9/252,792, entitled β-Lactam-Like Chaperone Inhibitors, invented by Scott Hultgren/Fredrik Almqvist.

Certain compounds noted for other structural components but containing 2-pyridinone substructures have been reported to possess medicinal properties. Some of these compounds are suggested to be antibacterial and antifungal agents and some are disclosed as free radical scavengers. Free radicals play a role in a variety of diseases, including cardiovascular disease, connective tissue damage, inflammatory disorder and CNS injury. See Zhang et al, Cyclobutenedione-Based Method for the Synthesis of Substituted 2-Pyridinones and Dihydro-2-pyridinones, *J.Org.Chem.* 1999, 64, 4042–4049; Casinovi, et al, A New Antibiotic Produced By A Strain of *Aspergillus Flavipes, Tetrahedron Letters,* No. 27, 3175–3178.

N-substituted 2-pyridinones themselves have been employed as active ingredients for the therapy of fibrotic disease and have been evaluated as inhibitors of human leukocyte elastase. Margolin, S. B. U.S. Pat. No. 5,310,562. Some synthetic 2-pyridinones have also demonstrated high hypotensive or cardiotropic activity. Grontas, W. C., Stanga, M. A., Brobaker, M. J., Huang T. L., Moi, M. L., Carroll, R. T. *J. Med. Chem.* 1985, 28, 1106. The usefulness of these pyridinones has generated intense interest in the medical applications of pyridinones and consequently the synthesis of compounds containing a 2-pyridinone substructure has become increasingly important. However, N-substituted, 2-pyridinones have not previously been known to interfere with pilus formation in Gram-negative bacteria.

A number of methods for the preparation of substituted 2-pyridinones have been reported in the literature and are known. One such method involves the oxidation of pyridinium salts to the corresponding 2-pyridinones with ferricyanide under basic conditions. Although the synthesis is straightforward, the method is limited by the availability of the corresponding pyridinium salts. Many 2-pyridinone methodologies incorporate the Michael addition, the nucleophilic addition of carbanions to α,β-unsaturated ketones, as a key step in the formation of six-membered rings. Cycloaddition procedures have also been employed to synthesize 2-pyridinones.

In Cyclobutenedione-Based Method for the Synthesis of Substituted 2-Pyridinones and Dihydro-2-pyridinones, *J. Org. Chem.* 64,11:4042 authors Shijie Zhang and Lanny Liebeskind report a synthesis of a 1,2 addition of N-Boc protected α-amino carbanions to cyclobutenediones, subsequent methylation, and thermal ring expansion. Treatment with NBS/pyridine yielded the desired substituted 2-pyridinones.

Solid phase synthesis has been employed in the preparation of certain pyridinones. In Solid Phase Synthesis of 1,3,5-Trisubstituted Pyridin-2-ones, *Tetrahedron Letters,* 40(1999) 2227–2230 authors James A. Linn et al. report the solid phase synthesis of 1,3,5-trisubstituted pyridin-2-ones via selective NH-alkylation of 3-amino-5-carbomethoxy-1H-pyridin-2-one using a solid supported halo-acid. The synthesis proceeds by the coupling of 6-bromohexanoic acid to a Rink amine macrocrown to form a solid-supported 6-bromohexanamide. The solid-supported 6-bromohexanamide was used to alklylate 3-amino-5-carbomethoxy-1H-pyridin-2-one which was then reacted with diphenylacetic acid. Saponification of the resulting ester yielded a solid supported carboxylic acid. Treatment of the solid supported carboxylic acid with pentafluorophenol provided the pentafluorophenyl ester, which when treated with benzylamine was cleaved from the macrocrown to give the pyridinone. However, a solid phase synthesis procedure to produce ring fused 2-pyridinones has not yet been reported.

Many of the known methods of production of pyridinones create a racemic mixture of compounds rather than one enantiomer of the compound. Thus, although a number of synthetic routes to produce pyridinones are known, some of which are functional group tolerant, there is continuing interest in novel, straightforward, regioselective and functional group tolerant synthetic methods, due to the roles 2-pyridinones and compounds containing a 2-pyridinone substructure play in a variety of medical applications. Solid phase synthesis procedures specifically for the production of the pyridinone substructure are desirable because of the ability of this synthetic procedure to yield relatively pure compounds. Thus, solid phase synthesis possesses the additional advantage of the simplicity of purifying compounds produced by it in addition to the advantages of being regioselective and functional group tolerant. Solid phase synthesis is particularly useful in the making of libraries for biological testing and biological uses; solid phase synthesis is amenable to the use of automation by machines.

The contents of all publications and U.S. patents and patent applications referred to hereinafter are hereby incorporated by reference to the extent necessary and to the same extent as though each were individually so incorporated.

SUMMARY OF THE INVENTION

The present invention provides a novel class of pyridinones which are effective in treating or preventing Gram-negative bacterial infections. These pyridinones are highly stable and easily derivatized. Without intending to be bound by any theory, applicants believe that the compounds of the invention exert their effects by interfering with the function of chaperones required for the assembly of pili from pilus subunits in diverse Gram-negative bacteria Such interference is particularly effective since the formation of pili is essential to bacterial pathogenicity and since the production of the pilus subunits in the absence of chaperones is known to be directly toxic. The novel pyridinones of the invention comprise pyridinones having the formula:

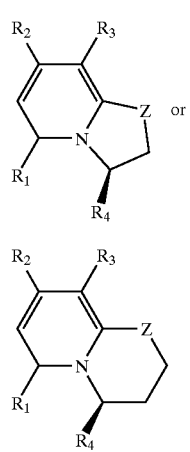

and the salts thereof wherein Z comprises S, SO, SO$_2$, O, P, PO, PO$_2$, CH$_2$, or CR$_2$; R$_1$ comprises oxo; R$_2$ comprises (CH)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl alkenyl, alkynyl, aryl, heteroaryl, substituted alkyl, substituted alkenyl, substituted alkynyl, substituted aryl or substituted heteroaryl; R$_4$ comprises CO$_2$Y, B(OY)$_2$, CHO, CH$_2$OY, CH(CO$_2$Y)$_2$, PO(OY)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

Pyridinones (C) and (E) of the present invention can be easily derivatized to further novel pyridinones having the formula:

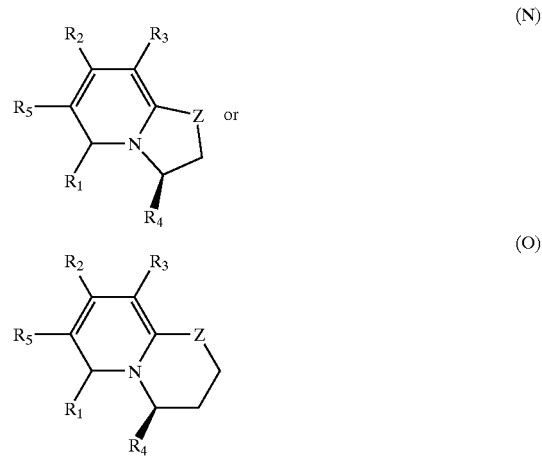

wherein R$_1$, R$_2$, R$_3$, R$_4$ and Z are as previously defined and R$_5$ comprises halogen, nitrile, CO$_2$H, CH$_2$NH$_2$, cyclic CHN$_4$, a lactam, NO$_2$, (trimethylsilyl)acetylene, G wherein G comprises alkyl, alkenyl, alkynyl aryl, substituted alkyl, substituted alkenyl, substituted alkynyl, substituted aryl, or (CH)$_2$E wherein E comprises COR, CO$_2$R, CHO, or CN and R comprises alkyl, alkenyl, alkynyl, aryl, heteroaryl, substituted alkyl, substituted alkenyl, substituted alkynyl, substituted aryl or substituted heteroaryl.

Furthermore, pyridinone (C) can be reduced to form compounds having the formula:

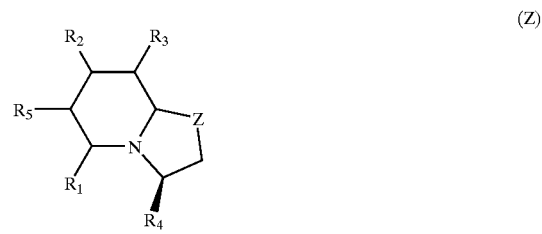

wherein when Z comprises SO, SO$_2$, O, P, PO, PO$_2$, CH$_2$, or CR$_2$; R$_1$ comprises oxo; R$_2$ comprises (CH$_2$)$_n$A wherein n is a natural number between 0 and 5 and A comprises alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl alkenyl, alkynyl, aryl, heteroaryl, substituted alkyl, substituted alkenyl, substituted alkynyl, substituted aryl or substituted heteroaryl; R$_4$ comprises CO$_2$Y, B(OY)$_2$, CHO, CH$_2$OY, CH(CO$_2$Y)$_2$, PO(OY)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl; R$_5$ comprises hydrogen, halogen, nitrile, CO$_2$H, CH$_2$NH$_2$, cyclic CHN$_4$, a lactam, NO$_2$, (trimethylsilyl)acetylene, G wherein G comprises alkyl, alkenyl, alkynyl, aryl, substituted alkyl, substituted alkenyl, substituted alkynyl, substituted aryl, or (CH)$_2$E wherein E comprises COR, CO$_2$R, CHO, or CN and R comprises alkyl, alkenyl, alkynyl, aryl, heteroaryl, substituted alkyl, substituted alkenyl, substituted alkynyl, substituted aryl or substituted heteroaryl;

and when Z comprises S, R$_1$ comprises oxo; R$_2$ comprises (CH$_2$)$_n$A wherein n is a natural number between 0 and 5 and A comprises alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and R$_4$ comprises CO$_2$Y, B(OY)$_2$, CHO, CH$_2$OY, CH(CO$_2$Y)$_2$, PO(OY)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl; and R$_5$ comprises hydrogen, halogen, nitrile, CO$_2$H, CH$_2$NH$_2$, cyclic CHN$_4$, a lactam, NO$_2$, (trimethylsilyl)acetylene, G wherein G comprises alkenyl, alkynyl, aryl, substituted alkenyl, substituted alkynyl, substituted aryl, or (CH)$_2$E wherein E comprises COR, CO$_2$R, CHO, or CN and R comprises alkyl, alkenyl, alkynyl, aryl, heteroaryl, substituted alkyl, substituted alkenyl, substituted alkynyl, substituted aryl or substituted heteroaryl.

Pyridinones (E) can be reduced to form compounds having the formula:

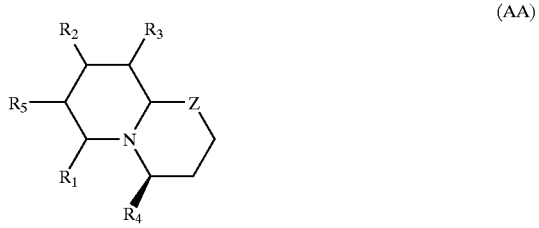

(AA)

wherein when Z comprises S, SO, SO$_2$, O, P, PO, PO$_2$, or CR$_2$; R$_1$ comprises oxo; R$_2$ comprises (CH$_2$)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; R$_4$ comprises CO$_2$Y, B(OY)$_2$, CHO, CH$_2$OY, CH(CO$_2$Y)$_2$, PO(OY)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl; R$_5$ comprises hydrogen, halogen, nitrile, CO$_2$H, CH$_2$NH$_2$, cyclic CHN$_4$, a lactam, NO$_2$, (trimethylsilyl)acetylene, G wherein G comprises alkyl, alkenyl, alkynyl, aryl, substituted alkyl, substituted alkenyl, substituted alkynyl, substituted aryl, or (CH)$_2$E wherein E comprises COR, CO$_2$R, CHO, or CN and R comprises alkyl, alkenyl, alkynyl, aryl, heteroaryl, substituted alkyl, substituted alkenyl, substituted alkynyl, substituted aryl or substituted heteroaryl; and when Z comprises CH$_2$, R$_1$, R$_2$, R$_3$, and R$_4$ are as previously defined and R$_5$ is hydrogen, halogen, nitrile, CO$_2$H, CH$_2$NH$_2$, cyclic CHN$_4$, a lactam, NO$_2$, (trimethylsilyl)acetylene, G wherein G comprises alkenyl, alkynyl, aryl, substituted alkenyl, substituted alkynyl, substituted aryl, or (CH)$_2$E wherein E comprises COR, CO$_2$R, CHO, or CN and R comprises alkyl, alkenyl, alkynyl, aryl, heteroaryl, substituted alkyl, substituted alkenyl, substituted alkynyl, substituted aryl or substituted heteroaryl.

The invention is also directed to novel methods of synthesizing substituted 2-pyridinones (C) and (E). The first of these methods is a preparation in solution reacting a Meldrum's acid derivative (A) (a derivative of 5-acyl-2,2-dimethyl-1,3-dioxane-4,6-dione) with imines (B) or (D) in acidic conditions. The second of these methods is a solid phase synthesis in which a imine bound to a resin is prepared. A Meldrum's acid derivative is reacted with the resin bound imine in acidic conditions to form the pyridinone.

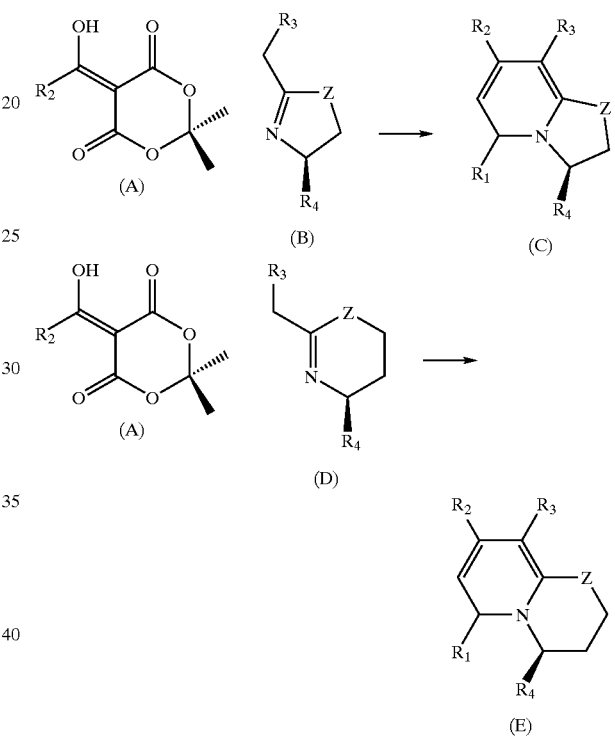

The invention is also directed to methods of derivatizing compounds (C) and (E) to form compounds (N) and (O) and methods of reducing compounds (C) and (E) to form compounds (Z) and (AA).

The invention is further directed to various compounds that are useful in the preparation of the pyridinones and pyridinone derivatives. These include an imine of the formula:

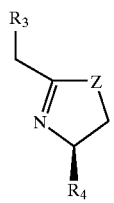

wherein Z comprises S, SO, SO$_2$, O, P, PO, PO$_2$, CH$_2$, or CR$_2$; R$_2$ comprises (CH$_2$)$_n$A wherein n is a natural number between 0 and 5 and A comprises alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5: when m is between 3 and 5, D comprises alkyl, alkenyl, alkynyl, aryl, heteroaryl, substituted alkyl, substituted alkenyl, substituted alkynyl, substituted aryl or substituted heteroaryl; when m is 0, D comprises unsubstituted alkenyl, unsubstituted or substituted alkynyl, unsubstituted or substituted aryl, unsubstituted heteroaryl; when m is 1, D comprises unsubstituted alkyl, unsubstituted alkenyl, unsubstituted or substituted alkynyl, unsubstituted aryl, or substituted or unsubstituted heteroaryl; and when m is 2, D comprises unsubstituted alkyl, unsubstituted or substituted alkenyl, unsubstituted or substituted alkynyl, unsubstituted aryl, or unsubstituted or substituted heteroaryl; $R_4$ comprises $CO_2G$, $B(OY)_2$, $CH_2OY$, $CH(CO_2Y)_2$, CHO, $PO(OY)_2$ wherein Y comprises hydrogen, alkyl, alkenyl, alkynyl, aryl, heteroaryl substituted alkyl, substituted alkenyl substituted alkynyl, substituted aryl or substituted heteroaryl and G comprises alkyl, alkenyl, alkynyl, aryl, heteroaryl, substituted alkyl, substituted alkenyl, substituted alkynyl, substituted aryl or substituted heteroaryl;

and another imine of the formula:

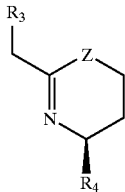

wherein Z comprises S, SO, $SO_2$, O, P, PO, $PO_2$, $CH_2$, or $CR_2$; $R_2$ comprises $(CH_2)_nA$ wherein n is a natural number between 0 and 5 and A comprises alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5: when m is between 1 and 5, D comprises alkyl, alkenyl, alkynyl, aryl, heteroaryl, substituted alkyl, substituted alkenyl, substituted alkynyl, substituted aryl or substituted heteroaryl; and when m is 0, D comprises unsubstituted alkyl, substituted or unsubstituted alkenyl, substituted or unsubstituted alkynyl, substituted aryl, substituted or unsubstituted heteroaryl; $R_4$ comprises $CO_2J$, $B(OY)_2$, $CH(CO_2Y)_2$, $PO(OY)_2$, $CH_2OY$, CHO wherein Y comprises hydrogen, alkyl, alkenyl, alkynyl, aryl, heteroaryl, substituted alkyl, substituted alkenyl, substituted alkynyl, substituted aryl or substituted heteroaryl and J comprises methyl, alkenyl, alkynyl, aryl, heteroaryl, substituted methyl, substituted alkenyl, substituted alkynyl substituted aryl or substituted heteroaryl.

In additional aspects the invention is directed to methods to inhibit or prevent bacterial growth using the compounds of the invention, to antibodies specific for such compounds and to antimicrobial compositions, including pharmaceutical compositions containing these compounds.

DETAILED DESCRIPTION

The present invention provides pyridinones of the formula:

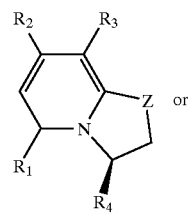 (C)

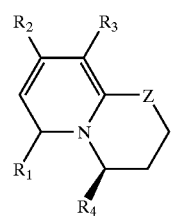 (E)

and the salts thereof wherein Z comprises S, SO, $SO_2$, O, P, PO, $PO_2$, $CH_2$, or $CR_2$; $R_1$ comprises oxo; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; $R_4$ comprises $CO_2Y$, $B(OY)_2$, CHO, $CH_2OY$, $CH(CO_2Y)_2$, $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

These pyridinones are highly stable and can be readily derivatized in a number of ways. One such method of derivatization is a further substitution on the aromatic ring of the pyridinone. Thus, the present invention also provides pyridinone derivatives having the formula:

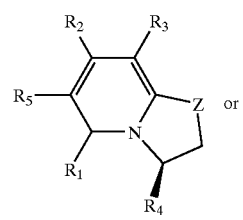 (N)

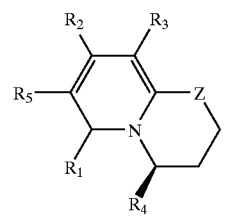 (O)

and the salts thereof wherein $R_1$, $R_2$, $R_3$, $R_4$ and Z are as previously defined and $R_5$ comprises halogen, nitrile, $CO_2H$, $CH_2NH_2$, cyclic $CHN_4$, a lactam, $NO_2$, (trimethylsilyl) acetylene, G wherein G comprises alkyl, alkenyl, alkynyl, aryl, substituted alkyl, substituted alkenyl, substituted alkynyl, substituted aryl, or $(CH_2)_2E$ wherein E comprises COR, $CO_2R$, CHO, or CN and R comprises alkyl, alkenyl alkynyl, aryl, heteroaryl, substituted alkyl, substituted alkenyl, substituted alkynyl, substituted aryl or substituted heteroaryl. Pyridinone derivatives (N) and (O) are readily formed from the derivatization of pyridinones (C) and (E).

The active forms of the pyridinones and pyridinone derivatives of the invention are those wherein the chirality of the carbon at $R_4$ is as illustrated in compounds (C) and (E) of page 9. However, in (E) when $R_4$ is COOH and Z is S the chirality of the carbon at $R_4$ is S. Furthermore, in (C) when $R_4$ is COOH and Z is S the chirality of the carbon at $R_4$ is R. The same stereochemistry is retained in the analogous compounds and derivatives (although the designation (R or S) of the chirality at each position may be different depending on the specific substitutions made). The invention also includes racemic mixtures which include the active stereoisomer as well as mixtures of the various diastereomers.

The salts of the pyridinones and pyridinone derivatives possessing a carboxylic acid functionality are included in the invention, especially pharmaceutically acceptable salts. Salts of carboxylic acids include those derived from inorganic bases such as sodium, potassium, lithium, calcium, magnesium, zinc, aluminum, iron and similar salts. Also included are those salts derived from organic, especially nontoxic bases including primary amines such as ammonium, secondary and tertiary amines, substituted amines including naturally occurring substituted amines, cyclic amines, and basic ion-exchange resins.

In the following embodiments pyridinone refers to both pyridinones (C) and (E) and pyridinone derivatives (N) and (O), unless indicated otherwise. Generally, in preferred embodiments of the pyridinone, $R_4$ is $CO_2H$; test data indicates that those pyridinones possessing a carboxylic acid functionality are highly effective pilicides.

In one embodiment of the invention the pyridinone possesses the following substituents: Z comprises S or $SO_2$; $R_1$ comprises oxo, $R_2$ comprises $(CH_2)_nA$ wherein n is 1 and A comprises $C_{10}$ aryl; $R_3$ comprises $(CH_2)_mD$ wherein m is 1 and D comprises heteroaryl or substituted heteroaryl; and $R_4$ comprises $CO_2Y$ wherein Y comprises hydrogen.

In another embodiment of the invention the pyridinone possesses the following substituents: Z comprises S or $SO_2$; $R_1$ comprises oxo, $R_2$ comprises $(CH_2)_nA$ wherein n is 1 and A comprises $C_{10}$ aryl; $R_3$ comprises phenyl; and $R_4$ comprises $CO_2Y$ wherein Y comprises methyl.

In an additional embodiment of the invention the pyridinone possesses the following substituents: Z comprises S or $SO_2$; $R_1$ comprises oxo, $R_2$ comprises $(CH_2)_nA$ wherein n is 1 and A comprises $C_{10}$ aryl; $R_3$ comprises a heteroaryl of the structure:

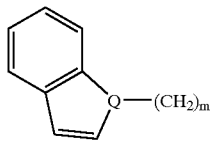

wherein m is 0–4, Q comprises N; and $R_4$ comprises $CO_2Y$ wherein Y comprises hydrogen.

In still another embodiment of the invention the pyridinone possesses the following substituents: Z comprises S or $SO_2$; $R_1$ comprises oxo, $R_2$ comprises $(CH_2)_nA$ wherein n is 1 and A comprises $C_{10}$ aryl; $R_3$ comprises a heteroaryl of the structure:

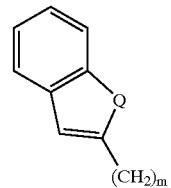

wherein m is 0–4 and Q comprises O, S, SO, $SO_2$, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

In yet another embodiment of the invention the pyridinone possesses the following substituents: Z comprises S or $SO_2$; $R_1$ comprises oxo, $R_2$ comprises $(CH_2)_nA$ wherein n is 1 and A comprises $C_{10}$ aryl; $R_3$ comprises a heteroaryl of the structure:

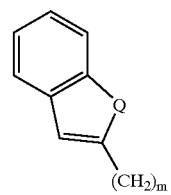

wherein m is 1 and Q comprises O, S, SO, $SO_2$, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

In an additional embodiment of the invention the pyridinone possesses the following substituents: Z comprises S or $SO_2$; $R_1$ comprises oxo, $R_2$ comprises $(CH_2)_nA$ wherein n is 1 and A comprises $C_{10}$ aryl; $R_3$ comprises a heteroaryl of the structure:

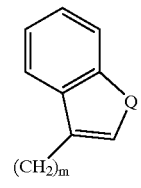

wherein m is 0–4 and Q comprises O, S, SO, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

In another embodiment or the invention the pyridinone possesses the following substituents: Z comprises $SO_2$; $R_1$ comprises oxo, $R_2$ comprises $(CH_2)_nA$ wherein n is 1 and A comprises $C_{10}$ aryl; $R_3$ comprises a heteroaryl of the structure:

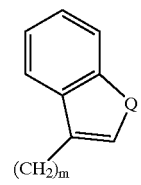

wherein m is 1 and Q comprises O, S, SO, $SO_2$, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

In still another embodiment of the invention the pyridinone possesses the following substituents: Z comprises S or $SO_2$; $R_1$ comprises oxo, $R_2$ comprises $(CH_2)_nA$ wherein n is 1 and A comprises $C_{10}$ aryl: $R_3$ comprises a heteroaryl of the structure:

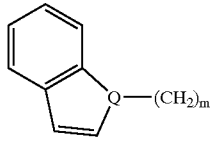

wherein m is 1 and Q comprises N; and $R_4$ comprises $CO_2Y$ wherein Y comprises hydrogen.

In an additional embodiment of the invention the pyridinone possesses the following substituents: Z comprises $SO_2$; $R_1$ comprises oxo, $R_2$ comprises $(CH_2)_nA$ wherein n is 1 and A comprises $C_{10}$ aryl; $R_3$ comprises phenyl; and $R_4$ comprises $CO_2Y$ wherein Y comprises methyl.

In another embodiment of the invention the pyridinone possesses the following substituents: Z comprises S; $R_1$ comprises oxo, $R_2$ comprises $(CH_2)_nA$ wherein is 1 and A comprises $C_{10}$ aryl, $R_3$ comprises $(CH_2)_m$ wherein m is 0; and $R_4$ comprises $CO_2Y$ wherein Y comprises methyl.

In another embodiment of the invention the pyridinone possesses the following substituents: Z comprises S; $R_1$ comprises oxo, $R_2$ comprises $(CH_2)_nA$ wherein n is 1 and A comprises $C_{10}$ aryl; $R_3$ comprises $(CH_2)_m$ wherein m is 0; and comprises $CO_2Y$ wherein Y comprises hydrogen.

In another embodiment of the invention the pyridinone possesses the following substituents: Z comprises S; $R_1$ comprises oxo, $R_2$ comprises $(CH_2)_nA$ wherein n is 1 and A comprises $C_{10}$ aryl; $R_3$ comprises phenyl; and $R_4$ comprises $CO_2Y$ wherein Y comprises methyl.

In a preferred embodiment of the invention the pyridinone possesses the following substituents: Z comprises $SO_2$; $R_1$ comprises oxo, $R_2$ comprises $(CH_2)_nA$ wherein n is 1 and A comprises $C_{10}$ aryl; $R_3$ comprises phenyl; and $R_4$ comprises $CO_2Y$ wherein Y comprises hydrogen.

In a more preferred embodiment of the invention the pyridinone possesses the following substituents: Z comprises S; $R_1$ comprises oxo, $R_2$ comprises $(CH_2)_nA$ wherein n is 1 and A comprises $C_{10}$ aryl; $R_3$ comprises phenyl; and $R_4$ comprises $CO_2Y$ wherein Y comprises hydrogen.

Preferably, $R_5$ of pyridinone derivatives (N) and (O) comprises halogen, nitrile or $(CH)_2E$ wherein E comprises $CO_2R$ and R comprises alkyl.

More preferably, $R_5$ of pyridinone derivatives (N) and (O) comprises bromine, nitrite or $(CH)_2E$ wherein E comprises $CO_2R$ and R comprises benzyl.

An additional way in which the pyridinones of the invention can be derivatized is by reduction of the aromatic ring of the pyridinone (C) or (E). The present invention therefore provides reduced pyridinone derivative (Z) having the following formula which can be prepared by reducing pyridinone (C):

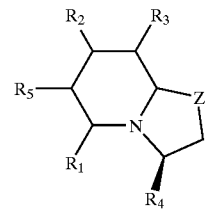

(Z)

wherein when Z comprises SO, $SO_2$, O, P, PO, $PO_2$, $CH_2$, or $CR_2$; $R_1$ comprises oxo; $R_2$ comprises $(CH_2)_nA$ wherein n is a natural number between 0 and 5 and A comprises alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; $R_4$ comprises $CO_2Y$, $B(OY)_2$, CHO, $CH_2OY$, $CH(CO_2Y)_2$, $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl; $R_5$ is hydrogen, halogen, nitrile, $CO_2H$, $CH_2NH_2$, cyclic $CHN_4$, a lactam, $NO_2$, (trimethylsilyl)acetylene, G wherein G comprises alkyl, alkenyl, alkynyl, aryl, substituted alkyl, substituted alkenyl substituted alkynyl, substituted aryl, or $(CH)_2E$ wherein E comprises COR, $CO_2R$, CHO, or CN and R comprises alkyl, alkenyl, alkynyl, aryl heteroaryl, substituted alkyl, substituted alkenyl, substituted alkynyl, substituted aryl or substituted heteroaryl;

and when Z comprises S, $R_1$ is oxo; $R_2$ comprises $(CH_2)_nA$ wherein n is a natural number between 0 and 5 and A comprises alkyl, alkenyl, alkynyl, aryl heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, CHO, $CH_2OY$, $CH(CO_2Y)_2$, $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl; and $R_5$ is hydrogen, halogen, nitrile, $CO_2H$, $CH_2NH_2$, cyclic $CHN_4$, a lactam, $NO_2$, (trimethylsilyl) acetylene, G wherein G comprises alkenyl, alkynyl, aryl, substituted alkenyl, substituted alkynyl, substituted aryl, or $(CH)_2E$ wherein E comprises COR, $CO_2R$, CHO, or CN and R comprises alkyl, alkenyl, alkynyl, aryl, heteroaryl, substituted alkyl, substituted alkenyl, substituted alkynyl, substituted aryl or substituted heteroaryl.

The invention also provides reduced pyridinone derivative (AA) having the following formula which can be prepared by reducing pyridinone (E):

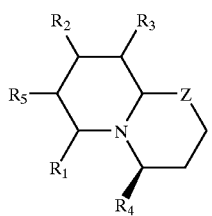

(AA)

wherein when Z comprises S, SO, SO$_2$, O, P, PO, PO$_2$, or CR$_2$; R$_1$ comprises oxo; R$_2$ comprises (CH$_2$)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; R$_4$ comprises CO$_2$Y, B(OY)$_2$, CHO, CH$_2$OY, CH(CO$_2$Y)$_2$, PO(OY)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl; R$_5$ is hydrogen, halogen, nitrile, CO$_2$H, CH$_2$NH$_2$, cyclic CHN$_4$, a lactam, NO$_2$, (trimethylsilyl) acetylene, G wherein G comprises alkyl, alkenyl, alkynyl, aryl, substituted alkyl, substituted alkenyl, substituted alkynyl, substituted aryl, or (CH)$_2$E wherein E comprises COR, CO$_2$R, CHO, or CN and R comprises alkyl, alkenyl, alkynyl, aryl, heteroaryl, substituted alkyl, substituted alkenyl, substituted alkynyl, substituted aryl or substituted heteroaryl; and when Z comprises CH$_2$, R$_1$, R$_2$, R$_3$, and R$_4$ are as previously defined and R$_5$ is hydrogen, halogen, nitrile, CO$_2$H, CH$_2$NH$_2$, cyclic CHN$_4$, a lactam, NO$_2$, (trimethylsilyl) acetylene, G wherein G comprises alkyl, alkenyl, alkynyl, aryl, substituted alkenyl, substituted alkynyl, substituted aryl, or (CH)$_2$E wherein E comprises COR, CO$_2$R, CHO, or CN and R comprises alkyl, alkenyl, alkynyl, aryl, heteroaryl, substituted alkyl, substituted alkenyl, substituted alkynyl, substituted aryl or substituted heteroaryl.

Definitions

The alkyl groups described herein, either alone or with the various substituents defined herein are preferably lower alkyl containing from one to four carbon atoms in the principal chain and up to 6 carbon atoms. They may be substituted, straight, branched chain or cyclic and include methyl ethyl, propyl, isopropyl, butyl, hexyl, cyclopropyl, cyclobutyl, cyclopentyl, cyclohexyl and the like.

The alkenyl groups described herein, either alone or with the various substituents defined herein are preferably lower alkenyl containing from two to four carbon atoms in the principal chain and up to 6 carbon atoms. They may be substituted, straight, branched chain or cyclic and include ethenyl, propenyl, isopropenyl, butenyl, hexenyl, cyclopropenyl, cyclobutenyl, cyclopentenyl, cyclohexenyl and the like.

The alkynyl groups described herein, either alone or with the various substituents defined herein are preferably lower alkynyl containing from two to four carbon atoms in the principal chain and up to 6 carbon atoms. They may be substituted, straight, or branched chain and include ethynyl, propynyl, butynyl, hexynyl and the like.

The aryl moieties described herein either alone or with various substituents, contain from 6 to 15 carbon atoms and include phenyl. Substituents include alkanoxy, halogen, hydroxyl, alkyl, aryl, alkenyl, acyl, acyloxy, nitro, amino, amido, etc.

The heteroaryl moieties described herein, either alone or with various substituents, contain from 5 to 15 carbon atoms and include furans, thiophenes, indoles, furyl, pyridyl, thienyl, tryptophane and the like. Substituents include alkanoxy, halogen, hydroxyl, alkyl, aryl, alkenyl, acyl, acyloxy, nitro, amino and amido.

The substituents of the substituted alkyl, alkenyl, alkynyl, aryl, and heteroaryl groups and moieties described herein, may be hydroxy alkyl, alkenyl, alkynyl, aryl, heteroayl and or/may contain nitrogen, oxygen, sulfur, halogens and include, for example, lower alkoxy such as methoxy, ethoxy, butoxy, halogen such as chloro or fluoro, nitro, amino, and keto.

As used herein natural number means a positive number including zero.

As used herein the terms "pilus" or "pili" relate to fibrillar heteropolymeric structures protruding from the surface of the cell envelope of many tissue-adhering pathogenic bacteria, notably pathogenic Gram-negative bacteria. In the present specification the terms pilus and pili will be used interchangeably. A pilus is composed of a number of "pilus subunits" which constitute distinct functional parts of the intact pilus.

As used herein the term "chaperone" relates to a molecule which in living cells has the responsibility of binding to proteins in order to mature the proteins in a number of ways, such as the process of folding proteins into their native conformations, the process of assembly of pili structures, or the transport of protein in the cell. Specialized molecular chaperones are "periplasmic chaperones" which are bacterial molecular chaperones exerting their main actions in the "periplasmic space". The periplasmic space constitutes the space in between the inner and outer bacterial membrane. Periplasmic chaperones are involved in the process of correct assembly of intact pili structures. When used herein, the use of the term "chaperone" designates a molecular, periplasmic chaperone unless otherwise indicated.

As used herein, "treatment" includes both prophylaxis and therapy

Throughout the application the Moldrum's acid derivative is only presented in enol form. It is recognized, however, that the Meldrum's acid derivative exists as a tautomer. The Meldrum's acid derivative may exist primarily in the enol form, primarily in the keto form, or in a mixture of both enol and keto forms depending on the solvent. All forms and mixtures thereof are intended to be included in the term "Meldrum's acid derivative" as used herein.

As used herein the term "acidic work-up" includes but is not limited to quenching with acid, such as acetic acid, washing the resulting mixture with water, and centrifugation to remove the precipitated product.

Synthesis of Pyridinones

The present invention further provides two novel methods of synthesizing ring fused substituted 2-pyridinones. Synthesis may be done in solution and involves reacting a Meldrum's acid derivative and an imine in acidic conditions. Alternatively, a solid phase synthesis of the pyridinones is accomplished by preparing an imine bound to a solid substrate and adding a Meldrum's acid derivative in acidic conditions.

Pyridinone Synthesis in Solution

The pyridinones of the present invention can be synthesized by the following general reactions:

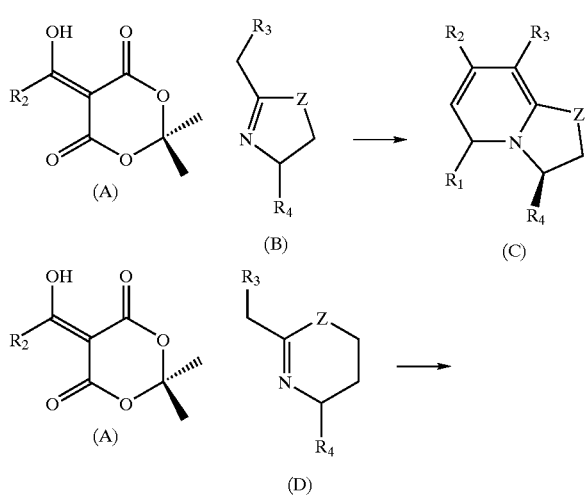

(A) (B) (C)

(A) (D)

(E)

wherein Z comprises S, SO, $SO_2$, O, P, PO, $PO_2$, $CH_2$, or $CR_2$; $R_1$ comprises oxo; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl substituted aryl or substituted heteroaryl; $R_4$ comprises $CO_2Y$, $B(OY)_2$, CHO, $CH_2OY$, $CH(CO_2Y)_2$, $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

In one embodiment of the invention Meldrum's acid derivative (A) is reacted in solution with imine (B) to form pyridinone (C). Preferably, Z comprises S or $SO_2$, n is 1, A comprises aryl, m is O, D comprises aryl, $RH_4$ comprises $CO_2Y$ wherein Y comprises hydrogen or alkyl. More preferably, Z comprises S, $R_1$ comprises oxo, n is 1, A comprises napthyl, m is O, D comprises phenyl, $R_4$ comprises $CO_2Y$ wherein Y comprises hydrogen.

The invention also includes embodiments where Y comprises alkyl, alkenyl, alkynyl, aryl, heteroaryl, substituted alkyl, substituted alkenyl, substituted alkynyl, substituted aryl or substituted heteroaryl. In these embodiments the process also comprises the further step of hydrolysis of the pyridinone. The hydrolysis can be accomplished in basic conditions through the use of a base such as NaOH or KOH, and is usually followed by acidic work-up with an acid such as acetic acid or another suitable acid.

In another embodiment of the invention Meldrum's acid derivative (A) is reacted in solution with imine (D) to form pyridinone (E). Preferably, Z comprises S or $SO_2$, n is 1, A comprises aryl m is O, D comprises aryl, $R_4$ comprises $CO_2Y$ wherein Y comprises hydrogen or alkyl. More preferably, Z comprises S, $R_1$ comprises oxo, n is 1, A comprises napthyl, m is O, D comprises phenyl, $R_4$ comprises $CO_2Y$ wherein Y comprises hydrogen.

The invention also includes embodiments where Y comprises alkyl, alkenyl, alkynyl, aryl, heteroaryl, substituted alkyl, substituted alkenyl, substituted alkynyl, substituted aryl or substituted heteroaryl. In those embodiments the process also comprises the further step of hydrolysis of the pyridinone. This hydrolysis can be accomplished in basic conditions through the use of a base such as NaOH or KOH, and is usually followed by acidic work-up with an acid such as acetic acid or another suitable acid.

Reaction Scheme I illustrates the general reaction to form a pyridinone of type (C). As shown in Reaction Scheme I, the Meldrum's acid derivative of formula (F) is reacted with the thiazoline of formula (G) to obtain the illustrative pyridinone of the invention, compound (H).

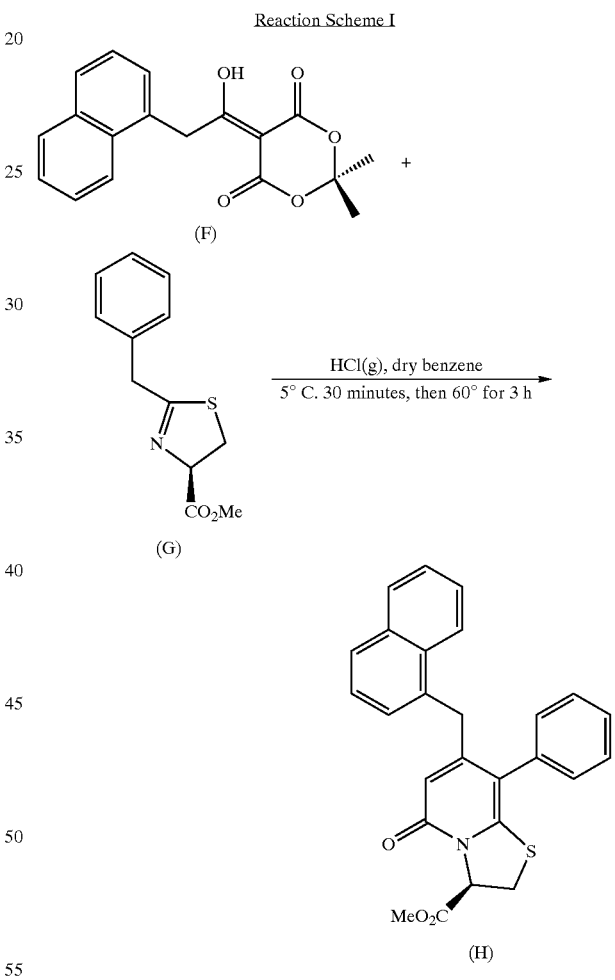

Reaction Scheme I

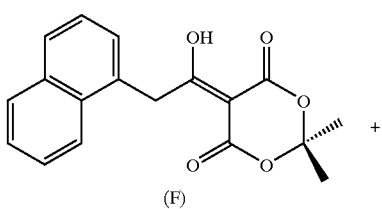

Reaction Scheme II

Reaction Scheme IV

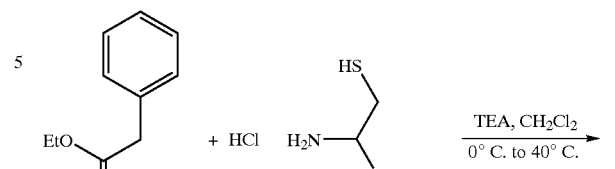

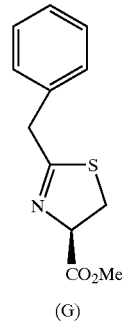

(G)

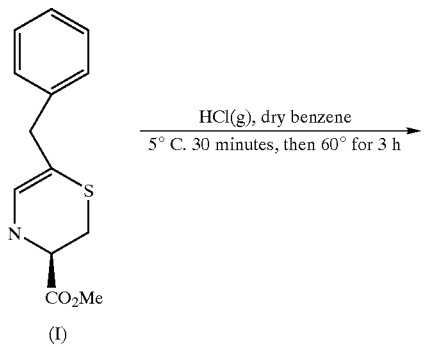

(I)

The thiazoline derivative of Reaction Scheme II is prepared as shown in Reaction Scheme V.

Reaction Scheme V

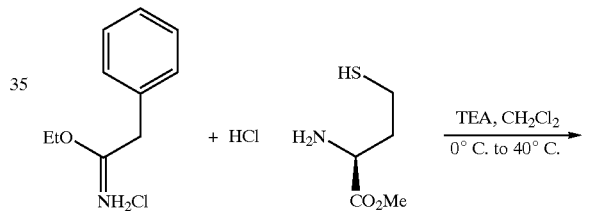

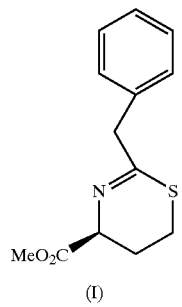

(I)

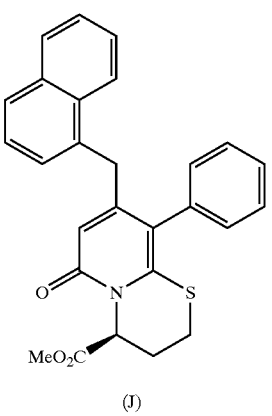

(J)

The Meldrum's acid derivative (F) of Reaction Schemes I and II is obtained by condensing an appropriate carboxylic acid with a Meldrum's acid as shown in Reaction Scheme III.

Reaction Scheme III

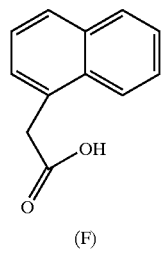

(F)

1) analytic chloride, benzene DMF (catalyllc amoual)
2) Meldrum's acid, DMF, CH₂Cl₂ 0° C. lo room temperature

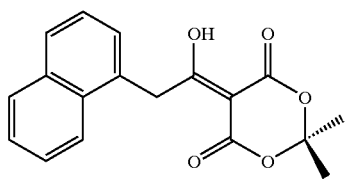

The thiazoline derivative of Reaction Scheme I is prepared as shown in Reaction Scheme IV.

The Meldrum's acid derivative (F) used in Reaction Schemes I and II was prepared as set forth in Reaction Scheme III. The Meldrum's acid derivative used in Reaction Schemes I and II was prepared using conditions similar to those for other Meldrum's acid derivatives described in Yamamoto, Y. et al. *Chem Pharm Bull* (1987) 35:1860–1870, which is herein incorporated by reference. The conditions set forth on page 1868 are most exemplary.

The thiazoline derivative (G) used in Reaction Scheme I was prepared as set forth in Reaction Scheme IV. This preparation is based on one described in Meyers, A. I.; Witten, C. E.; *Heterocycles,* 1976, 4:1687–1692, which is herein incorporated by reference. The hydrochloride salt of L-methyl cysteinate (L) was reacted with ethyl benzylimidate hydrochloride (K) using the conditions set forth on page 1688 of the Meyers reference. Specifically, L-methyl cysteinate (L) was dissolved in dichloromethane and treated with ethyl benzylimidate hydrochloride (K) in the presence of triethylamine. The reaction mixture was heated from 0° C. to 40° C. An alternative way of synthesizing thiazoline derivatives would be as described by Almqvist, F.; Guillaume, D.; Hultgren S. J.; Marshall, G. R. *Tetrahedron Lett.* 1998, 29:2293–2294, which is herein incorporated by reference.

The thiazoline derivative (I) used in Reaction Scheme II is prepared as set forth in Reaction Scheme V. This preparation is based on one described in Meyers, A. I.; Witten, C. E.; *Heterocycles,* 1976, 4:1687–1692, which is herein incorporated by reference. The hydrochloride salt of L-methyl homocysteinate (L) is reacted with ethyl benzylimidate hydrochloride (K) using the conditions set forth on page 1688 of the Meyers reference. Specifically, L-methyl cysteinate (L) is dissolved in dichloromethane and treated with ethyl benzylimidate hydrochloride (K) in the presence of triethylamine. The reaction mixture is heated from 0° C. to 40° C. An alternative way of synthesizing thiazoline derivatives would be as described by Almqvist, F.; Guillaume, D.; Hultgren S. J.; Marshall, G. R. *Tetrahedron Lett.* 1998, 29:2293–2294, which is herein incorporated by reference.

In a more detailed look at Reaction Scheme I, gaseous HCl was passed into an ice cold solution (5°–5° C.) of the Meldrum's acid derivative (F) containing the thiazoline derivative (G) in 30 ml of dry benzene until saturation. The resulting mixture was heated (2–4 hours) and then cooled to room temperature to form the illustrative pyridinone of the invention, compound (H).

In a more detailed look at Reaction Scheme II, gaseous HCl was passed into an ice to cold solution (5°–15° C.) of the Meldrum's acid derivative (F) containing the thiazoline derivative (I) in 30 ml of dry benzene until saturation. The resulting mixture was heated (2–4 hours) and then cooled to room temperature to form the illustrative pyridinone of the invention, compound (J).

In a preferred process for preparing a pyridinone of type (C) of the invention a Meldrum's acid derivative having the structure:

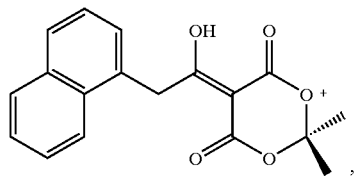

and thiazoline having the following structure:

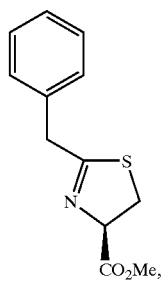

are dissolved in a solvent and cooled to 5°–15° C. A Lewis Acid is added to the mixture for 15–45 minutes and the mixture is heated for 2–4 hours at 50°–70° C. and then cooled to room temperature to form a pyridinone having the following structure:

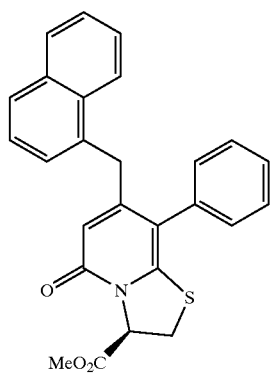

which is then hydrolyzed in basic conditions followed by acidic work-up to yield the following structure:

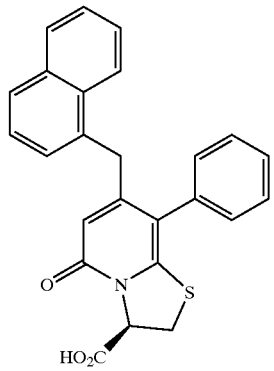

In a more preferred process for preparing a pyridinone of type (C) of the invention a Meldrum's acid derivative having the structure:

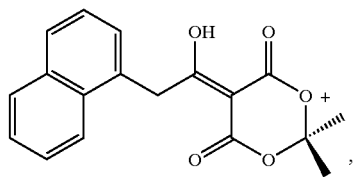

and thiazoline following structure:

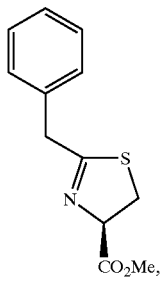

are dissolved in benzene and cooled to 5°–15° C. HCl gas is bubbled through the mixture for 15–45 minutes and the mixture is heated for 2–4 hours at 50°–70° C. and then cooled to room temperature to form a pyridinone having the following structure:

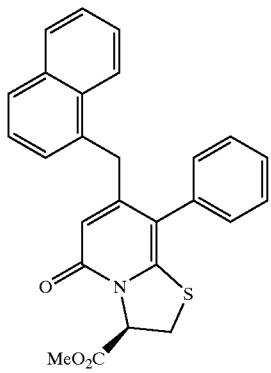

which is then hydrolyzed using sodium hydroxide followed by quenching with acetic acid to yield the following structure:

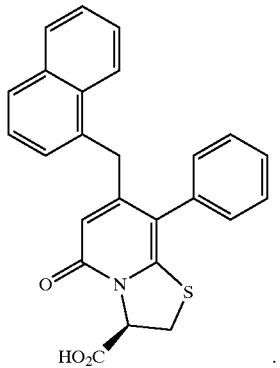

In a preferred process for preparing a pyridinone of type (E) of the invention a Meldrum's acid derivative having the structure:

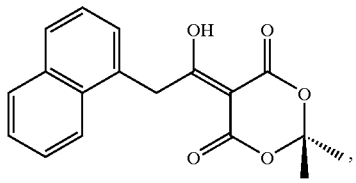

and thiazoline having the structure:

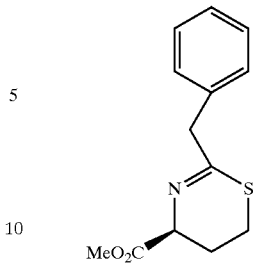

are dissolved in a solvent and cooled to 5°–15° C. A Lewis Acid is added to the mixture for 15–45 minutes and the mixture is heated for 2–4 hours at 50°–70° C. and then cooled to room temperature to form a novel pyridinone having the following structure:

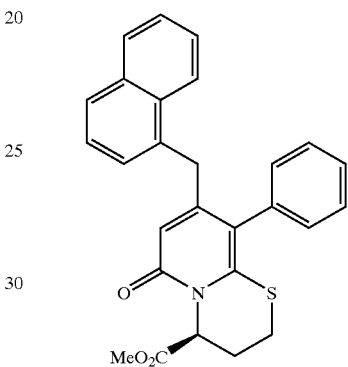

which is then hydrolyzed in basic conditions, followed by acidic work-up to yield the following structure:

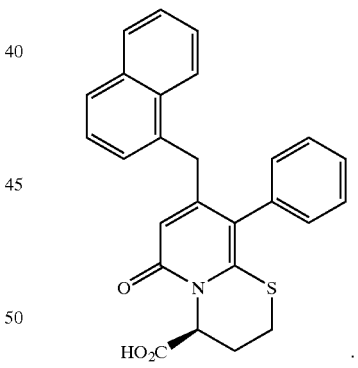

In a more preferred process for preparing a pyridinone of the invention a Meldrum's acid derivative having the structure:

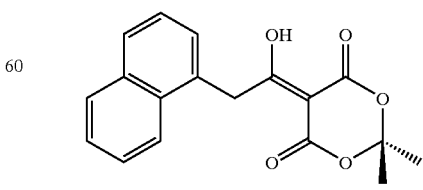

and thiazoline having the structure:

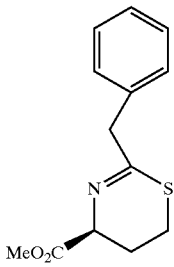

are dissolved in benzene and cooled to 5°–15° C. HCl gas is bubbled through the mixture for 15–45 minutes and the mixture is heated for 2–4 hours at 50°–70° C. and then cooled to room temperature to form a novel pyridinone having the following structure:

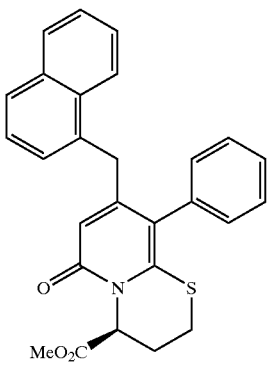

which is then hydrolyzed using sodium hydroxide, followed by quenching with acetic acid to yield the following structure:

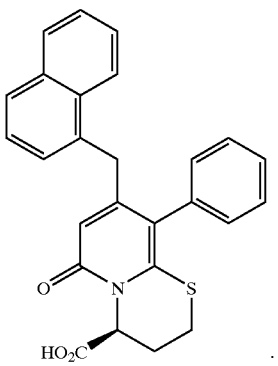

Solid Phase Synthesis of Pyridinones

The solid phase synthesis of pyridinones involves generally a process for the synthesis of ring fused 2-pyridinones on a solid support wherein an imine bound to a solid substrate is prepared and a Meldrum's acid derivative is added in acidic conditions.

Preferably the process for the synthesis of ring fused 2-pyridinones on a solid support, comprises the steps of: (a) coupling a protected amino acid to a solid support via an acid stable linker, (b) removing the protecting groups, (c) adding an iminoether to form an imine, and (d) adding a Meldrum's acid derivative in acidic conditions.

The solid support can be a resin such as a polystyrene resin or a functionalized polystyrene resin, such as a carboxypolystyrene resin, a tentagel S-bromide resin, or a PAM resin. Preferably the solid support is an acid stable resin. More preferably the solid support is an acid stable HMBA-AM resin.

The amino acid can be homocysteine or cysteine or could be prepared from serine or homoserine. Preferably the amino acid is cysteine. The amino acid can be protected by various protecting groups for amino acids. Preferably, the amino acid protecting group is an acid labile protecting group. Protecting groups for the amino group of the amino acid include but are not limited to t-butoxycarbonyl group (Boc), 2-(4-biphenylyl)propyl(2)oxycarbonyl (Bpoc), and 9-fluoroenylmethyloxycarbonyl (Fmoc). The preferred protecting group for the amino group is t-butoxycarbonyl group (Boc). Protecting groups for the thiol group of the amino acid include but are not limited to tert-butyl ($^t$Bu), acetamidomethyl (Acm), and triphenylmethyl(trityl) (Trt). The preferred protecting group for the thiol group is triphenylmethyl (trityl) (Trt). Most preferably, the protected amino acid is Boc-Cys(Trt)-OH.

The amino acid and the iminoether are reacted in acidic conditions, but once formed the ring fused 2-pyridinone is cleaved from the solid support by the addition of an appropriate base, such as NaOH or CeCO$_3$.

The iminoether of the solid phase synthesis has the following formula:

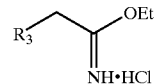

wherein $R_3$ comprises $(CH_2)_m D$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl.

The Meldrum's acid derivative of the solid phase synthesis has the following formula:

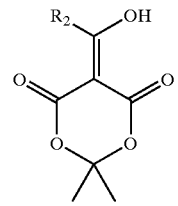

wherein $R_2$ comprises $(CH_2)_n A$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl.

The imine bound to a solid substrate has the following formula:

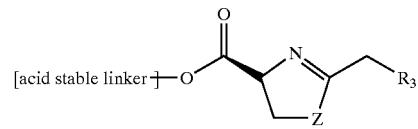

wherein Z comprises S, SO, SO$_2$, O, P, PO, PO$_2$, CH$_2$, or CR$_2$, $R_2$ comprises $(CH_2)_n A$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; and $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl.

The ring fused 2-pyridinones formed by the solid phase synthesis have the following formula:

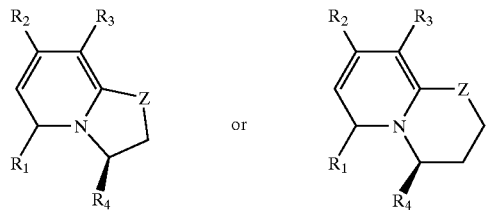

wherein $R_1$ comprises oxo; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2H$.

In the pyridinones prepared by the solid phase synthesis, preferably, n is 0, A comprises alkyl, m is 0 and D comprises aryl. More preferably, n is 0, A comprises methyl, m is 0 and D comprises phenyl.

In a more preferred embodiment of the solid phase synthesis the pyridinones are made by the following steps:

1) Attachment of Boc-Cys(Trt)-OH to acid stable HMBA-AM resin to give A

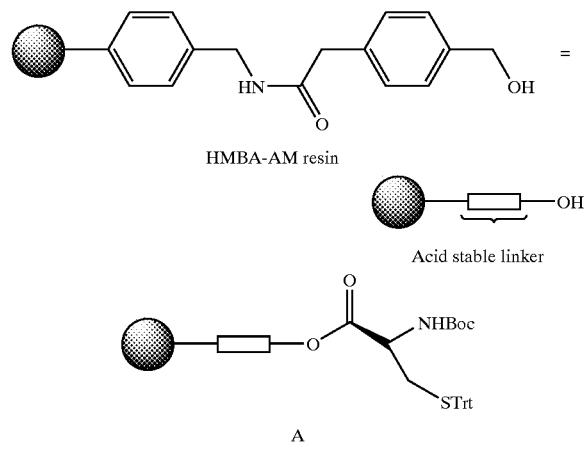

Boc-Cys(Trt)-OH was attached to acid stable HMBA-AM resin by combining Boc-Cys(Trt)-OH with MeIm and 1-(Mesitylene-2-sulfonyl)-3-nitro-1 H-1,2,4-triazole (MSNT) and agitating.

2) Deprotection of the acid labile protecting groups to give B

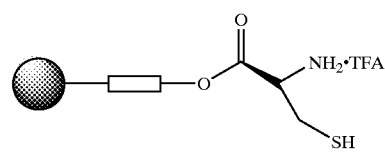

The acid labile protecting groups were removed by adding a mixture of TFA, thioanisol, and ethanedithiol followed by agitation.

3) Preparation of resin bound $\Delta^2$-thiazoline to give C

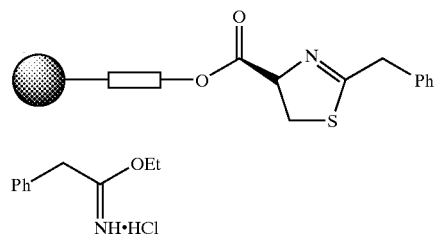

TEA and phenyliminoether were added, followed by additional TEA. The resin was then alternately rinsed with DMF and dichloromethane. This was followed by the addition of more phenyliminoether and TEA to yield the resin bound thiazoline.

4) Preparation of resin bound 2-pyridinone, E

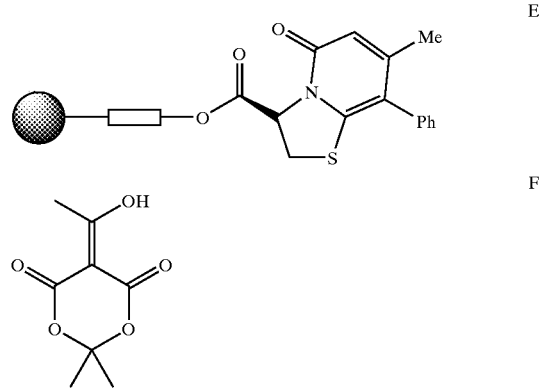

Meldrum's acid derivative was added followed by HCl-saturated benzene. This was followed by agitation of the mixture and washing of the resin. This sequence of steps was repeated several times to yield the resin bound 2-pyridinone.

5) Cleavage from the resin to give the 2-pyridinone G

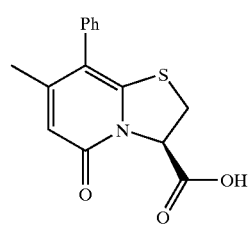

The desired pyridinone G was cleaved from the resin by the addition of NaOH and THF, followed by rinsing of the resin and acidification and purification of the filtrate.

Intermediates Useful in the Synthesis of Pyridinones Imine

The present invention is also directed to intermediates useful in the synthesis of the pyridinones and pyridinone derivatives of the invention. An imine of the formula below is provided:

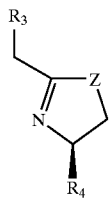

wherein Z comprises S, SO, $SO_2$, O, P, PO, $PO_2$, $CH_2$, or $CR_2$; $R_2$ comprises $(CH_2)_nA$ wherein n is a natural number between 0 and 5 and A comprises alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and when m is between 3 and 5, D comprises alkyl, alkenyl, alkynyl, aryl, heteroaryl, substituted alkyl, substituted alkenyl, substituted alkynyl, substituted aryl or substituted heteroaryl and when m is O, D comprises unsubstituted alkenyl, unsubstituted or substituted alkynyl, unsubstituted or substituted aryl, unsubstituted heteroaryl and when m is 1, D comprises unsubstituted alkyl, unsubstituted alkenyl, unsubstituted or substituted alkynyl, unsubstituted aryl, or substituted or unsubstituted heteroaryl and when m is 2, D comprises unsubstituted alkyl, unsubstituted or substituted alkenyl, unsubstituted or substituted alkynyl, unsubstituted aryl, or unsubstituted or unsubstituted aryl, or unsubstituted or substituted heteroaryl; $R_4$ comprises $CO_2G$, $B(OY)_2$, $CH_2OY$, $CH(CO_2Y)_2$, CHO, $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl and G comprises alkyl, alkenyl, alkynyl, aryl, heteroaryl, substituted alkyl, substituted alkenyl, substituted alkynyl, substituted aryl or substituted heteroaryl useful in the preparation of pyridinone (C) and pyridinone derivatives (N) and (Z) of the invention.

In a preferred embodiment of the invention, a thiazoline of the formula is provided:

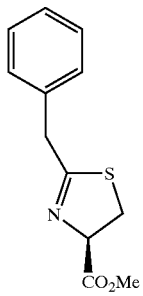

In an additional aspect of the invention an imine of the following formula is provided:

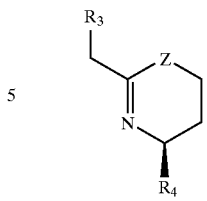

wherein Z comprises S, SO, $SO_2$, O, P, PO, $PO_2$, $CH_2$, or $CR_2$; $R_2$ comprises $(CH_2)_nA$ wherein n is a natural number between 0 and 5 and A comprises alkyl, alkenyl, alkynyl, aryl, heteroaryl, substituted alkyl, substituted alkenyl, substituted alkynyl, substituted aryl or substituted heteroaryl; $R_3$ $(CH_2)_mD$ wherein m is a natural number between 0 and 5 and when m is between 1 and 5, D comprises alkyl, alkenyl, alkynyl, aryl, heteroaryl, substituted alkyl, substituted alkenyl, substituted alkynyl, substituted aryl or substituted heteroaryl and when m is O, D comprises unsubstituted alkyl, substituted or unsubstituted alkenyl, substituted or unsubstituted alkynyl, substituted aryl, substituted or unsubstituted heteroaryl; $R_4$ comprises $CO_2J$, $B(OY)_2$, $CH(CO_2Y)_2$, $CH_2OY$, CHO, $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl and J comprises methyl, alkenyl, alkynyl, aryl, heteroaryl, substituted heteroaryl, substituted methyl, substituted alkenyl, substituted alkynyl, substituted aryl or substituted heteroaryl useful in the preparation of pyridinone (E) and pyridinone derivatives (O) and (AA) of the invention.

In a preferred embodiment of the invention, a thiazoline of the formula is provided:

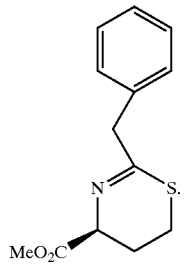

Derivatization of Pyridinones (C) And (E)

In an additional aspect of the invention pyridinone derivatives (N) and (O) can be prepared from pyridinones (C) and (E). Also preparable from pyridinones (C) and (E) are reduced pyridinone derivatives (Z) and (AA).

One of the embodiments of the present invention includes the halogenation of the pyridinone at the position designated as $R_5$ by reacting pyridinone (C) or (E) with a halogenating agent to form a halogen substituted pyridinone derivative. Such a reaction is illustrated with pyridinone (C) in Reaction Scheme VI. A similar result in Reaction Scheme VI can be obtained for pyridinone (E).

Reaction Scheme VI

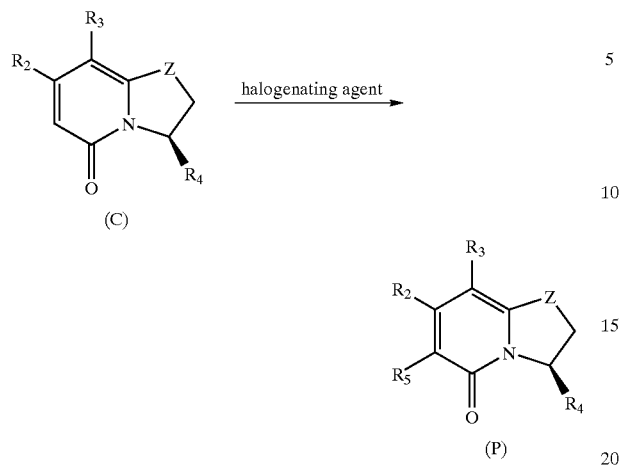

Reaction Scheme VII

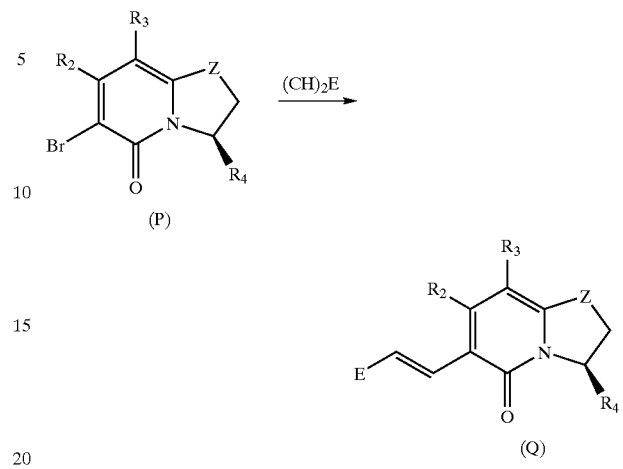

wherein Z comprises S, SO, $SO_2$, O, P, PO, $PO_2$, $CH_2$, or $CR_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; $R_4$ comprises $CO_2Y$, $B(OY)_2$, CHO, $CH_2OY$, $CH(CO_2Y)_2$, $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl; and $R_5$ comprises halogen.

Possible halogens include chlorine, fluorine, iodine, and bromine. Preferably, the halogen comprises bromine or iodine. Preferred halogenating agents include bromine and iodine monochloride. The bromination of pyridinone (C) at the position designated as $R_5$ can occur by the addition of $Br_2$ to a solution of pyridinone (C) in acetic acid and agitation at room temperature for 4 hours. The iodination of pyridinone (C) at the position designated as $R_5$ occurs by reacting pyridinone (C) with iodine monochloride by using a catalytic amount of ferrocenium tetrakis(3,5-bis (trifluoromethyl)phenyl)borate in the coexistence of DDQ or ZnO. This iodination reaction is illustrated by a procedure described by Mukaiyama, T., Kitigawa, H., Matsuo, J. *Tetrahedron Letters* 2000, 835–838, in their article describing aromatic iodination with iodine monochloride by using a catalytic amount of ferrocenium tetrakis(3,5-bis (trifluoromethyl)phenyl)borate, the entirety of which is hereby incorporated by reference. The authors specifically describe the direct iodination reaction of aromatic compounds with 1.1 to 2.0 molar amounts of ICl by using 5 mol % of $Cp_2FeB[3,5-(CF_3)_2C_6H_3]_4$ in the coexistence of DDQ or ZnO.

Halogen substituted pyridinone (P) can be further derivatized to possess different functionalities at $R_5$. As shown in Reaction Scheme VII a bromine substituted pyridinone derivative (P) can be further derivatized via an organometallic coupling to possess a conjugated ester, a conjugated ketone, a conjugated aldehyde, or a conjugated nitrile. A similar result in Reaction Scheme VII can be obtained for the corresponding derivative of pyridinone (E).

wherein Z, $R_2$, $R_3$, and $R_4$ are as defined in Reaction Scheme VI, E comprises COR, $CO_2R$, CHO, or CN and R comprises alkyl, alkenyl, alkynyl, aryl, heteroaryl, substituted alkyl, substituted alkenyl, substituted alkynyl, substituted aryl or substituted heteroaryl. Preferably, E comprises $CO_2R$ wherein R comprises aryl. More preferably, E comprises $CO_2R$ wherein R comprises benzyl. The organometallic coupling of $(CH)_2E$ to pyridinone derivative (P) is accomplished by heating $Pd(PPh_3)_2Cl_2$, $(CH)_2E$, pyridinone derivative (P) and triethylamine to reflux.

As shown in Reaction Scheme VIII a pyridinone derivative (P) can be reacted with a cyanating agent to yield nitrile substituted pyridinone derivative (R). A similar result in Reaction Scheme VIII can be obtained for the corresponding derivative of pyridinone (E).

Reaction Scheme VIII

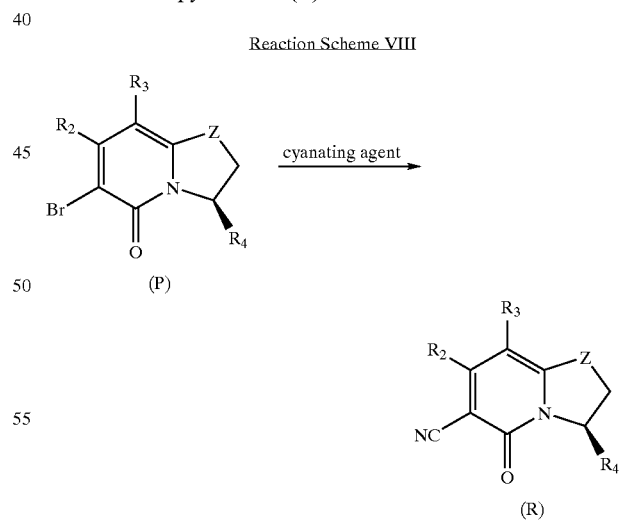

wherein Z, $R_2$, $R_3$, and $R_4$ are as defined in Reaction Scheme VI. Exemplary cyanating agents include but are not limited to CuCN and $(Zn)_2CN$. Pyridinone derivative (P) can be refluxed with CuCN in DMF for 16 hours. $FeCl_3$ in HCl is then added to the mixture to produce pyridinone (R) after extraction and purification.

Nitrile substituted pyridinone derivative (R) can be hydrolyzed to form pyridinone derivative (S) possessing a carboxylic acid functionality as shown in Reaction Scheme IX. A similar result in Reaction Scheme IX can be obtained for the corresponding derivative of pyridinone (E).

Reaction Scheme IX

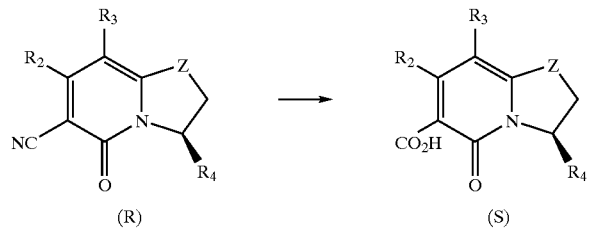

wherein Z, $R_2$, $R_3$, and $R_4$ are as defined in Reaction Scheme VI, however, of those pyridinone derivatives of (R) wherein $R_4$ is $CO_2Y$ and Y is substituted or unsubstituted alkyl, alkenyl, alkynyl, aryl, or heteroaryl, $R_4$ of (S) may be $CO_2Y$ wherein Y is hydrogen.

The hydrolysis is accomplished using potassium hydroxide in ethanol solvent. The preparation of pyridinone derivative (S) is illustrated by a procedure described by Reidlinger, G. H., Hans, J., *Synthesis* 1991, 835–838, in their article describing the use of cyanonitropropenides as synthons for the preparation of nitropyridines, the entirety of which is hereby incorporated by reference. The authors specifically describe the preparation of 6-amino-5-nitro-2-oxo-1,2-dihydropyridin-3-carboxylic acid from 6-amino-2-methoxy-5-nitropyridin-3-methylester by dissolving 6-amino-2-methoxy-5-nitropyridin-3-methylester in a solution of potassium hydroxide in water and ethanol and heating for 1.5 hours at 70 degrees Celcius. After that, the solution was cooled, acidified with 10% HCl to pH 2, solidified, crystallized, and isolated by suction to form 6-amino-5-nitro-2-oxo-1,2-dihydropyridin-3-carboxylic acid.

Pyridinone derivative (R) can be reduced to form pyridinone derivative (T) as shown in Reaction Scheme X. A similar result in Reaction Scheme X can be obtained for the corresponding derivative of pyridinone (E).

Reaction Scheme X

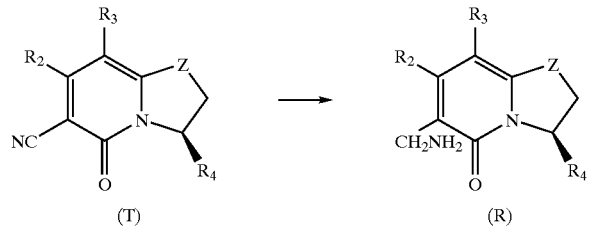

wherein Z, $R_2$, $R_3$, and $R_4$ are as defined in Reaction Scheme VI. The reduction of the nitrile substituted pyridinone derivative (R) is accomplished by combining $PtO_2$ and the nitrile substituted pyridinone in dry ethanol and adding $CHCl_3$. The combined reaction mixture is agitated under hydrogen pressure at room temperature for about 24 hours. The preparation of pyridinone derivative (T) is illustrated by a procedure described by Clive D. L. J., Hisaindee, S., *J. Org. Chem.* 2000, 65: 4923–4929 in their synthesis of racemic brevioxime and related model compounds, the entirety of which is hereby incorporated by reference. The authors describe the preparation of 3-[[Dimethyl(1,1-dimethylethyl)silyl]oxy]-4,4-dimethoxybutanamine Hydrochloride from 3-[[Dimethyl(1,1-dimethylethyl)silyl]oxy]-4,4-dimethoxybutanenitrile. A solution of 3-[[Dimethyl(1,1-dimethylethyl)silyl]oxy]-4,4-dimethoxybutanenitrile in dry ethanol was added to a suspension of Adam's catalyst in dry ethanol, followed by the addition of bench $CHCl_3$. The mixture was shaken under hydrogen at room temperature for 24 hours. The catalyst was filtered off and the filtrate was evaporated. The residue was kept under oil pump vacuum for 24 hours to give 3-[[Dimethyl(1,1-dimethylethyl)silyl]oxy]-4,4-dimethoxybutanamine.

Pyridinone derivative (R) can be further functionalized to form pyridinone derivative (U) possessing a tetrasol at $R_5$ as shown in Reaction Scheme XI. A similar result in Reaction Scheme XI can be obtained for the corresponding derivative of pyridinone (E).

Reaction Scheme XI

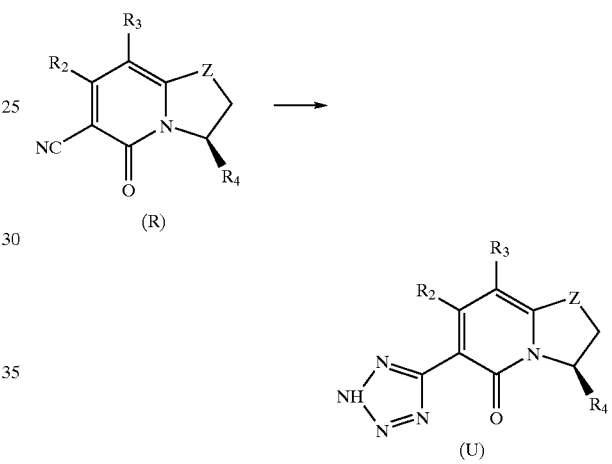

wherein Z, $R_2$, $R_3$, and $R_4$ are as defined in Reaction Scheme VI. The further transformation is accomplished by reacting the nitrile substituted pyridinone derivative with trimethylsilylazide and dibutyltin oxide in an organic solvent and heating the reaction mixture for 24–72 hours. Suitable organic solvents include toluene. The preparation of pyridinone derivative (U) in Reaction Scheme XI is illustrated by a procedure described by Wittenberger, S. J., and Donner B. G. *J. Org. Chem.* 1993, 58:4139–4141, the entirety of which is hereby incorporated by reference. The authors report a novel method for the preparation of 5-substituted tetrazoles from nitrites through the use of trimethylsilyl azide in the presence of catalytic dialkyltin oxide. In a typical procedure for the production of the 5-substituted tetrazoles, dibutyltin oxide was added to a solution of the nitrile and trimethylsilylazide dissolved in toluene. The resulting mixture was heated for 24–72 hours until the nitrile was consumed by the reaction. The reaction mixture was concentrated, extracted and filtered to yield the 5-substituted tetrazole.

Pyridinone derivative (P) can also be derivatized to pyridinone derivative (V) via organometallic coupling as shown in Reaction Scheme XII. A similar result in Reaction Scheme XII can be obtained for the corresponding derivative of pyridinone (E).

Reaction Scheme XII

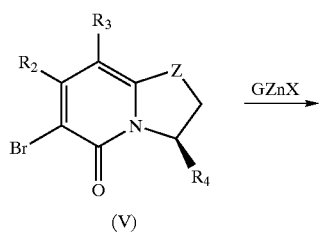

wherein Z, $R_2$, $R_3$, and $R_4$ are as defined in Reaction Scheme VI, G is aryl, alkyl, alkenyl, or alkynyl, and X is I, Br, or Cl. Examples of organozinc halide reagents include organozinc iodide and organozinc bromide. Examples of G, the organic component of the organozinc reagent, include but are not limited to the following compounds:

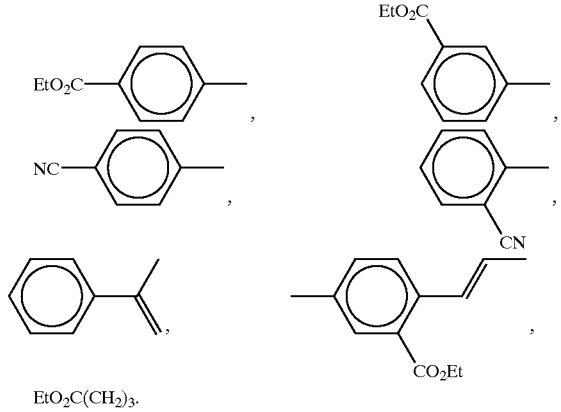

The organometallic coupling is accomplished by reacting the halogenated pyridinone derivative with an organozink halide and $Pd(PPh_3)_4$ in an organic solvent such as THF. The preparation of pyridinone derivative (V) in Reaction Scheme XII is illustrated by the reaction of organozinc compounds with aryl and vinyl halides described by Zhu L., Wehmeyer, R., and Rieke, R. *J. Org. Chem.* 1991, 56:1445–1453, the entirety of which is hereby incorporated by reference. The authors report that highly reactive zinc, prepared by the lithium naphthalenide reduction of $ZnCl_2$, readily undergoes oxidative addition to aryl halides under mild conditions to generate the corresponding organozinc compounds in excellent yields. The authors noted that the reaction is tolerant to a wide variety of functional groups on the aryl halides, indicating the broad applicability of the procedure. In a typical procedure for the reaction of GZnX with aryl halides the authors describe the addition of the GZnI reagent in THF solvent via cannula to a solution of 5 mol % $Pd(PPh_3)$ and the aryl halide at room temperature under an argon atmosphere. The solution is stirred for 3 hours and then worked up. The work-up procedure involves pouring the solution into a saturated $NH_4Cl$ aqueous solution and extracting with diethylether. The combined organic layers can be dried over anhydrous $CaCl_2$ and purified by flash chromatography.

Pyridinone derivative (P) can also be derivatized to form pyridinone derivative (W) by the organometallic coupling of (trimethylsilyl)acetylene as shown in Reaction Scheme XIII. A similar result in Reaction Scheme XIII can be obtained for the corresponding derivative of pyridinone (E).

Reaction Scheme XIII

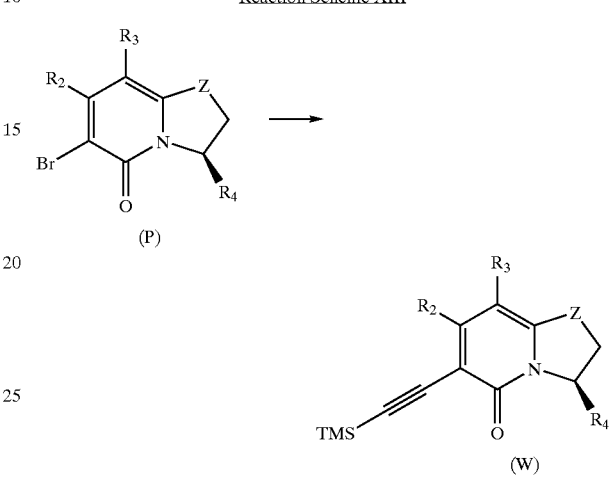

wherein Z, $R_2$, $R_3$, and $R_4$ are as defined in Reaction Scheme VI. Reagents for the organometallic coupling include $PdCl_2(PPh_3)_2$ and CuI or other suitable organometallic reagents. The organometallic coupling is accomplished by combining the halogenated pyridinone derivative with (trimethylsilyl)acetylene and triphenylphosphine, $PdCl_2(PPh_3)_2$ and CuI and then heating at 120 degrees Celcius for 72 hours. The preparation of pyridinone derivative (W) is illustrated by a procedure described by Padwa A., Sheehan S. M., and Straub C. S., *J. Org. Chem.* 1999, 64: 8648–8659 for an isomunchnone-based method for the synthesis of highly substituted 2(1H)-pyridones, the entirety of which is hereby incorporated by reference. The authors describe the palladium catalyzed coupling of (trimethylsilyl)acetylene with a triflate to provide a (trimethylsilyl)acetylene substituted compound. The specific preparation procedure employed by the authors involved the addition of CuI, followed by $PdCl_2(PPh_3)_2$ to a solution containing triphenylphosphine in triethylamine. To this solution was added (trimethylsilyl)acetylene in toluene followed by the addition of trifluoromethanesulfonic acid 8-phenylsulfonyl-5-oxo-1,2,3,5-tetrahydroindolizin-6-yl ester. The mixture was heated at 115 degrees Celcius for 1 hour, cooled to room temperature, poured into ice water, extracted with $CH_2Cl_2$, washed with brine, and dried over $Na_2SO_4$. The organic extracts were filtered and concentrated under reduced pressure. The crude residue was subjected to flash silica gel chromatography to yield 8-phenylsulfonyl-6-trimethylsilanylethynyl-2,3-dihydro-1H-indolizin-5-one.

Pyridinone derivative (P) can also be derivatized to form lactam substituted pyridinone derivative (X) by organometallic coupling as shown in Reaction Scheme XIV. A similar result in Reaction Scheme XIV can be obtained for the corresponding derivative of pyridinone (E).

Reaction Scheme XIV

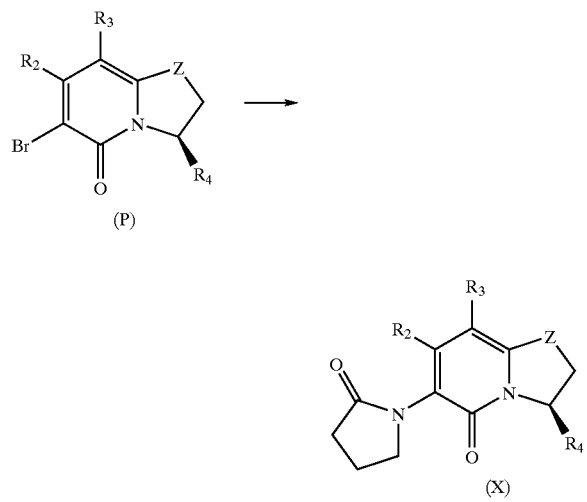

wherein Z, $R_2$, $R_3$, and $R_4$ are as defined in Reaction Scheme VI. Reagents for the organometallic coupling include palladium compounds or other appropriate organometallic reagents. Preferred reagents for the organometallic coupling include palladium acetate(II). The organometallic coupling is accomplished by heating the halogenated pyridinone derivative with palladium acetate(II), 1,1'-bis(diphenylphosphino)-ferrocene, sodium tert-butoxide, and a lactam in an organic solvent such as toluene under an inert atmosphere for around 48 hours. The preparation of pyridinone derivative (X) is illustrated by a procedure described by Shakespeare W., Tetrahedron Letters 1999, 40: 2035–2038 for the palladium-catalyzed coupling of lactams with bromobenzenes, the entirety of which is hereby incorporated by reference. The author describes the preparation of 1-phenyl-pyrrolidin-2-one by combining palladium acetate (II), 1,1'-bis(diphenylphosphino)-ferrocene (DPPF), sodium tert-butoxide, a lactam, and a bromobenzene in toluene and heating in a sealed tube for 48 hours. After filtration and concentration, flash chromatography yielded the desired 1-phenyl-pyrrolidin-2-one.

As shown in Reaction Scheme XV pyridinone (C) is reacted with a nitrating agent to yield nitrated pyridinone derivative (Y). A similar result in Reaction Scheme XV can be obtained for pyridinone (E).

Reaction Scheme XV

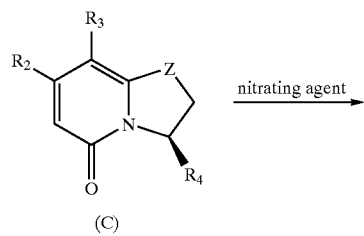

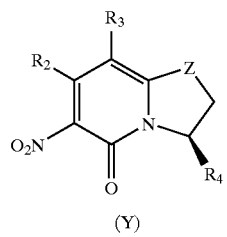

wherein Z, $R_2$, $R_3$, and $R_4$ are as defined in Reaction Scheme VI. Exemplary nitrating agents include but are not limited to nitric acid in a suitable solvent, such as acetic acid or acetic anhydride. Preferred nitrating agents include nitric acid dissolved in acetic anhydride. The preparation of pyridinone derivative (Y) is accomplished by reacting pyridinone (C) with nitric acid and acetic anhydride. The preparation of pyridinone derivative (Y) is illustrated by a procedure described by Barker A., and Barker C., J. Org. Chem. 1954, 2034: 870–872 for the preparation of 7-diamino-3:6-dinitrofluorene, the entirety of which is hereby incorporated by reference. In the reference the authors also describe the specific procedure for the preparation of 2:7-diacetamido-3:6-dinitrofluorene. 2:7-Diacetamidofluorene is added to a stirred mixture of nitric acid and acetic anhydride over a 10 minute period of time. After 2 additional minutes the solution was poured into ice-water, the solid was removed, washed until it was acid-free and dried. Following extraction with hot acetic acid to remove material which inhibited crystallization, crystallization from nitrobenzene yielded 2:7-diacetamido-3:6-dinitrofluorene.

As shown in Reaction Scheme XVI pyridinone (C) is reduced to yield pyridinone derivative (Z). A similar result in Reaction Scheme XVI can be obtained for pyridinone (E).

Reaction Scheme XVI

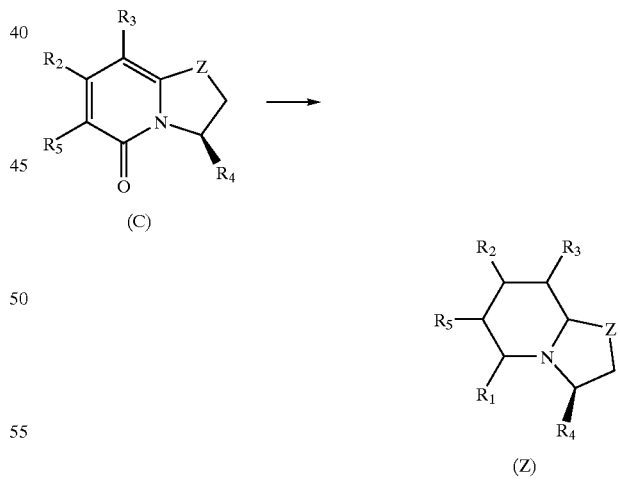

wherein Z comprises S, SO, $SO_2$, O, P, PO, $PO_2$, $8CH_2$, or $CR_2$; $R_1$ comprises oxo; $R_2$ comprises $(CH_2)_n A$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_m D$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, $CHO$, $CH_2OY$, $CH(CO_2Y)_2$, $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl; and $R_5$ is hydrogen, halogen, nitrile, $NO_2$, $CO_2H$, $CH_2NH_2$, cyclic $CHN_4$, a lactam, $NO_2$, (trimethylsilyl)acetylene, G wherein G comprises alkyl, alkenyl, alkynyl, aryl, substituted alkyl, substituted alkenyl, substituted alkynyl, substituted aryl, or $(CH)_2E$ wherein E comprises COR, $CO_2R$, CHO, or CN and R comprises alkyl, alkenyl, alkynyl, aryl, heteroaryl, substituted alkyl, substituted alkenyl, substituted alkynyl, substituted aryl or substituted heteroaryl.

The reduction is accomplished by adding a catalytic amount of $PtO_2$ to a solution of the pyridinone in acetic acid and stirring under a hydrogen atmosphere of 90 psi for 2 hours. Reduction of aromatic moieties in the $R_2$, $R_3$ and $R_5$ substituents is expected to result from the reduction procedure. The preparation of pyridinone derivative (Z) is illustrated by a procedure described by Padwa A., Sheehan S. M., and Straub C. S., *J. Org. Chem.* 1999, 64: 8648–8659 for an isomunchnone-based method for the synthesis of highly substituted 2(1H)-pyridones, the entirety of which is hereby incorporated by reference. The authors describe the preparation of 5-oxoindolizidine from 2,3-dihydro-5(1H)-indolizinone. The specific preparation procedure employed by the authors involved the addition of a catalytic amount of $PtO_2$ to a solution of 2,3-dihydro-5(1H)-indolizinone in acetic acid. The reaction mixture was stirred under a hydrogen atmosphere of 90 degrees psi for 2 hours. The organic layer was washed with brine, dried over $NaSO_4$ and concentrated under reduced pressure. The crude residue was subjected to flash silica gel chromatography to yield 5-oxoindolizidine.

Pyridinone derivatives (P) and (Y) are preparable from pyridinone (C) according to Reaction Scheme VI and Reaction Scheme XV, respectively. Furthermore, pyridinone derivatives (Q), (R), (V), (W) or (X) can be prepared from pyridinone derivative (P) according to the reaction schemes described above. Thus, any of pyridinone derivatives (Q), (R), (V), (W) or (X) can be prepared from an imine and a Meldrum's acid derivative via either the synthesis in solution or the solid phase synthesis of pyridinone (C) and derivatization of pyridinone (C) to pyridinone derivative (P). Furthermore, any of pyridinone derivatives (S), (T), and (U) can be prepared from pyridinone derivative (P) via the further derivatization of pyridinone derivative (R). Therefore, each of pyridinone derivatives (S), (T), and (U) are also preparable from an imine and a Meldrum's acid derivative via either the synthesis in solution or the solid phase synthesis of pyridinone (C) and derivatization of pyridinone (C) to pyridinone derivative (P). Similar results in the above reaction schemes can be obtained for pyridinone (E) and the corresponding derivatives of pyridinone (E).

Compositions Containing the Pyridinones and Methods of Use

The present invention further provides antibacterial compositions, including pharmaceutical compositions containing these compounds, and methods to inhibit or prevent bacterial growth using the compounds of the invention as well as antibodies specific for them. The compounds of the invention are effective in inhibiting a variety of Gram-negative bacteria. They can be employed in disinfectant compositions and as preservatives for a wide variety of materials that possess nutrients for bacterial organisms such as foodstuffs, cosmetics, and medicaments. For use in these contexts the compounds in the invention are supplied either as a single compound, in a mixture with several other compounds of the invention or in a mixture with additional antimicrobial agents. These compounds generally act as preservatives and are therefore usually present in amounts of less than 5% by weight of the total composition, more preferably less than 1%, still more preferably less than 0.1%.

In their use as antimicrobials for the treatment of animal subjects, the compounds of the invention can be formulated as pharmaceutical or veterinary compositions. The compounds are formulated in ways consistent with the mode of administration, the subject to be treated, and the type of treatment desired, for example prevention, prophylaxis, therapy. A summary of these techniques is provided in Remington's Pharmaceutical Sciences, latest edition, Mack Publishing Co., Easton, Pa.

In general, for use in treatment the compounds of the invention may be used alone or in combination with antibiotics such as erythromycin, tetracycline, and macrolides such as azithromycin and cephalosporins. Particular formulations of the compounds will vary formulated depending on the method by which they are to be administered to the affected areas.

Formulations may be prepared in a manner suitable for systemic administration or topical or local administration. Systemic formulations include those designed for injection (e.g. intramuscular, intravenous or subcutaneous injection) or may be prepared for transdermal, transmucosal or oral administration. The formulation will generally include a diluent as well as, in some instances, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include water, saline, dextrose, glycerol and the like. These compositions may also contain amounts of nontoxic auxiliary substances such as wetting or emulsifying agents, pH buffering agents such as sodium acetate and sorbitan monolaurate.

Additionally, various sustained release systems for drugs have also been devised such as in U.S. Pat. No. 5,624,677, for example.

Other forms of administration that may be employed include suppositories, transdermal patches, oral, transmucosal and intranasal administration. Such forms of administration tend to be more noninvasive methods. Suitable dosage forms for oral use include tablets, dispersable powders, granules, capsules, suspensions, syrups, and elixers. Inert diluents and carriers for tablets include, for example, calcium carbonate, sodium carbonate, lactose and talc. Tablets may also contain granulating and disintegrating agents such as starch and alginic acid, binding agents such as starch, gelatin and acacia, and lubricating agents such as magnesium stearate, stearic acid and talc. Tablets may be uncoated or may be coated by unknown techniques; e.g., to delay disintegration and absorption. Inert diluents and carriers which may be used in capsules include, for example, calcium carbonate, calcium phosphate and kaolin. Suspensions, syrups and elixers may contain conventional excipients, for example, methyl cellulose, tragacanth, sodium alginate; wetting agents, such as lecithin and polyoxyethylene stearate; and preservatives, e.g. ethyl-p-hydroxybenzoate.

The invention also includes a pharmaceutical composition containing the pyridinone, its derivatives or the salts thereof and one or more pharmacologically acceptable, inert or physiologically active diluents or adjuvants. With animal or human subjects an effective amount of the compounds of the invention is that amount sufficient to inhibit pilus assembly in Gram-negative bacteria and thus to prevent or treat infection by such Gram-negative bacteria. This effective amount is typically a dosage of 0.1–100 mg/kg. However, dosage levels vary considerably depending on the nature of the infection, the condition of the patient and the frequency and method of administration. With respect to administration to an environment or object, an effective amount is considered to be that amount which inhibits pilus formation in Gram-negative bacteria and thus prevents bacterial colonization in that environment or surface. This amount will vary depending on the nature of the environment or surface.

Antibodies

Antibodies to the compounds of the invention may also be produced using standard immunological techniques for production of polyclonal antisera and, if desired, saving the antibody-producing cells of the immunized host for sources of monoclonal antibody production. Techniques for producing antibodies to any substance of interest are well known. The immunogenicity of the substance may be enhanced by coupling the hapten to a carrier. Carriers useful for this purpose include substances which do not themselves elicit an immune response in the subject mammal. Common carriers used include keyhole limpet hemocyanin (KLH) diptheria taxoid, serum albumin, and the viral coat protein of rotavirus, VP6. Coupling the hapten to the carrier is effected by standard techniques such as contacting the carrier with the peptide in the presence of a dehydrating agent such as dicyclohexylcarbodiimide or through the use of linkers.

The compounds of the invention in immunogenic form are then injected into a suitable mammalian host and antibody titers in the serum are monitored.

Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies. The genes encoding monoclonal antibodies secreted by selected hybridomas or other cells may be recovered, manipulated if desired, for example, to provide multiple epitope specificity or to encode a single-chain form and may be engineered for expression in alternative host cells.

The present invention includes antibodies specifically immunoreactive with the pyridinones and pyridinone derivatives of the present invention. Such antibodies can be used in immunoassays for the qualitative and quantitative detection of varying types of analytes of interest, such as antigens or hormones.

Computer Modeling

The binding affinity of the following compound:

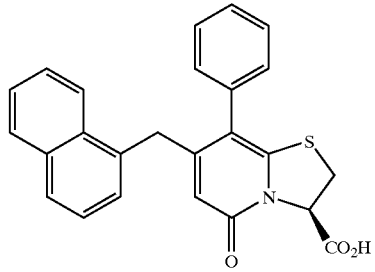

for the chaperone PapD has been validated by computer modeling using the program Validate described in Head, R.; Smythe, M.; Oprea, T.; Waller, C.; Green, S.; Marshall, G. J. Am. Chem. Soc. 1996, 118:3959–3969, which is herein incorporated by reference. The scores are $-\log K_i = 7.39$.

Screening Assays

Relevant assays into which the compounds of the invention can be screened include antichaperone or antimicrobial assays. The compounds are further characterized according to chemical identity and purity using conventional techniques. The assay can be scored on a real-time basis and further modifications made accordingly. Antichaperone binding activity can be measured by any number of direct methods such as monitoring spectral changes in the compound and/or chaperone, or determining the extent of compound binding to immobilized chaperone or vice versa, or by indirect methods such as competition assays to determine the extent to which these compounds inhibit chaperone binding to target pilus subunits and/or derivative (Soto, et al., Embo J., (1998) 17:6155; Karlsson et al., Bioorg Med Chem. (1998) 6:2085)) and/or synthetic peptides corresponding to subunit fragments known to bind chaperones (Kuehn, et al., Science, (1993) 262:1234).

Assays to determine the extent of pilus expression in the presence of these compounds may be performed as described in Soto et al., supra, and/or by haemagglutination assays as described in Striker et al., Mol Microbiol, (1996) 16:1021.

Assays of inhibition of bacterial binding to target tissues in the presence of these compounds would be performed as described in Striker, et al., supra.

Conventional techniques, e.g., radial diffusion method against E. coli ML-35P, L. monocytogens Strain EGD and yeast phase C. albican, may be used to evaluate the spectra of the antimicrobial activity for the novel N-substituted pyridinone compounds of the present invention.

A Reconstitution Assay was performed to obtain the percentages of inhibition found in the table below. In this Reconstitution Assay various amounts of inhibitor were added to the chaperone and FimH and they were allowed to competitively inhibit, and the resulting material was run on a cation exchange column. The resulting peak areas were compared to that of a control to determine the percentages of inhibition. This is accomplished by taking a chaperone adhesin complex such as a FimC-FimH complex and separating it by incubating it in 3 molar urea. It is then put over a cation exchange column to isolate FimH. The isolated FimH is then mixed with free FimC and run over an ion exchange column to produce a peak corresponding to the concentration of the resulting reconstituted FimC-FimH complex. The same procedure is followed in the presence of the subject compound being tested and the reduction of resulting peak area is correlated to the percentage of inhibition. The Reconstitution Assay is applicable to any chaperone adhesin complex or chaperone pilin complex.

The following procedures were employed. The subject compound (inhibitor tested as identified below) was mixed with chaperone at room temperature for 15 minutes. FimH and MES buffer (2-(4-morpholino)-ethane sulfonic acid) were added and the resulting mixture was mixed for 15 minutes at room temperature. The final mixture was then placed on a cation exchange column. The concentration of FimH used was 1 mg/ml of FimH in MES buffer. The concentration of FimC used was 12 mg/ml of FimC in MES buffer. FimC and FimH were in a 1 to 1 molar ratio in this assay. The various inhibitor to FimC ratios and inhibitor to PapD ratios employed in the assay are shown in the table below. It is recognized that varying the above concentrations and conditions may result in different percent inhibition values. concentrations and conditions may result in different percent inhibition values.

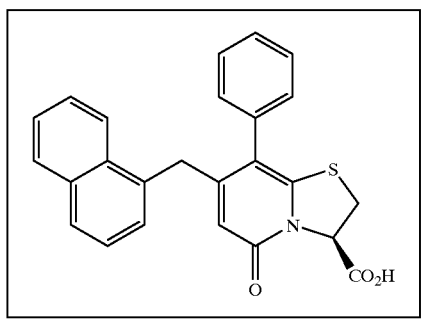

| Inhibitor/PapD ratio | % Inhibition |
| --- | --- |
| 36 | 67 |
| 54 | 82 |

| Inhibitor/FimC ratio | % Inhibition |
| --- | --- |
| 6 | 20 |
| 24 | 42 |
| 100 | 100 |

The following examples are intended to illustrate but not to limit the invention.

EXAMPLE 1

Synthesis of Pyridinone Methyl Ester

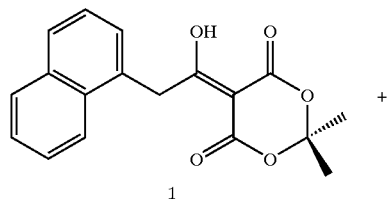

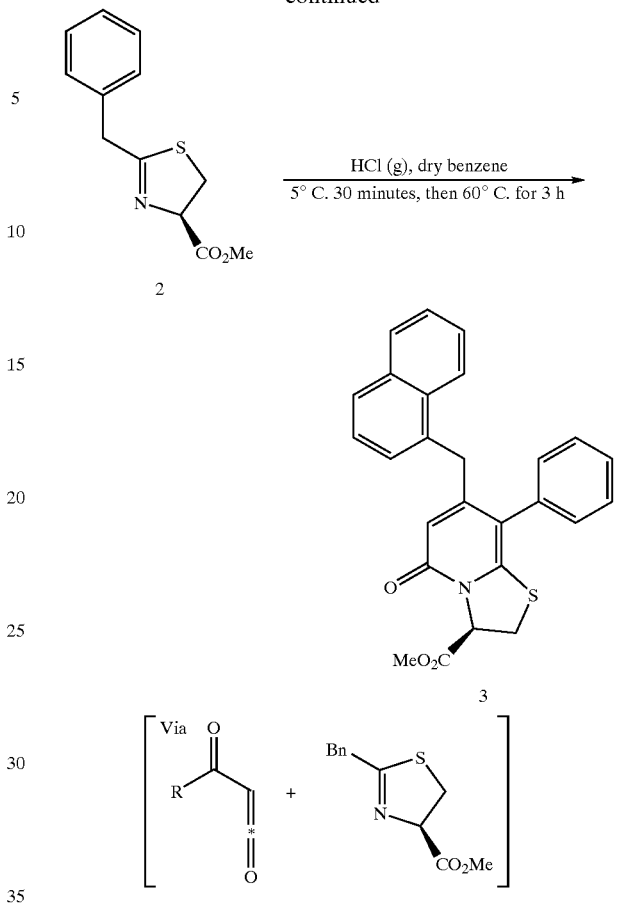

(3R)-7-(Naphthalen-1-ylmethyl)-5oxo-8-phenyl-2,3,-dihydro-5H-thiazolo(3,2-[α])pyridine-3-carboxylic acid methyl ester, 3. Meldrum's acid derivative 1 (1598 mg, 5.12 mmol) and thiazoline 2 (847 mg, 3.6 mmol) were dissolved in dry benzene (50 mL) and cooled to 5°–15° C. HCl gas was bubbled through the mixture for 15–45 minutes. The resulting turbid mixture was heated for 2–4 hours at 50°–70° C. and then cooled to room temperature. The resulting mixture was diluted with ethyl acetate and washed with water. The water phase was re extracted twice with $CH_2Cl_2$ and the combined organic extracts were dried ($Na_2SO_4$). Purification by silica gel chromatography (heptane:ethyl acetate, 50:50–10:90) gave pyridinone 3 as a white foam (470 mg, 53% yield from thiazoline 2). $[a]_D$ −12.8° (c 0.76, $CHCl_3$); IR λ 3041, 2953, 1753, 1655, 1581, 1485, 793 $cm^{-1}$; $^1H$ NMR (400 MHZ, $CDCl_3$) d 7.82 (dd, J 7.18, 2.13 Hz, 1H) 7.73 (d, J 8.25 Hz, 1H) 7.62 (dd, J 7.17, 1.82 Hz, 1H) 7.45–7.34 (m, 8H) 7.21 (d, J 6.82 Hz, 1H) 5.82 (s, 1H) 5.60 (dd, J 8.52, 2.39 Hz, 1H) 3.97 (dd, J 39.92, 17.22 Hz, 2H) 3.80 (s, 3H) 3.65 (dd, J 11.78, 8.57 Hz, 1H) 3.45 (dd, J 11.75, 2.43 Hz, 1H); $^{13}C$ NMR (100 MHZ, $CDCl_3$) d 168.5, 161.2, 154.3, 146.4, 136.3, 133.9, 133.7, 131.7, 130.2(broad), 129.7(broad), 129.0(splitted), 128.7, 128.4, 127.9, 127.6, 126.0, 125.6, 125.4, 123.7, 116.1, 115.2, 63.4, 53.2, 36.9, 31.6; HRMS (FAB+) Calcd. for $C_{26}H_{21}NO_3S$ 427.1242 Observed 427.1228.

EXAMPLE 2

Synthesis of Pyridinone Carboxylic Acid

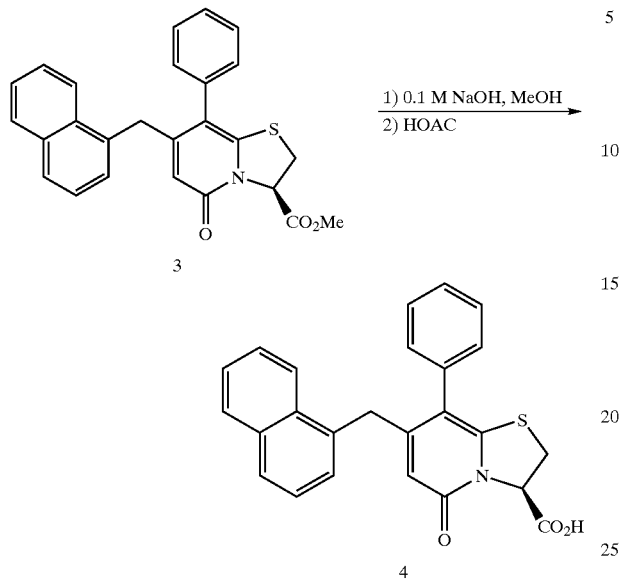

(3R)-7-(Naphthalen-1-ylmethyl)-5-oxo-8-phenyl-2,3-dihydro-5H-thiazolo(3,2-[α])1, 4. NaOH (0.1 M, 13 mL) was added dropwise to a solution of 3 (545 mg, 1.28 mmol) in MeOH (38 mL) at room temperature. After stirring for 17 hours the mixture was evaporated and the residue was dissolved in HOAc. The solution was transferred to a test tube and water was added at which the product precipitated. After centrifugation the liquid was removed and the residue was washed once with water. Freeze drying from Water/HOAc (8:2) gave pure 4 (487 mg, 92%) as a white powder. [a]$_D$–16.7° (c 0.33, dioxane:MeOH, 5:1); IR 1 cm$^{-1}$ 3610–3114 (broad), 2972, 2893, 1726, 1616, 1537, 1483, 1441, 1192, 781, 702; $^1$H NMR (400 MHZ, CDCl$_3$) d 10.20 (s, broad, 1H) 7.72 (d, J 7.17 Hz, 1H) 7.58 (dd, J 18.32, 7.57 Hz, 2H) 7.38–7.17 (m, 9H) 7.06 (s,1H) 5.72 (s, 1H) 5.28 (s, 1H) 3.93 (d, J 16.51 Hz, 1H) 3.74 (d, J 16.0 Hz, 1H) 3.51 (s, 1H) 3.16 (s, 1H); $^{13}$C NMR (100 MHZ, CDCl$_3$) d 168.4, 159.8, 152.3, 147.8, 136.2, 134.0, 133.0, 130.9, 129.8 (broad, splitted), 128.5, 128.2, 127.7. 127.3, 127.0, 126.0, 125.4, 125.2, 123.5, 113.8, 113.2, 64.5, 35.5, 31.8; HRMS (FAB+) calcd. for $C_{20}H_{18}NO_3S$ 352.1005 Observed 352.1007.

EXAMPLE 3

Synthesis of Pyridinone Sulfone Methyl Ester

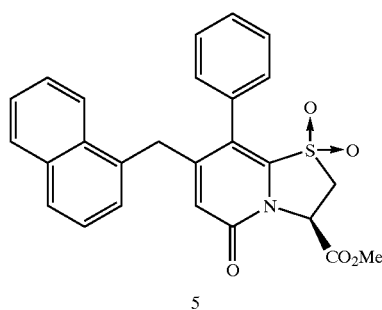

(3R)-7-(Naphthalen-1-ylmethyl)-1,1,5-trioxo-8-phenyl-1,2,3,5-tetrahydro-1λ$^6$-thiazolo(3,2-[α])pyridine-3-carboxylic acid methyl ester, 5. A solution of MCPBA (744 mg, 4.31 mmol) in CH$_2$Cl$_2$ (34 mL) was added dropwise to a solution of 3 in CH$_2$Cl$_2$ (24 mL) at –78° C. The mixture was kept at –78° C. for one hour and then the cooling bath was removed. After stirring overnight the mixture was diluted with CH$_2$Cl$_2$ and then ice was added. The organic phase was washed several times with NaHCO$_3$ (sat, aq), the combined water was re extracted with CH$_2$Cl$_2$ twice and then the organic phases were combined and dried (Na$_2$SO$_4$ aq free). Concentration at reduced pressure followed by flash chromatography (SiO$_2$, heptane:ethyl acetate, 1:1®1:3) gave pure5 (317 mg, 80%). [a]$_D$–1.7° (c 2.74, CHCl$_3$); IR λ, 3010, 2953, 1751, 1664, 1593, 1336, 1213, 1134, 748, 700 cm$^{-1}$; $^1$H NMR (400 MHZ, CDCl3) δ 7.86 (dd, J 6.30, 2.16 Hz, 1H) 7.79 (d, J 8.21 Hz, 1H) 7.60–7.38 (9 H) 7.23 (m, 1H) 6.20 (s, 1H) 5.48 (dd, J 8.67, 2.75 Hz, 1H) 4.10 (d, J 17.38, 1H) 3.95 (d, J 17.76, 1H) 3.81 (s, 3H) 3.76 (dd, J 16.65, 2.77 Hz, 1H) 3.68 (dd, J 13.67, 8.75 Hz, 1H) $^{13}$C NMR (100 MHZ, CDCl3) δ 166.5, 158.8, 155.6, 137.8, 134.0, 132.5, 131.4, 130.7, 129.9, 129.5,129.3, 129.0, 128.9, 128.6, 128.20, 128.16, 126.5, 125.8, 125.5, 123.4, 123.1, 119.4, 53.8, 52.4, 51.6, 36.7; HRMS (FAB+) calcd. for $C_{26}H_{22}NO_5S$ 460.1219 Observed 460.1227.

EXAMPLE 4

Synthesis of Pyridinone Sulfone Carboxylic Acid

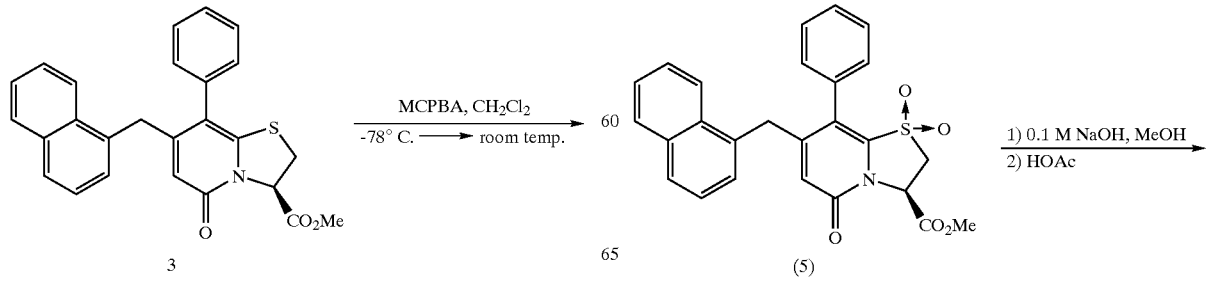

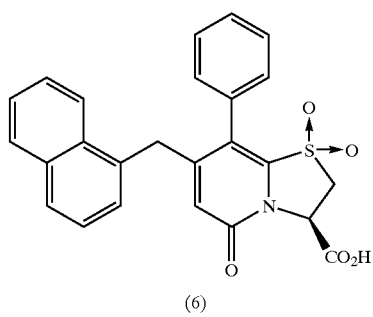

(6)

(3R)-7-(Naphthalen-1-ylmethyl)-1,1,5-trioxo-8-phenyl-1,2,3,5-tetrahydro-1λ-thiazolo(3,2-[α])pyridine-3-carboxylic acid, 6. By following the procedure described for the preparation of 4 from 3, 5 (160 mg, 0.35 mmol) gave 6 (126 mg, 81%). $[a]_D 1.0°$ (c 0.70, dioxane:MeOH, 5:1); IR 1, 3055, 3022, 2962, 2902, 2681–2144 (broad), 1738, 1637, 1564, 1340, 1132, 758, 696 cm$^{-1}$, $^1$H NMR (400 MHZ, DMSO d$_6$) 7.93 (dd, J 7.81, 4.29 Hz, 1H) 7.85 (d, J 8.23 Hz, 1H) 7.69 (m, 1H) 7.53–7.40 (8 H) 7.29 (d, J 6.84 Hz, 1H) 5.96 (s, 1H) 5.39 (dd, J 9.08, 1.9 Hz, 1H) 4.17–4.04 (m, 3H) 3.99 (d, J 17.31 Hz, 1H) d$^{13}$C NMR (100 MHZ, [CDCl3]) d 172.6, 168.3, 158.4, 155.4, 139.5, 134.0, 131.6, 131.3, 131.0, 130.3, 129.4, 129.3, 129.0, 128.8, 128.4, 128.2, 127.1, 126.4, 126.2, 124.2, 122.2, 117.8, 53.4, 51.6, 36.1, 21.6; HRMS (FAB+) calcd. for C$_{25}$H$_{20}$NO$_5$S 446.1062 Observed 446.1063

EXAMPLE 5

Synthesis of Pyridinone Methyl Ester

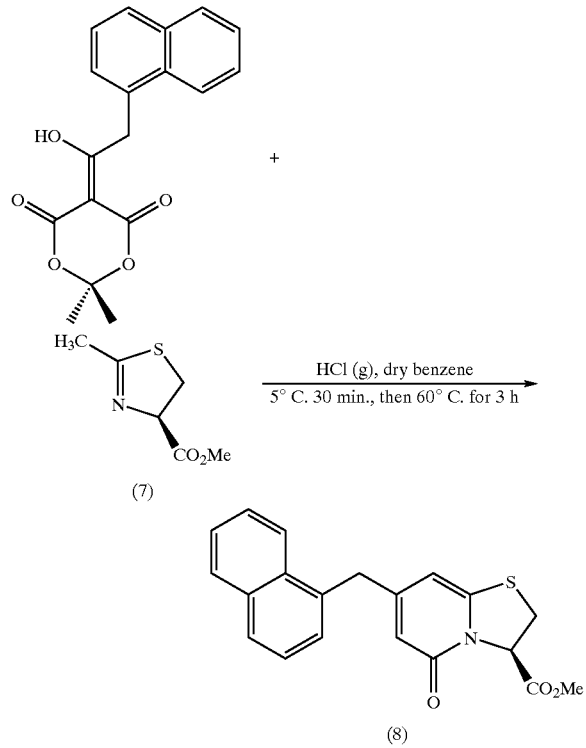

(3R)-7-(Naphthalen-1-ylmethyl)-5-oxo-2,3-dihydro-5H-thiazolo(3,2-[α])pyridine-3-carboxylic acid methyl ester, 8.

By following the procedure described for the preparation of 3 from 1 and 2, 1(950 mg, 3.0 mmol) and 7 (322 mg, 2.0 mmol) gave 8 (208 mg, 29%). $[a]_D -10°$ (c 1.74, CHCl$_3$); IR 1 2920, 1747, 1647, 1572, 1504, 1211, 1018, 779 cm$^-$, $^1$H NMR (400 MHZ, CDCl3) d 7.88–7.85 (m, 2H) 7.79 (d, J 8.18 Hz, 1H) 7.48–7.410 (m, 3H) 7.34 (d, J 6.84 Hz, 1H) 6.10 (d, J 0.96 Hz, 1H) 5.97 (d, J 1.20 Hz, 1H) 5.52 (dd, J 8.34, 2.12 Hz, 1H) 4.20 (s, 2H) 3.78 (s, 3H) 3.67 (dd, J 11.69, 8.39 Hz, 1H) 3.50 (dd, J 11.68, 2.18 Hz, 1H), $^{13}$C NMR (100 MHZ, CDCl3) d 168.4, 161.9, 155.2, 146.8, 133.9, 133.5, 131.9, 128.8, 127.9, 127.9, 126.3, 125.8, 125.5, 123.9, 114.1, 101.8, 62.5, 53.2, 38.9, 31.8; HRMS (FAB+) calcd. for C$_{20}$H$_{18}$NO$_3$S 352.1005 Observed 352.1007

EXAMPLE 6

Synthesis of Pyridinone Carboxylic Acid

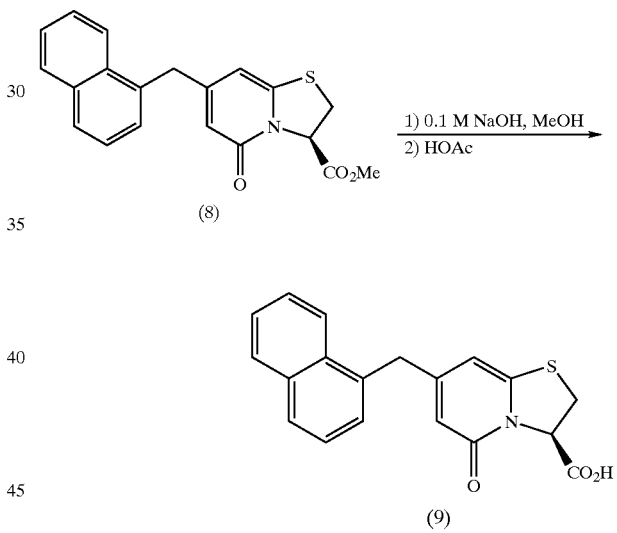

(3R)-7-(Naphthalen-1-ylmethyl)-5-oxo-2,3-dihydro-5-thiazolo(3,2-[α])pyridine-3-carboxylic acid, 9. By following the procedure described for the preparation of 4 from 3,8 (100 mg. 0.28 mmol) gave 9 (78 mg, 83%).$[a]_D -3°$ (c 0.41, dioxane:MeOH, 5:1); IR λ3060; 3035, 2900, 1896, 1720, 1622, 1500, 1323, 1215, 1176, 1011, cm$^-$, $^1$H NMR (400 MHZ, DMSO d$_6$) 13.39 (broad, 1H) 7.93 (d, J 8.05 Hz, 1H) 7.85 (d, J 7.23 Hz, 1H) 7.56–7.45 (m, 4H) 6.16–6.12 (broad, 1H) 5.88–5.83 (broad, 1H) 5.32 (d, J 8.60 Hz, 1H) 4.26–4.19 (broad, 2H) 3.82 (t, J 10.34 Hz, 1H) 3.50 (d, J 11.80 Hz, 1H) δ$^{13}$C NMR (100 MHZ, DMSO d$_6$)δ 169.4, 160.7, 154.9, 147.8, 134.4, 133.5, 131.5, 128.6, 127.8, 127.4, 126.3, 125.8, 125.7, 124.0, 112.5, 10.6, 62.2, 37.5, 31.4; HRMS (FAB+)calcd. for C$_{19}$H$_{15}$NO$_3$S 338.0851 Observed 338.0849.

EXAMPLE 7

The affinity of the following pyridinone:

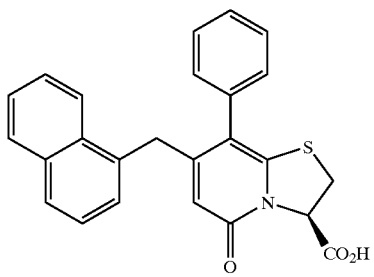

for periplasmic chaperones PapD and FimC were investigated using a direct binding assay on BIACORE 3000.

Methods

PapD (50 μg/ML in 10 mM NaAc pH 5.5) and FimC (50 μg/mL in 10 mM NaAc pH 5.5) were mobilized on Sensor Chi CM5 using standard thiol coupling procedure. This procedure was also employed for coupling of non-target proteins. Immobilization levels of 4000–10000 RU were obtained. Unmodified dextrane in one of the flow cells was used as reference surface.

The pyridinone was diluted from 10 mM DMSO stock solution to a final concentration of 30 μM in running buffer (6.7 mM phosphate buffer (9.6 g $Na_2HPO_4.2H_2O$, 1.7 G $KH_2PO_4$, 4.1 g NaCl, 100 mL $H_2O$), 3.4 mM EDTA, 0.01% TWEEN, 5% DMSO, pH 7.4) so that the concentrations of DMSO and buffer substances were carefully matched. The compounds were injected (flow rate was 30 μL/min at 25° C.) and the binding of the compounds to the immobilized chaperone proteins was observed on real time. The surface was regenerated by injection of 10 mM glycin.HCl, pH 2.0 and then washed with a 1:1 mixture of DMSO and water.

For screening of the affinity of the compounds of PapD and FimC, the pyridinone was injected (flow rate was 30 μL/min at 25° C.) at a concentration of 30 μM in triplicate.

Results

| Sample | Response Units | |
|---|---|---|
| Pyridinone | PapD 30 uM | FimC 30 uM |
| Ph_Pyr_COOH | 46,22397585 | 60,71350348 |

EXAMPLE 8

Utilizing a direct binding assay on BIACORE 3000 the affinity of the following pyridinone:

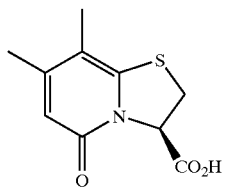

for periplasmic chaperones PapD and FimC was investigated

Methods

PapD (50 μg/ML in 10 mM NaAc pH 5.5) and FimC (50 μg/mL in 10 mM NaAc pH 5.5) were immobilized on Sensor Chi CM5 using standard thiol coupling procedure. This procedure was also employed for coupling of non-target proteins. Immobilization levels of 4000–10000 RU were obtained. Unmodified dextrane in one of the flow cells was used as reference surface.

The pyridinone was diluted from 10 mM DMSO stock solution to a final concentration of 30 μM in running buffer (6.7 mM phosphate buffer (9.6 g $Na_2HPO_4.2H_2O$, 1.7 G $KH_2PO_2PO_4$, 4.1 g NaCl, 100 mL $H_2O$), 3.4 mM EDTA, 0.01% TWEEN, 5% DMSO, pH 7.4) so that the concentrations of DMSO and buffer substances were carefully matched. The compounds were injected (flow rate was 30 μL/min at 25° C.) and the binding of the compounds to the immobilized chaperone proteins was observed on real time. The surface was regenerated by injection of 10 mM glycin.HCl, pH 2.0 and then washed with a 1:1 mixture of DMSO and water.

For screening of the affinity of the compounds of PapD and FimC, the pyridinone was injected (flow rate was 30 μL/min at 25° C.) at a concentration of 30 μM in triplicate.

Results

| Sample | Response Units | |
|---|---|---|
| Pyridinone | PapD 30 uM | FimC 30 uM |
| Me_Me_Pyr_COOH | 1,676914034 | 6,535311642 |

EXAMPLE 9

The affinity of the following pyridinone:

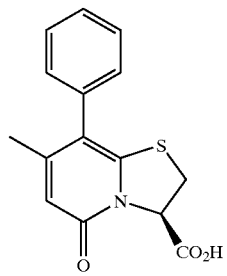

for periplasmic chaperones PapD and FimC was investigated using a direct binding assay on BIACORE 3000.

Methods

PapD (50 μg in 10 mM NaAc pH 5.5) and FimC (50 μg/mL in 10 mM NaAc pH 5.5) were immobilized on Sensor Chi CM5 using standard thiol coupling procedure. This procedure was also employed for coupling of non-target proteins. Immobilization levels of 4000–10000 RU were obtained. Unmodified dextrane in one of the flow cells was used as reference surface.

The pyridinone was diluted from 10 mM DMSO stock solution to a final concentration of 30 μM in running buffer (6.7 mM phosphate buffer (9.6 g $Na_2HPO_4.2H_2O$, 1.7 G $KH_2PO_4$, 4.1 g NaCl, 100 mL $H_2O$), 3.4 mM EDTA, 0.01% TWEEN, 5% DMSO, pH 7.4) so that the concentrations of DMSO and buffer substances were carefully matched. The compounds were injected (flow rate was 30 μL/min at 25° C.) and the binding of the compounds to the immobilized chaperone proteins was observed on real time. The surface was regenerated by injection of 10 mM glycin.HCl, pH 2.0 and then washed with a 1:1 mixture of DMSO and water.

For screening of the affinity of the compounds of PapD and FimC, the pyridinone was injected (flow rate was 30 μL/min at 25° C.) at a concentration of 30 μM in triplicate.

Results

| Sample | Response Units | |
|---|---|---|
| Pyridinone | PapD 30 uM | FimC 30 uM |
| Me_Ph_Pyr_COOH | 3,90056354 | 6,753367367 |

EXAMPLE 10

A direct binding assay on BIACORE 3000 was employed to test the affinity of the following pyridinone:

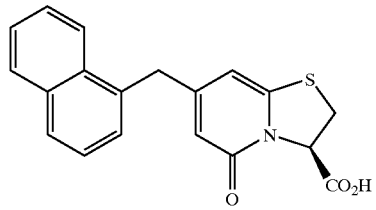

for periplasmic chaperones PapD and FimC.

Methods

PapD (50 μg/ML in 10 mM NaAc pH 5.5) and FimC (50 μg/mL in 10 mM NaAc pH 5.5) were immobilized on Sensor Chi CM5 using standard thiol coupling procedure. This procedure was also employed for coupling of non-target proteins. Immobilization levels of 4000–10000 RU were obtained. Unmodified dextrane in one of the flow cells was used as reference surface.

The pyridinone was diluted from 10 mM DMSO stock solution to a final concentration of 30 μM in running buffer (6.7 mM phosphate buffer (9.6 g $Na_2HPO_4.2H_2O$, 1.7 G $KH_2PO_4$, 4.1 g NaCl, 100 mL $H_2O$), 3.4 mM EDTA, 0.01% TWEEN, 5% DMSO, pH 7.4) so that the concentrations of DMSO and buffer substances were carefully matched. The compounds were injected (flow rate was 30 μL/min at 25° C.) and the binding of the compounds to the immobilized chaperone proteins was observed on real time. The surface was regenerated by injection of 10 mM glycin.HCl, pH 2.0 and then washed with a 1:1 mixture of DMSO and water.

For screening of the affinity of the compounds of PapD and FimC, the pyridinone was injected (flow rate was 30 μL/min at 25° C.) at a concentration of 30 μM in triplicate.

Results

| Sample | Response Units | |
|---|---|---|
| Pyridinone | PapD 30 uM | FimC 30 uM |
| H_Pyr_COOH | 6,760176162 | 11,69075072 |

EXAMPLE 11

Solid-Phase Synthesis of the Ring Fused 2-Pyridinone Framework

1) Attachment of Boc-Cys(Trt)-OH to Acid Stable HMBA-AM Resin to Give A

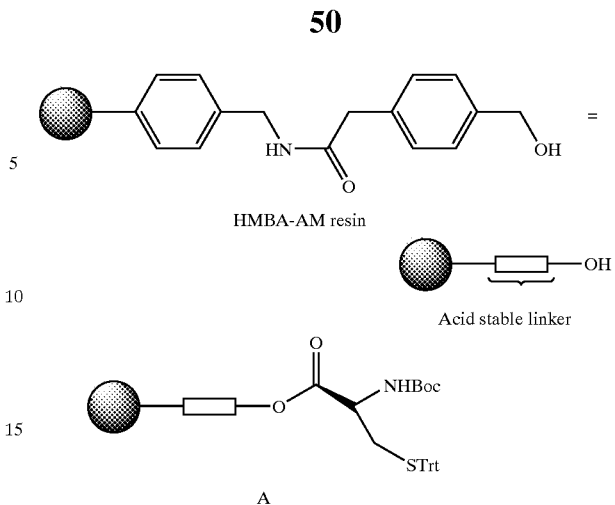

HMBA-AM resin (5031 mg, capacity 1.16 mmol/g, 0.58 mmol) was allowed to swell in $CH_2Cl_2$ in two reaction vessels in a Quest 210C organic synthesizer for 1 h. The resin was washed several times with $CH_2Cl_2$ and DMF. To a solution of Boc-Cys(trt)-OH (1076 mg, 2.32 mmol) in $CH_2Cl_2$ (7 ml) was added MeIm (70 μl), and the mixture was transferred to a flask containing 1-(Mesitylene-2-sulfonyl)-3-nitro-1 H-1,2,4-triazole (MSNT) (343 mg, 1.16 mmol). The resulting solution was added to the Quest RV's and the reaction was agitated over night, followed by washing of the resin, which was used without further purification.

2) Deprotection of the Acid Labile Protecting Groups to Give B

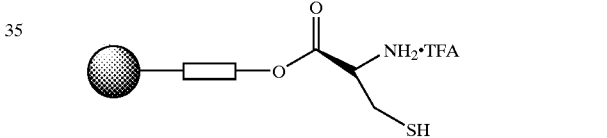

To each RV containing swelled resin-bound Boc-Cys(trt) was added 4 ml of a mixture containing 3.5 ml TFA, 0.2 ml $H_2O$, 0.2 ml thioanisol and 0.1 ml ethanedithiol. The mixture was agitated for 3.5 h and the resin was washed and used without further purification.

3) Preparation of Resin Bound $\Delta^2$-thiazoline to Give C

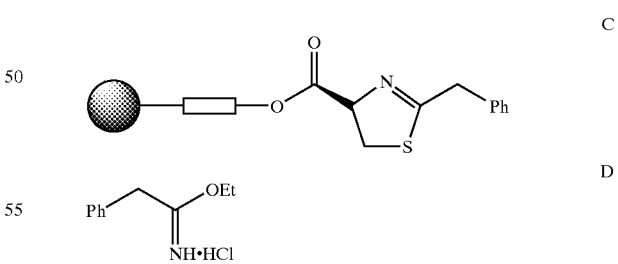

$CH_2Cl_2$ (4 ml) was added to each RV containing swelled resin-bound cysteine TFA salt, TEA (40 μl) was added dropwise, and the mixture was agitated for 30 min. The $CH_2Cl_2$ and TEA were washed out, and phenyliminoether D (150 mg, 1.00 mmol) was added, followed by 4 ml $CH_2Cl_2$ and TEA (20 μl) and the mixture was agitated overnight. The resin was washed three times with $CH_2Cl_2$, three times with DMF and three additional times with $CH_2Cl_2$. The resin was swelled for 20 min, and another 85 mg iminoether D and 20

μl TEA was added, followed by agitation for 5.5 h and washing of the resin, which was used without further purification.

4) Preparation of Resin Bound 2-pyridinone, E

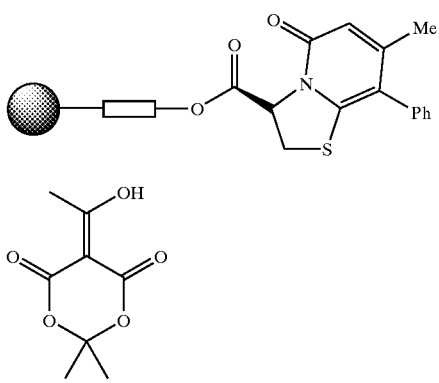

To each RV containing swelled resin-bound Δ²-thiazoline was added Meldrum's acid derivative F (162 mg, 0.87 mmol), followed by HCl-saturated benzene (4 ml). The mixture was agitated for 3 h at 60° C., then at RT overnight followed by washing of the resin (3×CH$_2$Cl$_2$, 3×DMF, 3×CH$_2$Cl$_2$). The resin was allowed to swell for another 30 min and another 110 mg (0.59 mmol) Meldrum's acid derivative F and 4 ml benzene saturated with HCl was added. After another 3 h agitation at 60° C. and 1.5 h at RT another 93 mg (0.50 mmol) of F and 4 ml HCl-saturated benzene was added. The mixture was agitated at 60° C. for 3 h, followed by agitation at RT overnight. The resin was washed and used without further purification 5) Cleavage from the Resin to Give the 2-pyridinone G

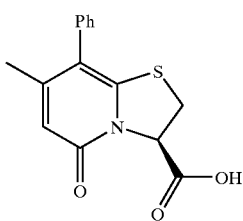

The desired pyridinone G was cleaved from the swelled resin by addition of 3 ml 1M NaOH and 1 ml THF to each RV, followed by agitation for 1 h. The resin was filtrated and the filtrate was collected in a vial. The cleavage procedure was repeated twice. The combined product collections were made acidic with amberlite IR-120(H), which was filtered off and washed with methanol. The filtrate was concentrated and the residue lyophilized to yield 40 mg (47% overall) of G as a bright yellow solid. The spectroscopic data were identical to the corresponding 2-pyridinone prepared in solution. IR λ 3014, 1705, 1612, 1477, 1443, 1319, 1290, 1265, 1157, 1011, 829, 785, 698 cm$^{-1}$. $^1$H NMR (400 MHZ, DMSO) δ 14.42 (b, 1H) 7.50–7.33 (m, 3H) 7.32–7.16 (b, 2H), 6.10 (s, 1H) 5.48 (dd, J=9.24, 1.65 Hz, 1H) 3.78 (dd, J=11.98, 9.24 Hz 1H) 3.45 (dd, J=11.98, 1.65 Hz 1H) 1.89 (s, 3H); $^{13}$C NMR (100 MHZ, DMSO) δ 170.1, 160.5, 151.4, 147.7, 137.7, 130.3, 129.3, 128.5, 115.3, 114.5, 63.8, 31.8, 20.8; HRMS (EI+) Calcd. for C$_{15}$H$_{13}$NO$_3$S 287.0616 Observed 287.0615.

EXAMPLE 12

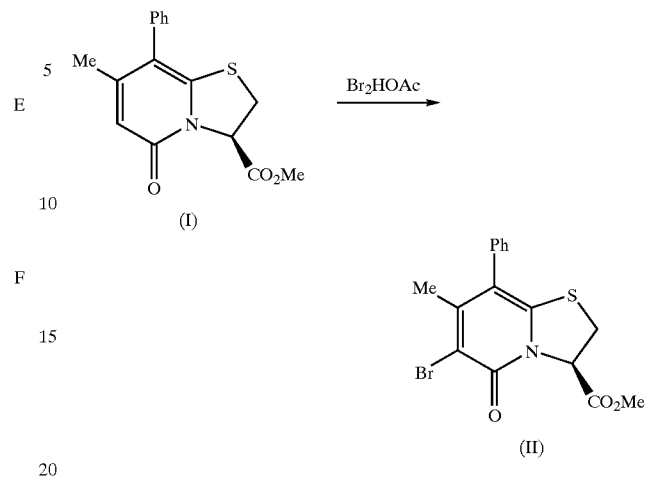

(3R)-6-Bromo-7-methyl-5-oxo-8-phenyl-2,3-dihydro-5H-thiazolo(3,2-[α])pyridine-3-carboxylic acid methyl ester, (II). To a stirred solution containing (1.40 g, 4.54 mmol) of (I) in 28 ml of acetic acid was added Br$_2$ (0.92 g, 5.78 mmol) at room temperature. The mixture was stirred at room temperature for 4 hours, quenched with distilled water and extracted with 5 portions of CH$_2$Cl$_2$. The combined organic fractions were dried over Na$_2$SO$_4$, filtered and concentrated under reduced pressure. The crude product was subjected to silica flash chromatography (heptane:ethyl acetate, 30:70) to give 1.0 g (58%) of (II) as a white solid. $(α)_D^{20}$ −213°(c 1.00, CHCL$_3$); IR λ3853, 2950, 1745 and 1579 cm$^{-1}$, $^1$H NMR (400 MHZ, CDCl$_3$) δ 2.10 (d, 3H, J=1.9 Hz), 3.44 (dm, 1H, J=11.40), 3.67 (dd, 1H, J=8.60 and 11.80), 3.90 (d, 3H, J=1.80), 5.69 (dd, 1H, J=1.4 and 8.4), 7.19–7.44 (m, 5H); $^{13}$C NMR (100 MHZ, CDCl$_3$) δ 22.3, 31.8, 53.5, 64.8, 112.8, 116.5, 128.6, 129.0, 129.1, 129.8, 130.1, 136.9, 145.2, 157.7 and 168.4. HRMS (EI+) Calcd. For C$_{16}$H$_{14}$BrNO$_3$S 378.9878 Observed 378.9947.

EXAMPLE 13

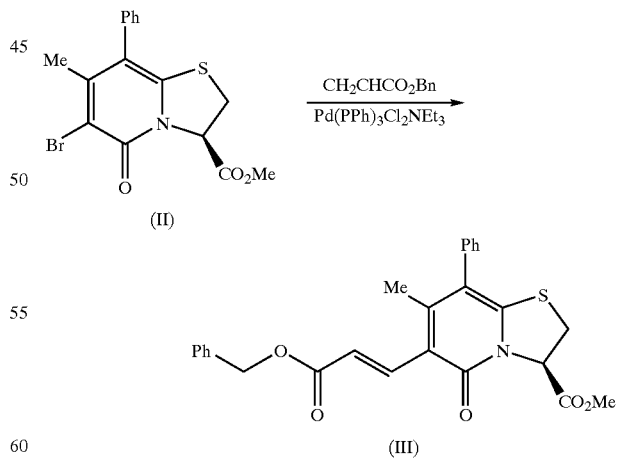

(3R)-6-(2-Benzylcarbonyl-vinyl)-7-methyl-5-oxo-8-phenyl-2,3-dihydro-5H thiazolo (3,2-[α])pyridine-3-carboxylic acid methyl ester, (III). To a solution of Pd(PPh$_3$)$_2$Cl$_2$(9.2 mg, 0.1 mmol) in 2 ml of toluene was added a solution of (II) (60 mg, 0.16 mmol), benzyl acrylate (75 mg, 0.46 mmol) and triethylamine (0.1 ml) in 2 ml of toulene. The reaction mixture was healed at reflux. After 4 h an additional 40 mg benzyl acrylate was added. The reaction was quenched with ice water after 20 h, extracted with 3 portions of CH$_2$Cl$_2$, washed with brine, dried with Na$_2$so$_4$, filtered and concentrated under reduced pressure. Purification by silica gel chromatography (heptane:ethyl acetate, 30:70) gave (III) as an orange powder, 46 mg (63%). $(\alpha)_D^{20}$ −14° (c 1.0, CHCl$_3$); IR λ 3008, 2952, 1751, 1648, 1483 cm$^{-1}$. $^1$H NMR (400 MHZ, CDCl$_3$) δ 2.14 (s, 3H) 3.43 (dd, 1H, J=2.6 and 11.1) 3.66(dd, 1H, J=8.9 and 11.2) 3.84 (s, 3H) 5.22 (dd, 2H, J=2.0 and 14.7) 5.72 (dd, 1H, J=2.4 and 11.2) 7.20–7.44 (m, 11H) 7.82 (d, 1H, J=15.6); $^{13}$C NMR (100 MHZ, CDCl$_3$) δ 18.1, 31.3, 53.4, 64.2, 65.9, 117.4, 117.9, 120.6, 127.9, 128.4, 128.9, 129.0, 129.8, 130.1, 136.4, 136.9, 137.5, 148.2, 152.0, 159.5, 168.3. 168.4; HRMS (EI+) Calcd. For C$_{26}$H$_{25}$NO$_3$S 461.1297 Observed 461.1304.

EXAMPLE 14

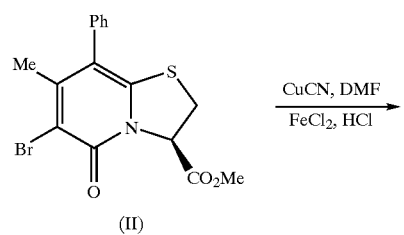

(3R)-6-cyano-7-methyl-5-oxo-8-phenyl-2,3-dihydro-5H-thiazolo(3,2-[α])pyridine-3-carboxylic acid methyl ester, (IV). A solution of (II) (70 mg, 0.18 mmol) and CuCN (dried 1 h on the vacuum pump) (40 mg, 0.44 mmol) in 1.5 ml dry DMF was heated at reflux for 16 h, under stirring and N$_2$. The mixture was allowed to cool down to 60° C. and 200 mg of FeCl$_3$ in 1 ml 2M HCl was added. The mixture was heated for 30 minutes at 60° C., cooled to room temperature and extracted 5 times with CH$_2$Cl$_2$. The combined organic phases were washed with 2*3 ml 3M HCl, 2*30 ml H$_2$O, 2*30 ml saturated Na$_2$HCO$_3$ and 2*30 ml H$_2$O, dried with Na$_2$SO$_4$, filtered and concentrated under reduced pressure. Purification with silica gel chromatography (heptane:ethyl acetate, 30:70) gave 43 mg (71%) of (IV) as a orange powder. $(\alpha)_D^{20}$ −61.5 (c 1.00, CHCl$_3$); IR λ 3002, 2960, 2360, 2211, 1739, 1484 cm$^{-1}$. $^1$H NMR (400 MHZ, CHCl$_3$) δ 2.21 (s, 3H) 3.51 (d, 1H, J=11.0) 3.73 (m, 1H) 3.85 (s, 3H) 5.72 (d, 1H, J=7.6) 7.20–7.45 (m, 5H); $^{13}$C NMR (100 MHz, CDCl$_3$) δ 20.2, 32.0. 53.8, 64.4, 100.0, 115.5, 116.7, 129.1, 129.3, 129.7, 130.0, 135.2, 154.2, 158.6, 159.1, 167.8.

EXAMPLE 15

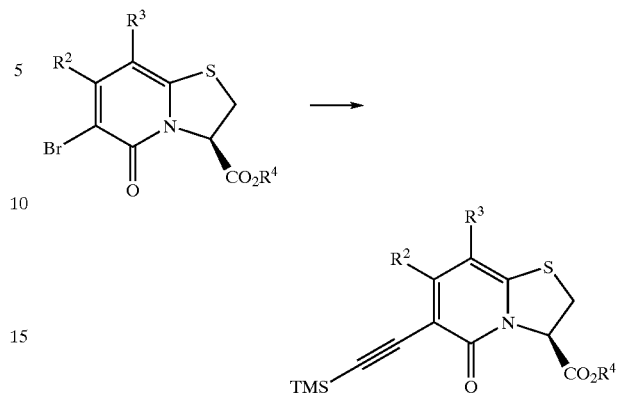

Coupling of Brominated 2-pyridinone with (trimethylsilyl)acetylene

To a solution of 0.02 g (0.08 mmol) of triphenyl phosphine in 6 mL of triethylamine is added 0.02 g of CuI followed by 15 mg of PdCl$_2$(PPh$_3$)$_2$. To this solution,is added 0.3 mL (2.2 mmol) of (trimethylsilyl)acetylene in 6 mL of toluene followed by the addition of X g (1.2 mmol) of brominated 2-pyridinone in one portion. The mixture is then heated at 160° C. in a sealed tube for 72 h, cooled to room temperature, poured into ice water, extracted with CH$_2$Cl$_2$, washed with brine and dried over Na$_2$SO$_4$. The organic extracts are filtered and concentrated under reduced pressure. The crude residue is subjected to flash silica gel chromatography to give the desired (trimethylsilyl)acetylene substituted 2-pyridinone.

EXAMPLE 16

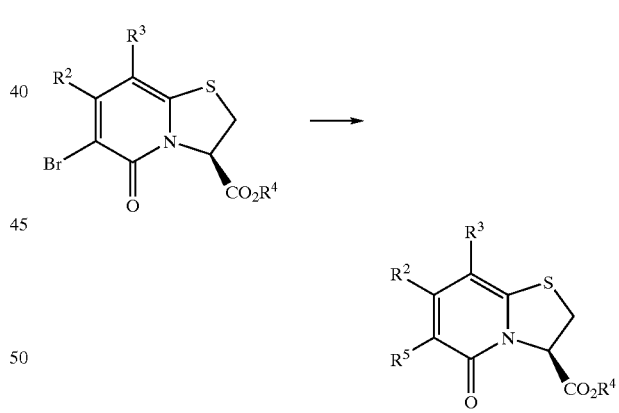

Coupling of Brominated 2-pyridinone with Organozinc Compounds

Organozink iodide (2.16 mmol, in about 10 mL of THF) is transferred via a canula to a THF solution of 5 mol % Pd(PPh$_3$), (0.127 g, 0.11 mmol) and brominated 2-pyridinone (X g, 2.19 mmol) at room temperature under an argone atmosphere. The solution is then stirred for 3 h. The mixture is thereafter worked up by pouring it into a saturated NH$_4$Cl aqueous solution (20 mL) and extracting with diethyl ether. The combined organic layers are dried over CaCl$_2$. The organic extracts are filtered and concentrated under reduced pressure. The crude residue is subjected to flash silica gel chromatography to give the desired R$^5$ substituted 2-pyridinone.

EXAMPLE 17

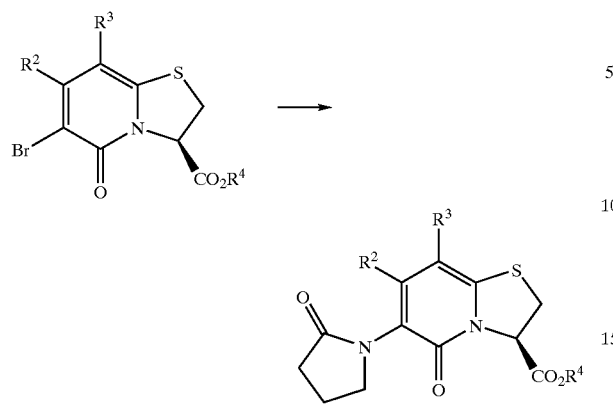

Coupling of Brominated 2-pyridinone with Lactams 2-pyrrolidinone (151 μL, 2.0 mmol), brominated 2-pyridinone (X g, 3.0 mmol), 1,1'-bis(diphenylphosphino)-ferrocene (66 mg, 0.12 mmol), palladium (II) acetate (22 mg, 0.10 mmol) and sodium tert-butoxide (0.29 g, 3.0 mmol) in 10 mL of toluene under $N_2$ are heated in a sealed tube at 120° C. for 48 hr. The mixture is cooled to room temperature, filtered through Celite, and the filtrate concentrated onto silica gel Flash chromatography then gives the lactam substituted 2-pyridinone.

EXAMPLE 18

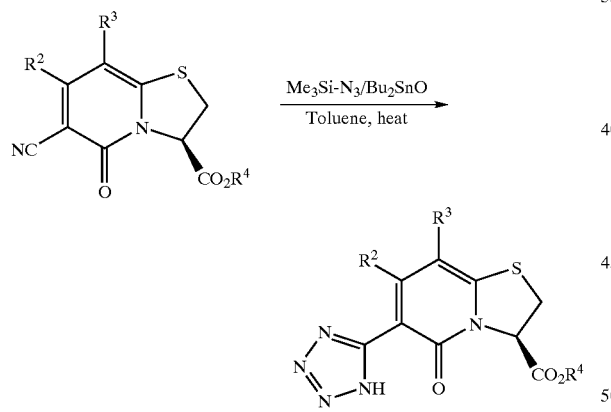

Preparation of Tetrazole 2-pyridinone from the Corresponding Nitrile

To a solution of the nitrile substituted 2-pyridinone (X g, 5.5 mmol) and trimethylsilylazide (11 mmol) in toluene (11 mL) is added dibutyltinoxide (0.55 mmol), and the mixture is heated for 24–72 h. The reaction mixture is concentrated in vacuo and the residue is dissolved in methanol and reconcentrated. The residue is then dissolved in EtOAc and washed with 10% sodium bicarbonate solution (2×25 ml). The combined aqueous layers are acidified to pH 2 with 10% HCl solution and then extracted with EtOAc. The combined organic extracts are dried with sodium sulfate, filtered and concentrated to give the tetrazole substituted 2-pyridinone.

EXAMPLE 19

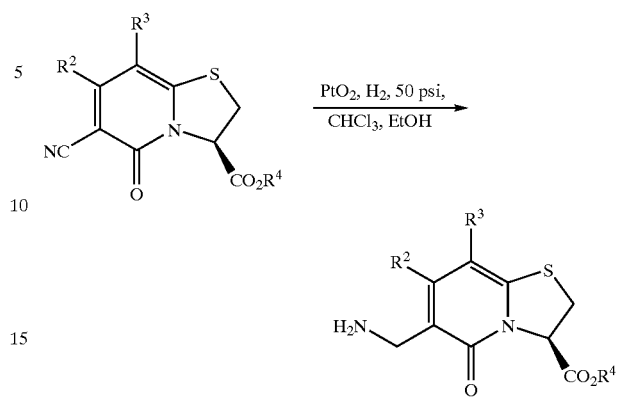

Preparation of amine 2-pyridinone from the Corresponding Nitrile

Adam's catalyst (82 mg) is suspended in dry EtOH (40 mL, distilled from $Mg/L_2$), and a solution of nitrile substituted 2-pyridinone (X mg, 3.60 mmol) in dry EtOH (10 mL) is added to the suspension, followed by bench $CHCl_3$ (1.85 mL). The mixture is shaken under $H_2$ (50 psi, Parr bottle) at room temperature for 24 h. The catalyst is filtered off, and the filtrate is concentrated. Flash chromatography then gives the amine substituted 2-pyridinone.

EXAMPLE 20

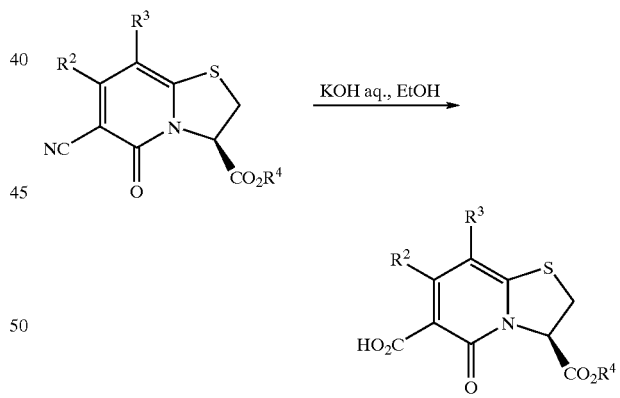

Preparation of Carboxylic Acid 2-pyridinone from the Corresponding Nitrile

To a solution of the nitrile substituted 2-pyridinone (X mg, 1.9 mmol) in EtOH (10 mL) is added a solution of KOH (1.0 g) in $H_2O$ (12 mL). This mixture is heated for 1.5 h at 70° C. and then cooled to RT and 6 N HCl is added until the material is acidic. This mixture is then extracted with EtOAc, dried with sodium sulphate, filtered and concentrated to give the desired 2-pyridinone.

EXAMPLE 21

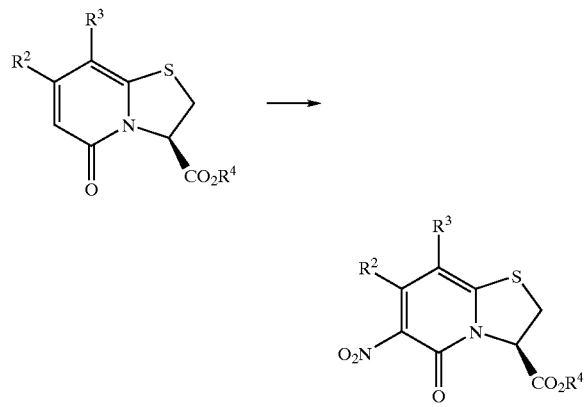

Nitration of 2-pyridinone

A 2-pyridinone (1 g) is added during 10 min. to a stirred mixture of nitric acid (95%, 10 mL) and acetic anhydride (2.4 mL) at −12° C. After 2 more minutes the solution is poured into ice-water, and the solid is removed, washed until acid-free and dried to give the desired nitrated 2-pyridinone.

EXAMPLE 22

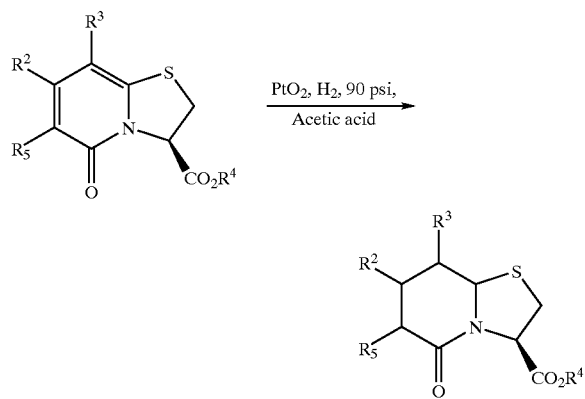

Reduction of the 2-pyridinones to the Corresponding Lactams

To a solution of a 2-pyridinone (0.6 mmol) in 7 mL of acetic acid is added a catalytic amount of $PtO_2$, and the reaction mixture is stirred under a hydrogen atmosphere of 90 psi for 2 h. After filtration of the catalyst, the solution is extracted with $CH_2Cl_2$ and washed with water. The organic layer is then washed with brine, dried over $Na_2SO_4$, and concentrated under reduced pressure. The crude residue is subjected to flash gel chromatography to give the desired lactam.

What is claimed is:
1. A pyridinone of the formula:

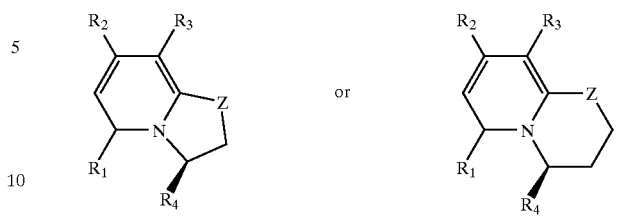

or a salt thereof wherein Z comprises S, SO, $SO_2$, O, P, PO, $PO_2$, or $CH_2$;

$R_1$ comprises oxo;

$R_2$ comprises $(CH_2)_n A$ wherein n is a natural number between 1 and 5 and A comprises hydrogen, alkyl, alkenyl, alkynyl, aryl, heteroaryl, substituted alkyl, substituted alkenyl, substituted alkynyl, substituted aryl or substituted heteroaryl;

$R_3$ comprises $(CH_2)_m D$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2 Y$, $B(OY)_2$, CHO, $CH_2 OY$, $CH(CO_2 Y)_2$, or $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

2. The pyridinone of claim 1 wherein Z comprises S;

$R_1$ comprises oxo;

$R_2$ comprises $(CH_2)_n A$ wherein n is 1 and A comprises aryl;

$R_3$ comprises $(CH_2)_m D$ wherein m is 0 and D comprises aryl; and $R_4$ comprises $CO_2 Y$ wherein Y comprises alkyl.

3. The pyridinone of claim 1 wherein aryl comprises $C_{6-15}$ aryl, alkyl comprises $C_{1-15}$ alkyl, alkenyl comprises $C_{1-15}$ alkenyl and alkynyl comprises $C_{1-15}$ alkynyl.

4. The pyridinone of claim 1 wherein Z comprises S;

$R_1$ comprises oxo;

$R_2$ comprises $(CH_2)_n A$ wherein n is 1 and A comprises $C_{10}$ aryl;

$R_3$ comprises $(CH_2)_m D$ wherein m is 0 and D comprises phenyl; and $R_4$ comprises $CO_2 Y$ wherein Y comprises hydrogen.

5. The pyridinone of claim 1 wherein Z comprises S;

$R_1$ comprises oxo;

$R_2$ comprises $(CH_2)_n A$ wherein n is 1 and A comprises $C_{10}$ aryl;

$R_3$ comprises $(CH_2)_m D$ wherein m is 0 and D comprises phenyl; and $R_4$ comprises $CO_2 Y$ wherein Y comprises methyl.

6. The pyridinone of claim 1 wherein Z comprises $SO_2$;

$R_1$ comprises oxo;

$R_2$ comprises $(CH_2)_n A$ wherein n is 1 and A comprises aryl;

$R_3$ comprises $(CH_2)_m D$ wherein m is 0 and D comprises aryl; and $R_4$ comprises $CO_2 Y$ wherein Y comprises hydrogen.

7. The pyridinone of claim 1 wherein Z comprises $SO_2$;

$R_1$ comprises oxo;

$R_2$ comprises $(CH_2)_nA$ wherein n is 1 and A comprises $C_{10}$ aryl;
$R_3$ comprises $(CH_2)_mD$ wherein m is 0 and D comprises phenyl; and
$R_4$ comprises $CO_2Y$ wherein Y comprises methyl.

8. The pyridinone of claim 1 wherein Z comprises S;
$R_1$ comprises oxo;
$R_2$ comprises $(CH_2)_nA$ wherein n is 1 and A comprises aryl;
$R_3$ comprises $(CH_2)_mD$ wherein m is 1 and D comprises heteroaryl; and
$R_4$ comprises $CO_2Y$ wherein Y comprises hydrogen.

9. The pyridinone of claim 1 wherein Z comprises S;
$R_1$ comprises oxo;
$R_2$ comprises $(CH_2)_nA$ wherein n is 1 and A comprises $C_{10}$ aryl;
$R_3$ comprises phenyl; and
$R_4$ comprises $CO_2Y$ wherein Y comprises methyl.

10. The pyridinone of claim 1 wherein Z comprises $SO_2$;
$R_1$ comprises oxo;
$R_2$ comprises $(CH_2)_nA$ wherein n is 1 and A comprises $C_{10}$ aryl;
$R_3$ comprises phenyl; and
$R_4$ comprises $CO_2Y$ wherein Y comprises hydrogen.

11. The pyridinone of claim 1 wherein Z comprises S
$R_1$ comprises oxo;
$R_2$ comprises $(CH_2)_nA$ wherein n is 1 and A comprises $C_{10}$ aryl;
$R_3$ comprises $(CH_2)_m$ wherein m is O, and D comprises heteroaryl; and
$R_4$ comprises $CO_2Y$ wherein Y comprises methyl.

12. The pyridinone of claim 1 wherein Z comprises S or $SO_2$;
$R_1$ comprises oxo;
$R_2$ comprises $(CH_2)_nA$ wherein n is 1 and A comprises heteroaryl;
$R_3$ comprises $(CH_2)_mD$ wherein m is 0 and D comprises heteroaryl or substituted heteroaryl; and
$R_4$ comprises $CO_2Y$ wherein Y comprises hydrogen.

13. The pyridinone of claim 1 wherein $R_3$ is:

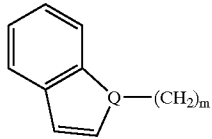

wherein m is 0–4, Q comprises N; and $R_4$ comprises $CO_2Y$ wherein Y comprises hydrogen.

14. The pyridinone of claim 1 wherein $R_3$ is:

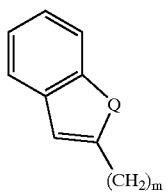

wherein m comprises 0–4 and Q comprises O, S, SO, $SO_2$, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

15. The pyridinone of claim 1 wherein $R_3$ is:

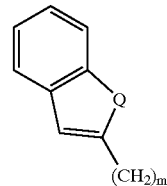

wherein m is 1 and Q comprises O, S, SO, $SO_2$, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

16. The pyridinone of claim 1 wherein $R_3$ is:

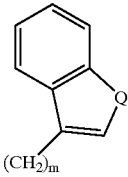

wherein m is 0–4 and Q comprises O, S, SO, $SO_2$, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

17. The pyridinone of claim 1 wherein $R_3$ is:

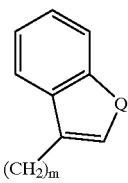

wherein m is 0 and Q comprises O, S, SO, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

18. The pyridinone of claim 1 wherein $R_3$ is:

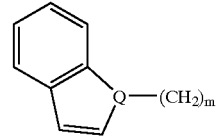

wherein m is 1 and Q comprises N; and $R_4$ comprises $CO_2Y$ wherein Y comprises hydrogen.

19. A pyridinone having the formula:

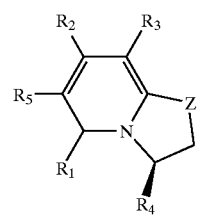 or 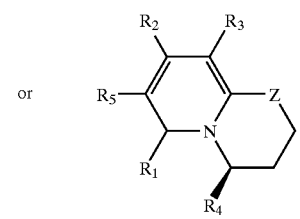

or a salt thereof wherein Z comprises S, SO, $SO_2$, O, P, PO, $PO_2$, or $CH_2$;

R₁ comprises oxo;

R₂ comprises CH₂A wherein A comprises hydrogen, alkyl, alkenyl, alkynyl, aryl, heteroaryl, substituted alkyl, substituted alkenyl, substituted alkynyl, substituted aryl or substituted heteroaryl;

R₃ comprises (CH₂)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl;

R₄ comprises CO₂Y, B(OY)₂, CHO, CH₂OY, CH(CO₂Y)₂, or PO(OY)₂ wherein Y comprises hydrogen, alkyl, alkenyl, alkynyl, aryl, heteroaryl, substituted alkyl, substituted alkenyl, substituted alkynyl, substituted aryl or substituted heteroaryl; and R₅ comprises halogen, nitrile, CO₂H, CH₂NH₂, cyclic CHN₄, a lactam, NO₂, (trimethylsilyl)acetylene, G wherein G comprises aryl or alkyl, alkenyl, or alkynyl, or (CH)₂E wherein E comprises COR, CO₂R, CHO, or CN and R comprises alkyl, alkenyl, alkynyl, aryl, heteroaryl, substituted alkyl, substituted alkenyl, substituted alkynyl, substituted aryl or substituted heteroaryl.

20. The pyridinone of claim 19 wherein Z comprises S;
R₁ comprises oxo;
R₂ comprises CH₂A wherein A comprises aryl;
R₃ comprises (CH₂)$_m$D wherein m is 0 and D comprises aryl;
R₄ comprises CO₂Y wherein Y comprises hydrogen; and
R₅ comprises bromine.

21. The pyridinone of claim 19 wherein Z comprises S;
R₁ comprises oxo;
R₂ comprises CH₂A wherein A comprises aryl;
R₃ comprises (CH₂)$_m$D wherein m is 0 and D comprises aryl;
R₄ comprises CO₂Y wherein Y comprises hydrogen; and
R₅ comprises nitrile.

22. The pyridinone of claim 19 wherein Z comprises S;
R₁ comprises oxo;
R₂ comprises CH₂A wherein A comprises aryl;
R₃ comprises (CH₂)$_m$D wherein m is 0 and D comprises aryl;
R₄ comprises CO₂Y wherein Y comprises hydrogen; and
R₅ comprises (CH)₂E wherein E comprises CO₂R and R comprises benzyl.

23. The pyridinone of claim 19 wherein aryl comprises C$_{6-15}$ aryl, alkyl comprises C$_{1-15}$ alkyl, alkenyl comprises C$_{1-15}$ alkenyl and alkynyl comprises C$_{1-15}$ alkynyl.

24. The pyridinone of claim 19 wherein Z comprises S;
R₁ comprises oxo;
R₂ comprises CH₂A wherein A comprises C₁₀ aryl;
R₃ comprises (CH₂)$_m$D wherein m is 0 and D comprises phenyl;
R₄ comprises CO₂Y wherein Y comprises hydrogen; and
R₅ comprises bromine.

25. The pyridinone of claim 19 wherein Z comprises S;
R₁ comprises oxo;
R₂ comprises CH₂A wherein A comprises C₁₀ aryl;
R₃ comprises (CH₂)$_m$D wherein m is 0 and D comprises phenyl; and
R₄ comprises CO₂Y wherein Y comprises methyl.

26. The pyridinone of claim 19 wherein Z comprises SO₂;
R₁ comprises oxo;
R₂ comprises CH₂A wherein A comprises aryl;
R₃ comprises (CH₂)$_m$D wherein m is 0 and D comprises aryl; and
R₄ comprises CO₂Y wherein Y comprises hydrogen.

27. The pyridinone of claim 19 wherein Z comprises SO₂;
R₁ comprises oxo;
R₂ comprises CH₂A wherein A comprises C₁₀ aryl;
R₃ comprises (CH₂)$_m$D wherein m is 0 and D comprises phenyl; and
R₄ comprises CO₂Y wherein Y comprises methyl.

28. The pyridinone of claim 19 wherein Z comprises S;
R₁ comprises oxo;
R₂ comprises CH₂A wherein A comprises aryl;
R₃ comprises (CH₂)$_m$D wherein m is 1 and D comprises heteroaryl; and
R₄ comprises CO₂Y wherein Y comprises hydrogen.

29. The pyridinone of claim 19 wherein Z comprises S;
R₁ comprises oxo;
R₂ comprises CH₂A wherein A comprises C₁₀ aryl;
R₃ comprises phenyl; and
R₄ comprises CO₂Y wherein Y comprises methyl.

30. The pyridinone of claim 19 wherein Z comprises SO₂;
R₁ comprises oxo;
R₂ comprises CH₂A wherein A comprises C₁₀ aryl;
R₃ comprises phenyl; and
R₄ comprises CO₂Y wherein Y comprises hydrogen.

31. The pyridinone of claim 19 wherein Z comprises S
R₁ comprises oxo;
R₂ comprises CH₂A wherein A comprises C₁₀ aryl;
R₃ comprises (CH₂)$_m$ wherein m is O, and D comprises heteroaryl; and
R₄ comprises CO₂Y wherein Y comprises methyl.

32. The pyridinone of claim 19 wherein Z comprises S or SO₂;
R₁ comprises oxo;
R₂ comprises CH₂A wherein A comprises heteroaryl;
R₃ comprises (CH₂)$_m$D wherein m is 0 and D comprises heteroaryl; and
R₄ comprises CO₂Y wherein Y comprises hydrogen.

33. The pyridinone of claim 19 wherein R₃ is:

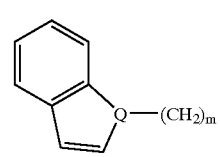

wherein m is 0–4, Q comprises N; and R₄ comprises CO₂Y wherein Y comprises hydrogen.

34. The pyridinone of claim 19 wherein $R_3$ is:

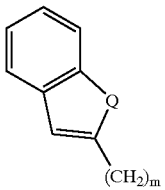

wherein m is 0–4 and Q comprises O, S, SO, $SO_2$, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

35. The pyridinone of claim 19 wherein $R_3$ is:

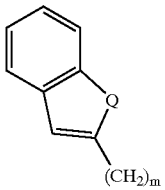

wherein m is 1 and Q comprises O, S, SO, $SO_2$, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

36. The pyridinone of claim 19 wherein $R_3$ is:

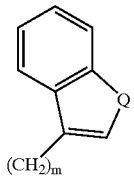

wherein m is 0–4 and Q comprises O, S, SO, $SO_2$, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

37. The pyridinone of claim 19 wherein $R_3$ is:

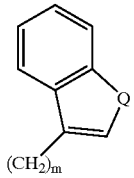

wherein m comprises 0 and Q comprises O, S, SO, NH, NO or NR wherein R comprises alkyl, alkenyl, alkynyl, aryl, heteroaryl, acyl, or sulfonyl; and $R_4$ comprises $CO_2Y$ wherein Y comprises hydrogen.

38. The pyridinone of claim 19 wherein $R_3$ is:

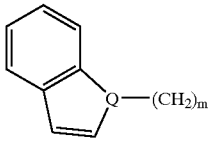

wherein m is 1 and Q comprises N; and $R_4$ comprises $CO_2Y$ wherein Y comprises hydrogen.

39. A pyridinone having the following formula:

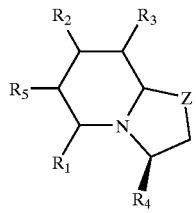

wherein Z comprises S, SO, $SO_2$, O, P, PO, $PO_2$, or $CH_2$;

$R_1$ comprises oxo;

$R_2$ comprises $CH_2A$ wherein A comprises hydrogen, alkyl, alkenyl, alkynyl, aryl, heteroaryl, substituted alkyl, substituted alkenyl, substituted alkynyl, substituted aryl or substituted heteroaryl;

$R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl;

$R_4$ comprises $CO_2Y$, $B(OY)_2$, CHO, $CH_2OY$, $CH(CO_2Y)_2$, or $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl; and $R_5$ is hydrogen, halogen, nitrile, $CO_2H$, $CH_2NH_2$, cyclic $CHN_4$, a lactam, $NO_2$, (trimethylsilyl)acetylene, G wherein G comprises alkyl, alkenyl, alkynyl, aryl, substituted alkyl, substituted alkenyl, substituted alkynyl, substituted aryl, or $(CH)_2E$ wherein E comprises COR, $CO_2R$, CHO, or CN and R comprises alkyl, alkenyl, alkynyl, aryl, heteroaryl, substituted alkyl, substituted alkenyl, substituted alkynyl, substituted aryl or substituted heteroaryl;

provided, however, when Z is S, $R_5$ is not alkyl or substituted alkyl.

40. A pyridinone having the following formula:

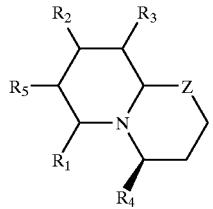

wherein when Z comprises S, SO, $SO_2$, O, P, PO, $PO_2$, or $CH_2$;

$R_1$ comprises oxo;

$R_2$ comprises $CH_2A$ wherein A comprises hydrogen, alkyl, alkenyl, alkynyl, aryl, heteroaryl, substituted alkyl, substituted alkenyl, substituted alkynyl, substituted aryl or substituted heteroaryl;

$R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl;

$R_4$ comprises $CO_2Y$, $B(OY)_2$, CHO, $CH_2OY$, $CH(CO_2Y)_2$, or $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl; and $R_5$ is hydrogen, halogen, nitrile, $CO_2H$, $CH_2NH_2$, cyclic $CHN_4$, a lactam, $NO_2$, (trimethylsilyl)acetylene, G wherein G comprises alkyl, alkenyl, alkynyl, aryl, substituted alkyl, substituted alkenyl, substituted alkynyl, substituted aryl, or $(CH)_2E$ wherein E comprises COR, $CO_2R$, CHO, or CN and R comprises alkyl, alkenyl, alkynyl, aryl, heteroaryl, substituted alkyl, substituted alkenyl, substituted alkynyl, substituted aryl or substituted heteroaryl;

provided, however, when Z is $CH_2$, $R_5$ is not alkyl or substituted alkyl.

41. A process for the preparation of a pyridinone of formula:

comprising reacting in solution a Meldrum's acid derivative of the formula:

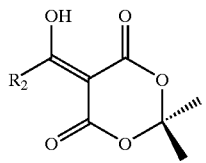

with an imine of formula:

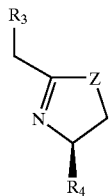

wherein Z comprises S, SO, $SO_2$, O, P, PO, $PO_2$, or $CH_2$; $R_1$ comprises oxo; $R_2$ comprises $(CH_2)_nA$ wherein n is a natural number between 0 and 5 and A comprises alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises alkyl, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, CHO, $CH_2OY$, $PO(OY)_2$, $B(OY)_2$, or $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

42. The process of claim 41 wherein Z comprises S, $R_1$ comprises oxo, n is 1, A comprises napthyl, m is 0, D comprises phenyl, $R_4$ comprises $CO_2Y$ wherein Y comprises methyl.

43. The process of claim 41 wherein Z comprises S or $SO_2$, $R_1$ comprises oxo, n is 1, A comprises aryl, m is 0, D comprises aryl, $R_4$ comprises $CO_2Y$ wherein Y comprises hydrogen or alkyl.

44. The process of claim 43 wherein Y comprises hydrogen.

45. The process of claim 43 wherein Y comprises methyl.

46. The process of claim 45 further comprising hydrolysis of the pyridinone.

47. The process of claim 46 wherein the Meldrum's acid derivative and the imine are reacted with a Lewis Acid.

48. The process of claim 41 wherein $R_4$ comprises $CO_2Y$ and Y comprises alkyl, alkenyl, alkynyl, aryl, heteroaryl, substituted alkyl, substituted alkenyl, substituted alkynyl, substituted aryl or substituted heteroaryl.

49. The process of claim 48 further comprising hydrolysis of the pyridinone.

50. The process of claim 41 wherein a Meldrum's acid derivative having the structure:

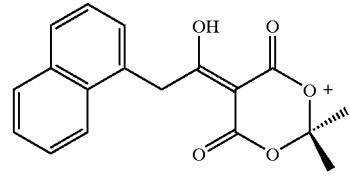

and a thiazoline having the structure:

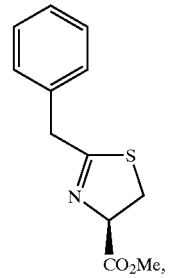

are reacted to form a pyridinone having the following structure:

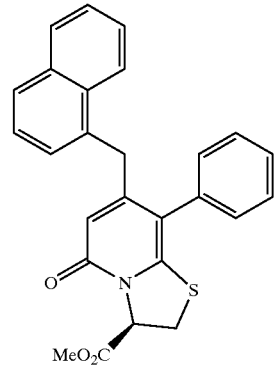

which is then hydrolyzed in basic conditions followed by acidic work-up to yield the following structure:

51. The process of claim 41 wherein a Meldrum's acid derivative having the structure:

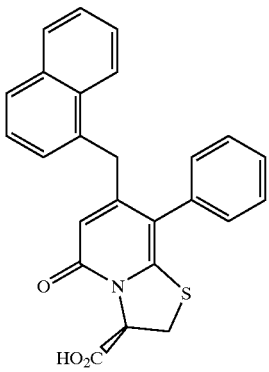

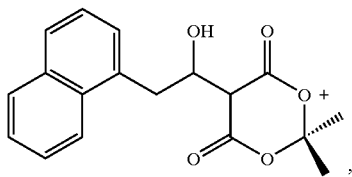

and a thiazoline having the structure:

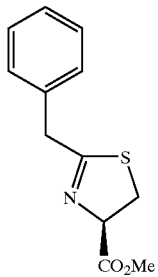

are reacted to form a pyridinone having the following structure:

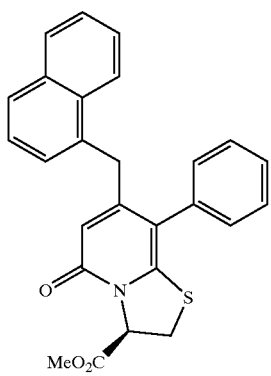

which is then hydrolyzed using sodium hydroxide followed by quenching with acetic acid to yield the following structure:

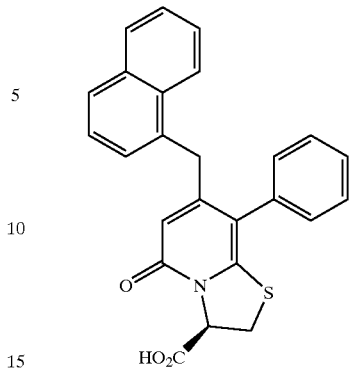

52. The process of claim 41 further comprising treating the pyridinone with a nitrating agent to form a nitrated pyridinone derivative of the formula:

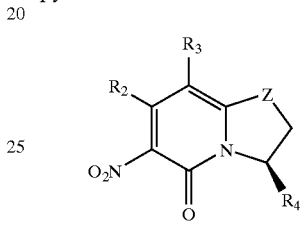

wherein Z comprises S, SO, $SO_2$, O, P, PO, $PO_2$, or $CH_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, CHO, $CH_2OY$, $PO(OY)_2$, $B(OY)_2$, or $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

53. The process of claim 52 wherein the nitrating agent is nitric acid.

54. The process of claim 41 further comprising reducing the pyridinone to form a pyridinone derivative of the formula:

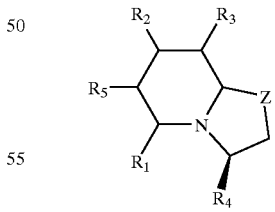

or a salt thereof wherein Z comprises S, SO, $SO_2$, O, P, PO, $PO_2$, or $CH_2$; $R_1$ comprises oxo; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; $R_4$ comprises $CO_2Y$, $B(OY)_2$, CHO, $CH_2OY$, $CH(CO_2Y)_2$, or $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl; and $R_5$ is hydrogen, halogen, nitrile, $CO_2H$, $CH_2NH_2$, cyclic $CHN_4$, a lactam, $NO_2$, (trimethylsilyl) acetylene, G wherein G comprises alkyl, alkenyl, alkynyl, aryl, substituted alkyl, substituted alkenyl, substituted alkynyl, substituted aryl, or $(CH)_2E$ wherein E comprises COR, $CO_2R$, CHO, or CN and R comprises alkyl, alkenyl, alkynyl, aryl, heteroaryl, substituted alkyl, substituted alkenyl, substituted alkynyl, substituted aryl or substituted heteroaryl.

55. The process of claim 54 wherein the pyridinone is reduced by reacting the pyridinone with $PtO_2$ and hydrogen.

56. The process of claim 41 further comprising treating the pyridinone with a halogenating agent to form a halogen substituted pyridinone derivative of the formula:

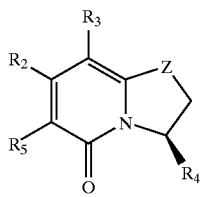

wherein Z comprises S, SO, $SO_2$, O, P, PO, $PO_2$, or $CH_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; $R_4$ comprises $CO_2Y$, $B(OY)_2$, CHO, $CH_2OY$, $PO(OY)_2$, $B(OY)_2$, or $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl; and $R_5$ comprises halogen.

57. The process of claim 56 wherein the halogenating agent comprises bromine.

58. The process of claim 56 wherein the halogen comprises bromine or iodine.

59. The process of claim 56 further comprising reacting the halogen substituted pyridinone with a compound of formula $CH_2$=CHE to form a pyridinone derivative of formula:

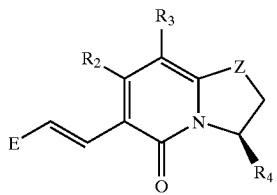

wherein E comprises COR, $CO_2R$, CHO, or CN and R comprises alkyl, alkenyl, alkynyl, aryl, heteroaryl, substituted alkyl, substituted alkenyl, substituted alkynyl, substituted aryl or substituted heteroaryl; Z comprises S, SO, $SO_2$, O, P, PO, $PO_2$, or $CH_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, CHO, $CH_2OY$, $PO(OY)_2$, $B(OY)_2$, or $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

60. The process of claim 59 wherein E comprises $CO_2R$ and R comprises benzyl.

61. The process of claim 56 further comprising an organometallic coupling with the halogen substituted pyridinone derivative to form a pyridinone derivative of the formula:

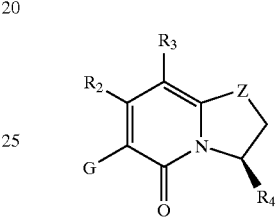

wherein G comprises aryl, alkyl, alkenyl, alkynyl, substituted aryl, substituted alkyl, substituted alkenyl or substituted alkynyl; Z comprises S, SO, $SO_2$, O, P, PO, $PO_2$, or $CH_2$; $R_2$ comprises $(CH_2)_nA$ wherein n is between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, CHO, $CH_2OY$, $PO(OY)_2$, $B(OY)_2$, $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

62. The process of claim 61 wherein the organometallic coupling comprises reacting the halogen substituted pyridinone derivative with GZnX in the presence of cuprous iodide as catalyst wherein G comprises substituted or unsubstituted aryl, substituted or unsubstituted alkyl, substituted or unsubstituted alkenyl, or substituted or unsubstituted alkynyl and X comprises I, Br, or Cl.

63. The process of claim 62 wherein G is selected from a the group consisting of:

-continued

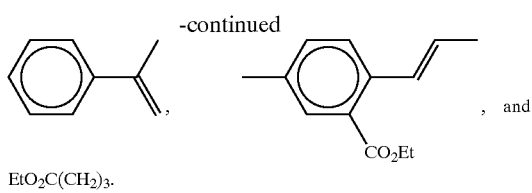

EtO₂C(CH₂)₃-

64. The process of claim 56 further comprising an organometallic coupling of the halogen substituted pyridinone derivative with (trimethylsilyl)acetylene to form a pyridinone derivative of the formula:

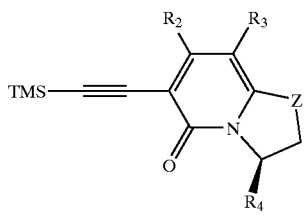

wherein Z comprises S, SO, SO$_2$, O, P, PO, PO$_2$, or CH$_2$; R$_2$ comprises (CH$_2$)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and R$_4$ comprises CO$_2$Y, B(OY)$_2$, CHO, CH$_2$OY, PO(OY)$_2$, B(OY)$_2$, or CH(CO$_2$Y)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

65. The process of claim 64 wherein the organometallic coupling is catalyzed by palladium.

66. The process of claim 64 wherein the organometallic coupling is catalyzed by PdCl$_2$(PPh$_3$)$_2$ and CuI.

67. The process of claim 56 further comprising an organometallic coupling with the halogen substituted pyridinone to form a pyridinone derivative of the formula:

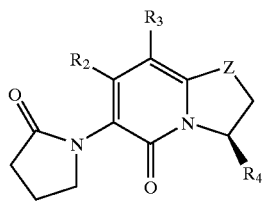

wherein Z comprises S, SO, SO$_2$, O, P, PO, PO$_2$, or CH$_2$; R$_2$ comprises (CH$_2$)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and R$_4$ comprises CO$_2$Y, B(OY)$_2$, CHO, CH$_2$OY, PO(OY)$_2$, B(OY)$_2$, or CH(CO$_2$Y)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

68. The process of claim 67 wherein the organometallic coupling is catalyzed by palladium.

69. The process of claim 67 wherein the organometallic coupling is catalyzed by palladium acetate.

70. The process of claim 56 further comprising reacting the halogen substituted pyridinone derivative with a cyanating agent to form a nitrile substituted pyridinone derivative of the formula

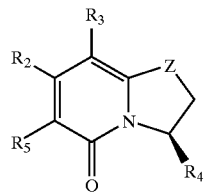

wherein Z comprises S, SO, SO$_2$, O, P, PO, PO$_2$, or CH$_2$; R$_2$ comprises (CH$_2$)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; R$_4$ comprises CO$_2$Y, B(OY)$_2$, CHO, CH$_2$OY, PO(OY)$_2$, B(OY)$_2$, or CH(CO$_2$Y)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl; and R$_5$ comprises nitrile.

71. The process of claim 70 wherein the cyanating agent comprises CuCN.

72. The process of claim 70 further comprising hydrolyzing the nitrile substituted pyridinone derivative to form a pyridinone derivative of the formula:

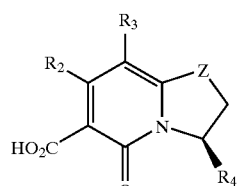

wherein Z comprises S, SO, SO$_2$, O, P, PO, PO$_2$, or CH$_2$; R$_2$ comprises (CH$_2$)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; R$_4$ comprises CO$_2$Y, B(OY)$_2$, CHO, CH$_2$OY, PO(OY)$_2$, B(OY)$_2$, or CH(CO$_2$Y)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

73. The process of claim 72 wherein the nitrile substituted pyridinone derivative is hydrolyzed with potassium hydroxide.

74. The process of claim 70 further comprising reducing the nitrile substituted pyridinone derivative to form a pyridinone derivative of the formula:

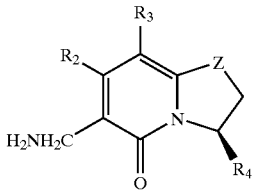

wherein Z comprises S, SO, $SO_2$, O, P, PO, $PO_2$, or $CH_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; $R_4$ comprises $CO_2Y$, $B(OY)_2$, CHO, $CH_2OY$, $PO(OY)_2$, $B(OY)_2$, or $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

75. The process of claim 70 wherein the nitrile substituted pyridinone derivative is reduced with $PtO_2$ and hydrogen.

76. The process of claim 70 further comprising functionalizing the nitrile substituted pyridinone derivative to form a pyridinone derivative of the formula:

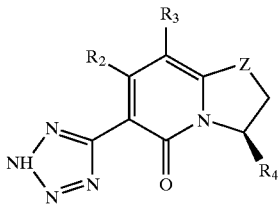

wherein Z comprises S, SO, $SO_2$, O, P, PO, $PO_2$, or $CH_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; $R_4$ comprises $CO_2Y$, $B(OY)_2$, CHO, $CH_2OY$, $PO(OY)_2$, $B(OY)_2$, or $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

77. The process of claim 76 wherein the nitrile substituted pyridinone is functionalized with trimethylsilylazide and dibutyltinoxide.

78. A process for the preparation of a pyridinone of formula:

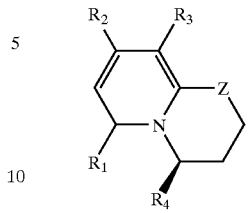

comprising reacting in solution a Meldrum's acid derivative of the formula:

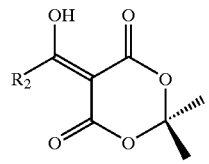

with an imine of formula:

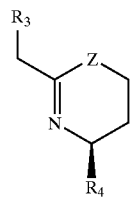

wherein Z comprises S, SO, $S_2$, O, P, PO, $PO_2$, or $CH_2$; $R_1$ comprises oxo; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, $CH(CO_2Y)_2$, CHO, or $PO(OY)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

79. The process of claim 78 wherein Z comprises S, n is 1, A comprises napthyl, m is 0, D comprises phenyl, and $R_4$ comprises $CO_2Y$ wherein Y comprises methyl.

80. The process of claim 78 wherein Z comprises S or $SO_2$, n is 1, A comprises aryl, m is 0, D comprises aryl, and $R_4$ comprises $CO_2Y$ wherein Y comprises hydrogen or alkyl.

81. The process of claim 80 wherein Y comprises hydrogen.

82. The process of claim 80 wherein Y comprises methyl.

83. The process of claim 82 further comprising hydrolysis of the pyridinone.

84. The process of claim 78 wherein the Meldrum's acid derivative and the imine are reacted with a Lewis Acid.

85. The process of claim 78 wherein $R_4$ comprises $CO_2Y$ and Y comprises alkyl, alkenyl, alkynyl, aryl, heteroaryl, substituted alkyl, substituted alkenyl, substituted alkynyl, substituted aryl or substituted heteroaryl.

86. The process of claim 85 further comprising hydrolyzing the pyridinone.

87. The process of claim 78 wherein a Meldrum's acid derivative having the structure:

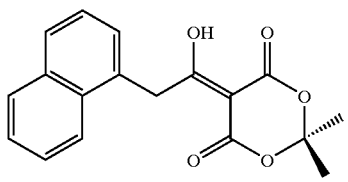

and a thiazoline having the structure:

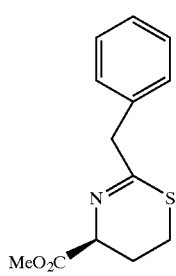

are reacted to form a pyridinone having the following structure:

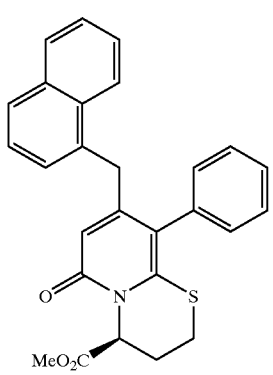

which is then hydrolyzed in basic conditions, followed by acidic work-up to yield the following structure:

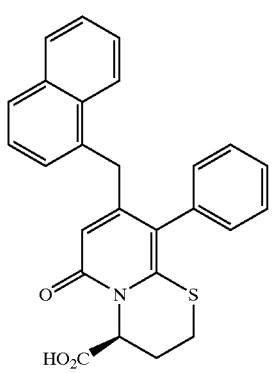

88. The process of claim 78 wherein a Meldrum's acid derivative having the structure:

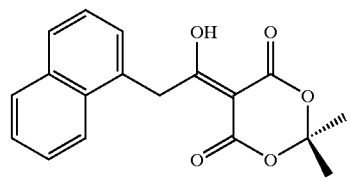

and a thiazoline having the structure:

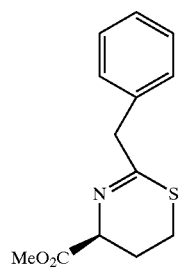

are reacted to form a pyridinone having the following structure:

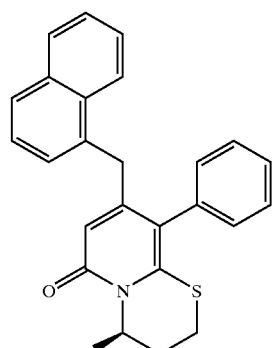

which is then hydrolyzed using sodium hydroxide, followed by quenching with acetic acid to yield the following structure:

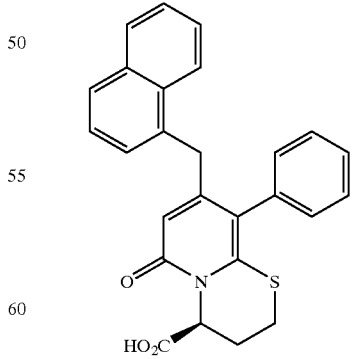

89. The process of claim 78 further comprising treating the pyridinone with a nitrating agent to form a nitrated pyridinone derivative of the formula:

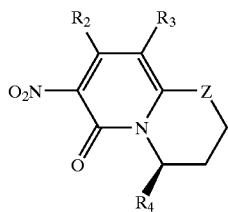

wherein Z comprises S, SO, SO₂, O, P, PO, PO₂, or CH₂; R₂ comprises (CH₂)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R₃ comprises (CH₂)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and R₄ comprises CO₂Y, B(OY)₂, CHO, CH₂OY, PO(OY)₂, B(OY)₂, or CH(CO₂Y)₂ wherein Y comprises hydrogen, alkyl, alkenyl, alkynyl, aryl, heteroaryl, substituted alkyl, substituted alkenyl, substituted alkynyl, substituted aryl or substituted heteroaryl.

90. The process of claim 89 wherein the nitrating agent is nitric acid.

91. The process of claim 78 further comprising reducing the pyridinone to form a pyridinone derivative of the formula:

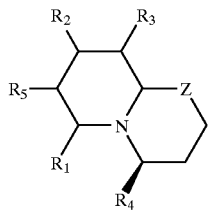

or a salt thereof wherein Z comprises S, SO, SO₂, O, P, PO, PO₂, or CH₂; R₁ comprises oxo; R₂ comprises (CH₂)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R₃ comprises (CH₂)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; R₄ comprises CO₂Y, B(OY)₂, CHO, CH₂OY, CH(CO₂Y)₂, or PO(OY)₂ wherein Y comprises hydrogen, alkyl, alkenyl, alkynyl, aryl, heteroaryl, substituted alkyl, substituted alkenyl, substituted alkynyl, substituted aryl or substituted heteroaryl; and R₅ is hydrogen, halogen, nitrile, CO₂H, CH₂NH₂, cyclic CHN₄, a lactam, NO₂, (trimethylsilyl) acetylene, G wherein G comprises alkyl, alkenyl, alkynyl, aryl, substituted alkyl, substituted alkenyl, substituted alkynyl, substituted aryl, or (CH)₂E wherein E comprises COR, CO₂R, CHO, or CN and R comprises alkyl, alkenyl, alkynyl, aryl, heteroaryl, substituted alkyl, substituted alkenyl, substituted alkynyl, substituted aryl or substituted heteroaryl.

92. The process of claim 91 wherein the reducing is accomplished by reacting the pyridinone with PtO₂ and hydrogen.

93. The process of claim 78 further comprising treating the pyridinone with a halogenating agent to form a halogen substituted pyridinone derivative of the formula:

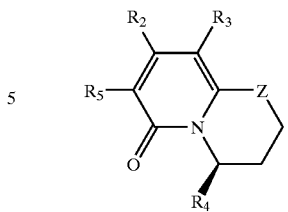

wherein Z comprises S, SO, SO₂, O, P, PO, PO₂, or CH₂; R₂ comprises (CH₂)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R₃ comprises (CH₂)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; R₄ comprises CO₂Y, B(OY)₂, CHO, CH₂OY, PO(OY)₂, B(OY)₂, or CH(CO₂Y)₂ wherein Y comprises hydrogen, alkyl, alkenyl, alkynyl, aryl, heteroaryl, substituted alkyl, substituted alkenyl, substituted alkynyl, substituted aryl or substituted heteroaryl; and R₅ comprises halogen.

94. The process of claim 93 wherein the halogenating agent comprises bromine.

95. The process of claim 93 wherein the halogen comprises bromine or iodine.

96. The process of claim 93 further comprising reacting the halogen substituted pyridinone derivative with a compound of formula CH₂=CHE to form a pyridinone derivative of formula:

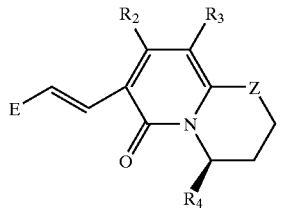

wherein E comprises COR, CO₂R, CHO, or CN and R comprises alkyl, alkenyl, alkynyl, aryl, heteroaryl, substituted alkyl, substituted alkenyl, substituted alkynyl, substituted aryl or substituted heteroaryl; Z comprises S, SO, SO₂, O, P, PO, PO₂, or CH₂; R₂ comprises (CH₂)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R₃ comprises (CH₂)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and R₄ comprises CO₂Y, B(OY)₂, CHO, CH₂OY, PO(OY)₂, B(OY)₂, or CH(CO₂Y)₂ wherein Y comprises hydrogen, alkyl, alkenyl, alkynyl, aryl, heteroaryl, substituted alkyl, substituted alkenyl, substituted alkynyl, substituted aryl or substituted heteroaryl.

97. The process of claim 96 further comprising an organometallic coupling with the halogen substituted pyridinone derivative to form a pyridinone derivative of the formula:

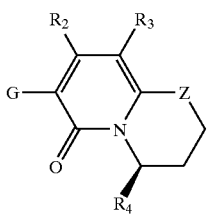

wherein G comprises aryl, alkyl, alkenyl, or alkynyl; Z comprises S, SO, SO$_2$, O, P, PO, PO$_2$, or CH$_2$; R$_2$ comprises (CH$_2$)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and R$_4$ comprises CO$_2$Y, B(OY)$_2$, CHO, CH$_2$OY, PO(OY)$_2$, B(OY)$_2$, or CH(CO$_2$Y)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

98. The process of claim 97 wherein the organometallic coupling comprises reacting the halogen substituted pyridinone derivative with GZnX in the presence of cuprous iodide as catalyst wherein G comprises substituted or unsubstituted aryl, substituted or unsubstituted alkyl, substituted or unsubstituted alkenyl, or substituted or unsubstituted alkynyl and X comprises I, Br, or Cl.

99. The process of claim 98 wherein G is selected from the group consisting of:

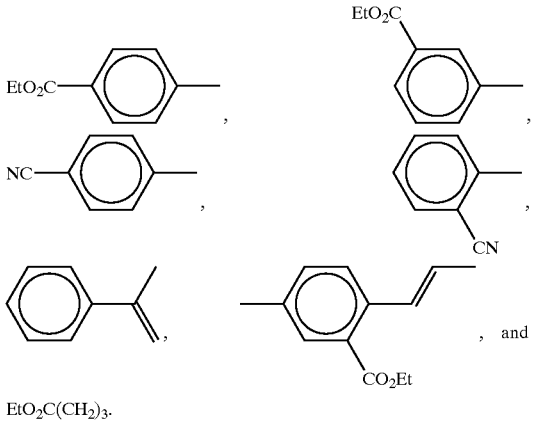

100. The process of claim 93 further comprising an organometallic coupling of the halogen substituted pyridinone derivative with (trimethylsilyl)acetylene to form a pyridinone derivative of the formula:

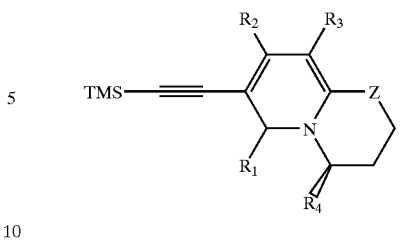

wherein Z comprises S, SO, SO$_2$, O, P, PO, PO$_2$, or CH$_2$; R$_2$ comprises (CH$_2$)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and R$_4$ comprises CO$_2$Y, B(OY)$_2$, CHO, CH$_2$OY, PO(OY)$_2$, B(OY)$_2$, or CH(CO$_2$Y)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

101. The process of claim 100 wherein the organometallic coupling is catalyzed by palladium.

102. The process of claim 100 wherein the organometallic coupling is catalyzed by PdCl$_2$(PPh$_3$)$_2$ and CuI.

103. The process of claim 93 further comprising an organometallic coupling with the halogen substituted pyridinone derivative to form a pyridinone derivative of the formula:

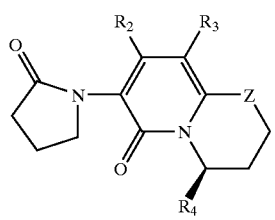

wherein Z comprises S, SO, SO$_2$, O, P, PO, PO$_2$, or CH$_2$; R$_2$ comprises (CH$_2$)$_n$A wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; R$_3$ comprises (CH$_2$)$_m$D wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and R$_4$ comprises CO$_2$Y, B(OY)$_2$, CHO, CH$_2$OY, PO(OY)$_2$, B(OY)$_2$, or CH(CO$_2$Y)$_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

104. The process of claim 103 wherein the organometallic coupling is catalyzed by palladium.

105. The process of claim 103 wherein the organometallic coupling is catalyzed by palladium acetate.

106. The process of claim 93 further comprising reacting the halogen substituted pyridinone derivative with a cyanating agent to form a nitrile substituted pyridinone derivative of the formula

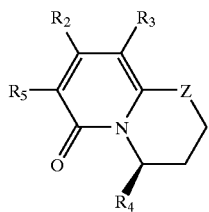

wherein Z comprises S, SO, $SO_2$, O, P, PO, $PO_2$, or $CH_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, CHO, $CH_2OY$, $PO(OY)_2$, $B(OY)_2$, or $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl; and $R_5$ comprises nitrile.

107. The process of claim 106 wherein the cyanating agent comprises CuCN.

108. The process of claim 106 further comprising hydrolyzing the nitrile substituted pyridinone derivative to form a pyridinone derivative of the formula:

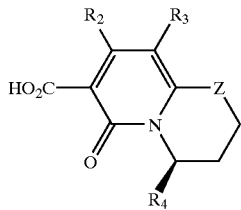

wherein Z comprises S, SO, $SO_2$, O, P, PO, $PO_2$, or $CH_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyd, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, CHO, $CH_2OY$, $PO(OY)_2$, $B(OY)_2$, or $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

109. The process of claim 106 further comprising reducing the nitrile substituted pyridinone derivative to form a pyridinone derivative of the formula:

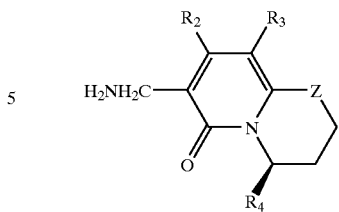

wherein Z comprises S, SO, $SO_2$, O, P, PO, $PO_2$, or $CH_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, CHO, $CH_2OY$, $PO(OY)_2$, $B(OY)_2$, or $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

110. The process of claim 109 wherein the reducing comprises reacting the nitrile substituted pyridinone derivative with $PtO_2$ and hydrogen.

111. The process of claim 106 further comprising functionalizing the nitrile substituted pyridinone derivative to form a pyridinone derivative of the formula:

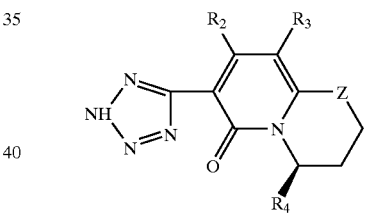

wherein Z comprises S, SO, $SO_2$, O, P, PO, $PO_2$, or $CH_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; and $R_4$ comprises $CO_2Y$, $B(OY)_2$, CHO, $CH_2OY$, $PO(OY)_2$, $B(OY)_2$, or $CH(CO_2Y)_2$ wherein Y comprises hydrogen, alkyl, alkenyl, alkynyl, aryl, heteroaryl, substituted alkyl, substituted alkenyl, substituted alkynyl, substituted aryl or substituted heteroaryl.

112. The process of claim 111 wherein the nitrile substituted pyridinone is functionalized with trimethylsilylazide and dibutyltinoxide.

113. A process for the synthesis of ring fused 2-pyridinones on a solid support, comprising the steps of: (a) preparing an imine bound to a solid support, and (b) adding a Meldrum's acid derivative under acidic conditions.

114. The process of claim 113 wherein the imine bound to the solid support has the following formula:

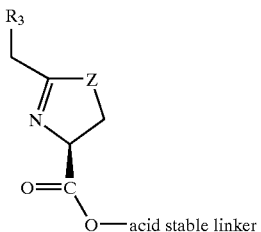

wherein Z comprises S, SO, $SO_2$, O, P, PO, $PO_2$, or $CH_2$; $R_2$ comprises $(CH_2)_n A$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; and $R_3$ comprises $(CH_2)_m D$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl.

115. The process of claim 113 wherein the Meldrum's acid derivative has the following formula:

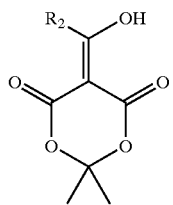

wherein $R_2$ comprises $(CH_2)_n A$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl.

116. The process of claim 113 wherein the ring fused 2-pyridinones have the formula:

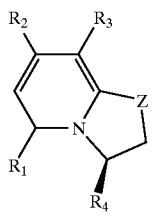 or 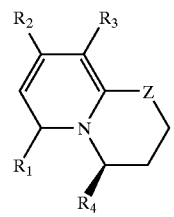

wherein $R_1$ comprises oxo;

$R_2$ comprises $(CH_2)_n A$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl;

$R_3$ comprises $(CH_2)_m D$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl;

$R_4$ comprises $CO_2H$; and

Z is S, SO, $SO_2$, O, P, PO, $PO_2$, or $CH_2$.

117. The process of claim 116 wherein n is 1, A comprises aryl, m is 0 and D comprises aryl.

118. The process of claim 116 wherein n is 1, A comprises aryl, m is 0 and D comprises phenyl.

119. The process of claim 113 wherein the solid support comprises a resin.

120. The process of claim 113 wherein the solid support comprises a HMBA-AM resin.

121. A process for the synthesis of ring fused 2-pyridinones on a solid support, comprising the steps of: (a) coupling a protected amino acid to a solid support via an acid stable linker, (b) removing the protecting groups, (c) adding an iminoether to form an imine, and (d) adding a Meldrum's acid derivative under acidic conditions.

122. The process of claim 121 wherein the iminoether has the following formula:

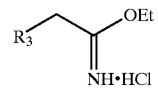

wherein $R_3$ comprises $(CH_2)_m D$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl.

123. The process of claim 122 wherein m is 0 and D comprises phenyl.

124. The process of claim 121 wherein the imine has the following formula:

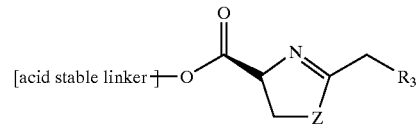

wherein Z comprises S, SO, $SO_2$, O, P, PO, $PO_2$, or $CH_2$; $R_2$ comprises $(CH_2)_n A$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; and $R_3$ comprises $(CH_2)_m D$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl.

125. The process of claim 124 wherein m is 0 and D comprises phenyl.

126. The process of claim 121 wherein the Meldrum's acid derivative has the following formula:

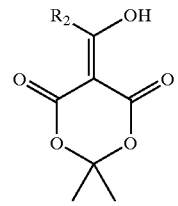

wherein $R_2$ comprises $(CH_2)_n A$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl.

127. The process of claim 121 wherein the ring fused 2-pyridinones have the following structure:

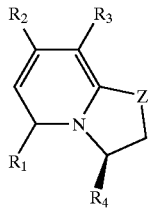 or 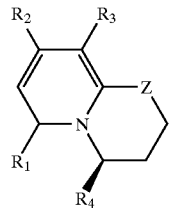

wherein $R_1$ comprises oxo;
$R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl;
$R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl;
$R_4$ comprises $CO_2H$; and
Z comprises S, SO, $SO_2$, O, P, PO, $PO_2$, $CH_2$, or $CR_2$.

128. The process of claim 127 wherein n is 1, A comprises aryl, m is 0 and D comprises aryl.

129. The process of claim 127 wherein n is 1, A comprises aryl, m is 0 and D comprises phenyl.

130. The process of claim 121 wherein the protected amino acid comprises Boc-Cys(Trt)-OH, wherein Trt is triphenylmethyl(trityl).

131. The process of claim 121 wherein the solid support comprises a resin.

132. The process of claim 121 wherein the solid support comprises a HMBA-AM resin.

133. The process of claim 127 further comprising treating the pyridinone with a halogenating agent to form a halogen substituted pyridinone derivative of the formula:

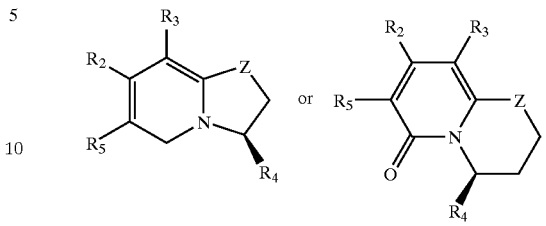

wherein Z comprises S, SO, $SO_2$, O, P, PO, $PO_2$, or $CH_2$; $R_2$ comprises $(CH_2)_nA$ wherein n is a natural number between 0 and 5 and A comprises hydrogen, alkyl, alkenyl, alkynyl, aryl, heteroaryl, substituted alkyl, substituted alkenyl, substituted alkynyl, substituted aryl or substituted heteroaryl; $R_3$ comprises $(CH_2)_mD$ wherein m is a natural number between 0 and 5 and D comprises hydrogen, alkyl, alkenyl, alkynyl, aryl, heteroaryl, substituted alkyl, substituted alkenyl, substituted alkynyl, substituted aryl or substituted heteroaryl; $R_4$ comprises $CO_2Y$, wherein Y comprises hydrogen; and $R_5$ comprises halogen.

134. A method of inhibiting bacterial colonization of a Gram-negative organism, said method comprising administering an antibacterial agent, wherein the antibacterial agent comprises the pyridinone of claim 1, 19, 39 or 40.

135. A method of inhibiting bacterial colonization of a Gram-negative organism, said method comprising administering an antibacterial agent to a subject for the prevention or treatment of a Gram-negative infection, wherein the antibacterial agent comprises the pyridinone of claim 1, 19, 39 or 40.

* * * * *